(12) United States Patent
Hauser et al.

(10) Patent No.: US 11,472,839 B2
(45) Date of Patent: Oct. 18, 2022

(54) PEPTIDE CAPABLE OF FORMING A GEL FOR USE IN TISSUE ENGINEERING AND BIOPRINTING

(71) Applicant: KING ABDULLAH UNIVERSITY OF SCIENCE AND TECHNOLOGY, Thuwal (SA)

(72) Inventors: Charlotte A. E. Hauser, Thuwal (SA); Sandip Jadhav, Thuwal (SA)

(73) Assignee: King Abdullah University of Science and Technology, Thuwal (SA)

( * ) Notice: Subject to any disclaimer, the term of this patent is extended or adjusted under 35 U.S.C. 154(b) by 0 days.

(21) Appl. No.: 16/612,881

(22) PCT Filed: Mar. 29, 2018

(86) PCT No.: PCT/IB2018/052173
§ 371 (c)(1),
(2) Date: Nov. 12, 2019

(87) PCT Pub. No.: WO2018/207036
PCT Pub. Date: Nov. 15, 2018

(65) Prior Publication Data
US 2020/0148720 A1    May 14, 2020

Related U.S. Application Data

(60) Provisional application No. 62/504,976, filed on May 11, 2017.

(51) Int. Cl.
| | | |
|---|---|---|
| *C07K 5/10* | (2006.01) |
| *C07K 5/103* | (2006.01) |
| *A61L 26/00* | (2006.01) |
| *A61L 27/22* | (2006.01) |
| *A61L 27/52* | (2006.01) |
| *A61L 27/54* | (2006.01) |
| *A61L 31/04* | (2006.01) |
| *A61L 31/16* | (2006.01) |
| *C07K 5/107* | (2006.01) |
| *C07K 5/11* | (2006.01) |
| *C07K 5/113* | (2006.01) |

(52) U.S. Cl.
CPC ........ *C07K 5/1013* (2013.01); *A61L 26/0047* (2013.01); *A61L 26/0066* (2013.01); *A61L 27/227* (2013.01); *A61L 27/52* (2013.01); *A61L 27/54* (2013.01); *A61L 31/047* (2013.01); *A61L 31/16* (2013.01); *C07K 5/1016* (2013.01); *C07K 5/1019* (2013.01); *C07K 5/1021* (2013.01); *A61L 2400/06* (2013.01)

(58) Field of Classification Search
CPC .. C07K 5/1013; C07K 5/1016; C07K 5/1019; C07K 5/1021; C07K 5/101; A61L 26/0047; A61L 26/0066; A61L 27/227; A61L 27/52; A61L 27/54; A61L 31/047; A61L 31/16; A61L 2400/06; A61L 27/22; A61L 27/50; A61L 31/043; A61L 31/14; A61L 31/145; A61L 26/0028; A61L 26/0061; A61L 26/008
See application file for complete search history.

(56) References Cited

U.S. PATENT DOCUMENTS

| | | |
|---|---|---|
| 8,729,032 B2 | 5/2014 | Nagai et al. |
| 2011/0113053 A1 | 5/2011 | Khan et al. |
| 2013/0023460 A1 | 1/2013 | Hauser et al. |
| 2014/0349933 A1 | 11/2014 | Hauser et al. |
| 2015/0038428 A1 | 2/2015 | Hauser et al. |
| 2016/0136895 A1 | 5/2016 | Beyer et al. |
| 2016/0288414 A1 | 10/2016 | Ozbolat et al. |
| 2016/0375177 A1 | 12/2016 | Hauser et al. |
| 2018/0030501 A1 | 2/2018 | Bourdeau et al. |
| 2019/0219572 A1 | 7/2019 | Mehra et al. |
| 2019/0321291 A1 | 10/2019 | Connolly et al. |
| 2020/0148720 A1 | 5/2020 | Hauser et al. |
| 2020/0199514 A1 | 6/2020 | Hauser et al. |

(Continued)

FOREIGN PATENT DOCUMENTS

| | | |
|---|---|---|
| CN | 111172100 A | 5/2020 |
| JP | 2013-009598 A | 1/2013 |

(Continued)

OTHER PUBLICATIONS

Fichman et al (Acta Biomaterials, 2014,10, 1671-1682) (Year: 2014).*

(Continued)

*Primary Examiner* — Sudhakar Katakam
(74) *Attorney, Agent, or Firm* — Ajay A. Jagtiani; Miles & Stockbridge P.C.

(57) ABSTRACT

The present invention relates to peptides capable of forming a gel and to their use in tissue engineering and bioprinting. The present invention furthermore relates to a gel comprising a peptide in accordance with the present invention, to a method of preparing such gel and to the use of such gel. In one embodiment, such gel is a hydrogel. The present invention furthermore relates to a wound dressing or wound healing agent comprising a gel according to the present invention and to a surgical implant or stent comprising a peptide scaffold formed by a gel according to the present invention. Moreover, the present invention also relates to a pharmaceutical and/or cosmetic composition, to a biomedical device or an electronic device comprising the peptide according to the present invention.

11 Claims, 20 Drawing Sheets
Specification includes a Sequence Listing.

(56) References Cited

U.S. PATENT DOCUMENTS

| | | |
|---|---|---|
| 2020/0247046 A1 | 8/2020 | Malaquin et al. |
| 2021/0114276 A1 | 4/2021 | Nelson et al. |

FOREIGN PATENT DOCUMENTS

| | | | |
|---|---|---|---|
| JP | 2015-13850 A | 1/2015 | |
| JP | 2016-79190 A | 5/2016 | |
| JP | 2016-530874 A | 10/2016 | |
| JP | 2017-501136 A | 1/2017 | |
| JP | 2020-519605 A | 7/2020 | |
| WO | 2014/104981 A1 | 7/2014 | |
| WO | 2014/186581 A1 | 11/2014 | |
| WO | 2014/197999 A1 | 12/2014 | |
| WO | 2015/066705 A1 | 5/2015 | |
| WO | 2015/080670 A9 | 6/2015 | |
| WO | 2015/080671 A1 | 6/2015 | |
| WO | 20150080671 A1 | 6/2015 | |
| WO | 2016/123693 A1 | 8/2016 | |
| WO | 20160123693 A1 | 8/2016 | |
| WO | 2016/144259 A1 | 9/2016 | |
| WO | 2017/089963 A1 | 6/2017 | |
| WO | 2018/020737 A1 | 2/2018 | |
| WO | 2018/207036 A1 | 11/2018 | |
| WO | 2020/162835 A1 | 8/2020 | |

OTHER PUBLICATIONS

Yihua Loo et al., entitled "Peptide Bioink: Self-Assembling Nanofibrous Scaffolds for Three-Dimensional Organotypic Cultures," Nano Letters 15(10):6919-6925, Sep. 18, 2015.
Gungor-Ozkerim, P. S.; Inci, I.; Zhang, Y. S.; Khademhosseini, A.; Dokmeci, M. R. Biomaterials Science 2018, 6, (5), 915-946.
Donderwinkel, I.; van Hest, J. C. M.; Cameron, N. R. Polymer Chemistry 2017, 8, (31), 4451-4471.
Gopinathan, J.; Noh, I. Biomater Res 2018, 22, 11-11.
Khademhosseini, A.; Camci-Unal, G., 3D Bioprinting in Regenerative Engineering:: Principles and Applications. CRC Press: 2018.
Gjorevski, N.; Sachs, N.; Manfrin, A.; Giger, S.; Bragina, M. E.; Ordonez-Moran, P.; Clevers, H.; Lutolf, M. P. Nature 2016, 539, (7630), 560-564.
Hauser, C. A. E.; Deng, R.; Mishra, A.; Loo, Y.; Khoe, U.; Zhuang, F.; Cheong, D. W.; Accardo, A.; Sullivan, M. B.; Riekel, C.; Ying, J. Y.; Hauser, U. A. Proceedings of the National Academy of Sciences 2011, 108, (4), 1361-1366.
Loo, Y.; Lakshmanan, A.; Ni, M.; Toh, L. L.; Wang, S.; Hauser, C. A. E. Nano Letters 2015, 15, (10), 6919-6925.
Seow, W. Y.; Salgado, G.; Lane, E. B.; Hauser, C. A. E. Scientific Reports 2016, 6, 32670.
Chan, K. H.; Xue, B.; Robinson, R. C.; Hauser, C. A. E. Scientific Reports 2017, 7, (1), 12897.
Wang, H.; Ren, C.; Song, Z.; Wang, L.; Chen, X.; Yang, Z. Nanotechnology 2010, 21, (22), 225606.
Raeburn, J.; Pont, G.; Chen, L.; Cesbron, Y.; Lévy, R.; Adams, D. J. Soft Matter 2012, 8, (4), 1168-1174.
Betush, R. J.; Urban, J. M.; Nilsson, B. L. Peptide Science 2018, 110, (1), e23099.
Lakshmanan, A.; Cheong, D. W.; Accardo, A.; Di Fabrizio, E.; Riekel, C.; Hauser, C. A. Proc Natl Acad Sci U S A 2013, 110, (2), 519-24.
Bowerman, C. J.; Ryan, D. M.; Nissan, D. A.; Nilsson, B. L. Molecular BioSystems 2009, 5, (9), 1058-1069.
Senguen, F. T.; Lee, N. R.; Gu, X.; Ryan, D. M.; Doran, T. M.; Anderson, E. A.; Nilsson, B. L. Molecular BioSystems 2011, 7, (2), 486-496.
Surewicz, W. K.; Mantsch, H. H.; Chapman, D. Biochemistry 1993, 32, (2), 389-394.
Goormaghtigh, E.; Cabiaux, V.; Ruysschaert, J.-M. European Journal of Biochemistry 1990, 193, (2), 409-420.
Williams, R. W.; Dunker, A. K. Journal of Molecular Biology 1981, 152, (4), 783-813.
Rivas-Arancibia, S.; Rodriguez-Martinez, E.; Badillo-Ramirez, I.; López-Gonzalez, U.; Saniger, J. M. Frontiers in Molecular Neuroscience 2017, 10, (137).
Seow, W. Y.; Salgado, G.; Lane, E. B.; Hauser, C. A. E. Scientific Reports 2016, 6.
Tuncaboylu, D. C.; Argun, A.; Sahin, M.; Sari, M.; Okay, O. Polymer 2012, 53, (24), 5513-5522.
Murphy, S. V.; Atala, A. Nature Biotechnology 2014, 32, (8), 773-785.
Grinnell, F. Trends in cell biology 2003, 13, (5), 264-269.
Franco-Barraza, J.; Beacham, D. A.; Amatangelo, M. D.; Cukierman, E. Current protocols in cell biology 2016, 71, (1), 10.9. 1-10.9. 34.
Seliktar, D. Science 2012, 336, (6085), 1124-1128.
Baker, B. M.; Chen, C. S. Journal of cell science 2012, 125, (13), 3015-3024.
Even-Ram, S.; Yamada, K. M. Current opinion in cell biology 2005, 17, (5), 524-532.
Lutolf, M. P.; Lauer-Fields, J. L.; Schmoekel, H. G.; Metters, A. T.; Weber, F. E.; Fields, G. B.; Hubbell, J. A. Proceedings of the National Academy of Sciences 2003, 100, (9), 5413-5418.
Mazzeo, M. S.; Chai, T.; Daviran, M.; Schultz, K. M. ACS applied bio materials 2018, 2, (1), 81-92.
Discher, D. E.; Mooney, D. J.; Zandstra, P. W. Science 2009, 324, (5935), 1673-1677.
Engler, A. J.; Sen, S.; Sweeney, H. L.; Discher, D. E. Cell 2006, 126, (4), 677-689.
Chaudhuri, O.; Gu, L.; Klumpers, D.; Darnell, M.; Bencherif, S. A.; Weaver, J. C.; Huebsch, N.; Lee, H.-p.; Lippens, E.; Duda, G. N. Nature materials 2016, 15, (3), 326-334.
Dalby, M. J.; Gadegaard, N.; Tare, R.; Andar, A.; Riehle, M. O.; Herzyk, P.; Wilkinson, C. D.; Oreffo, R. O. Nature materials 2007, 6, (12), 997-1003.
Haugh, M. G.; Vaughan, T. J.; Madl, C. M.; Raftery, R. M.; McNamara, L. M.; O'Brien, F. J.; Heilshorn, S. C. Biomaterials 2018, 171, 23-33.
Silbernagel, N.; Körner, A.; Balitzki, J.; Jaggy, M.; Bertels, S.; Richter, B.; Hippler, M.; Hellwig, A.; Hecker, M.; Bastmeyer, M. Biomaterials 2020, 227, 119551.
Darnell, M.; Gu, L.; Mooney, D. Biomaterials 2018, 181, 182-188.
Kahin, K.; Khan, Z.; Albagami, M.; Usman, S.; Bahnshal, S.; Alwazani, H.; Majid, M.; Rauf, S.; Hauser, C. In Development of a robotic 3D bioprinting and microfluidic pumping system for tissue and organ engineering, Microfluidics, BioMEMS, and Medical Microsystems XVII, 2019; International Society for Optics and Photonics: p. 108750Q.
Mouser, V. H. M.; Melchels, F. P. W.; Visser, J.; Dhert, W. J. A.; Gawlitta, D.; Maida, J. Biofabrication 2016, 8, (3), 035003.
Chimene, D.; Peak, C. W.; Gentry, J. L.; Carrow, J. K.; Cross, L. M.; Mondragon, E.; Cardoso, G. B.; Kaunas, R.; Gaharwar, A. K. ACS Applied Materials & Interfaces 2018, 10, (12), 9957-9968.
Bertassoni, L. E.; Cardoso, J. C.; Manoharan, V.; Cristino, A. L.; Bhise, N. S.; Araujo, W. A.; Zorlutuna, P.; Vrana, N. E.; Ghaemmaghami, A. M.; Dokmeci, M. R. Biofabrication 2014, 6, (2), 024105.
Markstedt, K.; Mantas, A.; Tournier, I.; Martmez Ávila, H. c.; Hagg, D.; Gatenholm, P. Biomacromolecules 2015, 16, (5), 1489-1496.
Wilson, S. A.; Cross, L. M.; Peak, C. W.; Gaharwar, A. K. ACS applied materials & interfaces 2017, 9, (50), 43449-43458.
Bernal, P. N.; Delrot, P.; Loterie, D.; Li, Y.; Maida, J.; Moser, C.; Levato, R. Advanced materials 2019, 31, (42), 1904209.
Kang, H.-W.; Lee, S. J.; Ko, I. K.; Kengla, C.; Yoo, J. J.; Atala, A. Nature biotechnology 2016, 34, (3), 312.
Hwang, T. L.; Shaka, A. J. Journal of Magnetic Resonance, Series A 1995, 112, (2), 275-279. 46. Derome, A. E.; Williamson, M. P. Journal of Magnetic Resonance (1969) 1990, 88, (1), 177-185.
Piotto, M.; Saudek, V.; Sklenár̆, V. Journal of Biomolecular NMR 1992, 2, (6), 661-665. 48. Sklenar, V.; Piotto, M.; Leppik, R.; Saudek, V. Journal of Magnetic Resonance, Series A 1993, 102, (2), 241-245.
Derome, A. E.; Williamson, M. P. Journal of Magnetic Resonance (1969) 1990, 88, (1), 177-185.

(56) References Cited

OTHER PUBLICATIONS

Sklenar, V.; Piotto, M.; Leppik, R.; Saudek, V. Journal of Magnetic Resonance, Series A 1993, 102, (2), 241-245.

Micsonai, A.; Wien, F.; Kernya, L.; Lee, Y.-H.; Goto, Y.; Réfrégiers, M.; Kardos, J. Proceedings of the National Academy of Sciences 2015, 112, (24), E3095.

Maiti, N. C.; Apetri, M. M.; Zagorski, M. G.; Carey, P. R.; Anderson, V. E. Journal of the American Chemical Society 2004, 126, (8), 2399-2408.

Huebsch, N.; Arany, P. R.; Mao, A. S.; Shvartsman, D.; Ali, O. A.; Bencherif, S. A.; Rivera-Feliciano, J.; Mooney, D. J. Harnessing traction-mediated manipulation of the cell/matrix interface to control stem-cell fate. Nat. Mater 2010, 9, 514.

Kabiri, K.; Omidian, H.; Hashemi, S.; Zohuriaan-Mehr, M. Synthesis of fast-swelling superabsorbent hydrogels: effect of crosslinker type and concentration on porosity and absorption rate. Eur. Polym. J. 2003, 39, 1341-1348.

Hale, B. W.; Goodrich, L. R.; Frisbie, D. D.; McIlwraith, C. W.; Kisiday, J. D. Effect of scaffold dilution on migration of mesenchymal stem cells from fibrin hydrogels. Am. J. Vet. Res. 2012, 73, 313-318.

Cuchiara, M. P.; Allen, A. C.; Chen, T. M.; Miller, J. S.; West, J. L. Multilayer microfluidic PEGDA hydrogels. Biomaterials 2010, 31, 5491-5497.

Cheng, R.; Yan, Y.; Liu, H.; Chen, H.; Pan, G.; Deng, L.; Cui, W. Mechanically enhanced lipo-hydrogel with controlled release of multi-type drugs for bone regeneration. Appl. Mater. Today 2018, 12, 294-308.

Engler, A. J.; Sen, S.; Sweeney, H. L.; Discher, D. E. Matrix elasticity directs stem cell lineage specification. Cell 2006, 126, 677-689.

Sivaraj, K. K.; Adams, R. H. Blood vessel formation and function in bone. Development 2016, 143, 2706-2715.

Kim, S.; Cha, C. Enhanced mechanical and electrical properties of heteroscaled hydrogels infused with aqueous-dispersible hybrid nanofibers. Biofabrication 2020, 12, No. 015020.

Hwang, T. L.; Shaka, A. J., Water Suppression That Works. Excitation Sculpting Using Arbitrary Wave-Forms and Pulsed-Field Gradients. J. Magn. Reson. 1995, 112, (2), 275-279.

Derome, A. E.; Williamson, M. P., Rapid-Pulsing Artifacts in Double-Quantum-Filtered COSY. J. Magn. Reson. 1990, 88, (1), 177-185.

Piotto, M.; Saudek, V.; Sklenář, V., Gradient-Tailored Excitation for Single-Quantum NMR Spectroscopy of Aqueous Solutions. J. Biomol. NMR 1992, 2, (6), 661-665.

Sklenar, V.; Piotto, M.; Leppik, R.; Saudek, V., Gradient-Tailored Water Suppression for 1H—15N HSQC Experiments Optimized to Retain Full Sensitivity. J. Magn. Reson. 1993, 102, (2), 241-245.

Gilbert, D. F.; Erdmann, G.; Zhang, X.; Fritzsche, A.; Demir, K.; Jaedicke, A.; Muehlenberg, K.; Wanker, E. E.; Boutros, M., A novel multiplex cell viability assay for high-throughput RNAi screening. PloS One 2011, 6, (12), e28338.

Alshehri et al., Scaffolds from Self-Assembling Tetrapeptides Support 3D Spreading, Osteogenic Differentiation, and Angiogenesis of Mesenchymal Stem Cells; Biomacromolecules; vol. 22; pp. 2094-2106 (2021).

Arab, "Novel Nanofibrous Peptide Scaffolds for Tissue Regeneration", Dissertation, King Abdullah University of Science and Technology, Thuwal, Saudi Arabia, Apr. 2019.

Ikeno et al., "Effects of self-assembling peptide hydrogel scaffold on bone regeneration with recombinant human bone morphogenetic protein-2"; The International Journal of Oral and Maxillofacial Implants; vol. 28, No. 5, pp. e283-289 (2013).

Liu et al., "Stiffness-mediated mesenchymal stem cell fate decision in 3D-bioprinted hydrogels"; Burns & Trauma, vol. 8, pp. 1-13(2020).

International Search Report and Written Opinion received in International Application No. PCT/IB2021/057623 dated Dec. 13, 2021.

Gauthaman, K.; Venugopal, J. R.; Yee, F. C.; Biswas, A.; Ramakrishna, S.; Bongso, A. Osteogenic differentiation of human Wharton's jelly stem cells on nanofibrous substrates in vitro. Tissue Eng., Part A 2011, 17, 71-81.

Leng, Q.; Chen, L.; Lv, Y. RNA-based scaffolds for bone regeneration: application and mechanisms of mRNA, miRNA and siRNA. Theranostics 2020, 10, 3190.

Erdem, A.; Darabi, M. A.; Nasiri, R.; Sangabathuni, S.; Ertas, Y. N.; Alem, H.; Hosseini, V.; Shamloo, A.; Nasr, A. S.; Ahadian, S. 3D Bioprinting of Oxygenated Cell-Laden Gelatin Methacryloyl Constructs. Adv. Healthcare Mater. 2020, 9, No. 1901794.

Myeroff, C.; Archdeacon, M. Autogenous bone graft: donor sites and techniques. J. Bone Jt. Surg. 2011, 93, 2227-2236.

Silbernagel, N.; Körner, A.; Balitzki, J.; Jaggy, M.; Bertels, S.; Richter, B.; Hippler, M.; Hellwig, A.; Hecker, M.; Bastmeyer, M.; Ullrich, N. D. Shaping the Heart: Structural and Functional Maturation of iPSC-Cardiomyocytes in 3D-Micro-Scaffolds. Biomaterials 2020, 227, No. 119551.

Silber, J. S.; Anderson, D. G.; Daffner, S. D.; Brislin, B. T.; Leland, J. M.; Hilibrand, A. S.; Vaccaro, A. R.; Albert, T. J. Donor site morbidity after anterior iliac crest bone harvest for single-level anterior cervical discectomy and fusion. Spine 2003, 28, 134-139.

Alonzo, M.; Alvarez Primo, F.; Anil Kumar, S.; Mudloff, J. A.; Dominguez, E.; Fregoso, G.; Ortiz, N.; Weiss, W. M.; Joddar, B. Bone tissue engineering techniques, advances, and scaffolds for treatment of bone defects. Curr. Opin. Biomed. Eng. 2021, 17, No. 100248.

Amini, A. R.; Laurencin, C. T.; Nukavarapu, S. P. Bone tissue engineering: recent advances and challenges. Crit. Rev. Biomed. Eng. 2012, 40, 363-408.

Bharadwaz, A.; Jayasuriya, A. C. Recent trends in the application of widely used natural and synthetic polymer nanocomposites in bone tissue regeneration. Mater. Sci. Eng., C 2020, 110, No. 110698.

Pittenger, M. F.; Mackay, A. M.; Beck, S. C.; Jaiswal, R. K.; Douglas, R.; Mosca, J. D.; Moorman, M. A.; Simonetti, D. N.; Craig, S.; Marshak, D. R. Multilineage potential of adult human mesenchymal stem cells. Science 1999, 284, 143-147.

Ma, K.; Laco, F.; Ramakrishna, S.; Liao, S.; Chan, C. K. Differentiation of bone marrow-derived mesenchymal stem cells into multi-layered epidermis-like cells in 3D organotypic coculture. Biomaterials 2009, 30, 3251-3258.

Petite, H.; Viateau, V.; Bensaid, W.; Meunier, A.; de Pollak, C.; Bourguignon, M.; Oudina, K.; Sedel, L.; Guillemin, G. Tissue-engineered bone regeneration. Nat. Biotechnol. 2000, 18, 959.

Takamine, Y.; Tsuchiya, H.; Kitakoji, T.; Kurita, K.; Ono, Y.; Ohshima, Y.; Kitoh, H.; Ishiguro, N.; Iwata, H. Distraction osteogenesis enhanced by osteoblastlike cells and collagen gel. Clin. Orthop. Relat. Res. 2002, 399, 240-246.

Kofidis, T.; Lebl, D. R.; Martinez, E. C.; Hoyt, G.; Tanaka, M.; Robbins, R. C. Novel injectable bioarlificial tissue facilitates targeted, less invasive, large-scale tissue restoration on the beating heart after myocardial injury. Circulation 2005, 112, I-173-I-177.

Yildirim, Y.; Naito, H.; Didié, M.; Karikkineth, B. C.; Biermann, D.; Eschenhagen, T.; Zimmermann, W.-H. Development of a biological ventricular assist device: preliminary data from a small animal model. Circulation 2007, 116, I-16-I-23.

Radisic, M.; Park, H.; Shing, H.; Consi, T.; Schoen, F. J.; Langer, R.; Freed, L. E.; Vunjak-Novakovic, G. Functional assembly of engineered myocardium by electrical stimulation of cardiac myocytes cultured on scaffolds. Proc. Natl. Acad. Sci. U.S.A. 2004, 101, 18129-18134.

Spadaccio, C.; Chachques, E.; Chello, M.; Covino, E.; Chachques, J. C.; Genovese, J. Predifferentiated adult stem cells and matrices for cardiac cell therapy. Asian Cardiovasc. Thorac. Ann. 2010, 18, 79-87.

Kutschka, I.; Chen, I. Y.; Kofidis, T.; Arai, T.; Von Degenfeld, G.; Sheikh, A. Y.; Hendry, S. L.; Pearl, J.; Hoyt, G.; Sista, R.; et al. Collagen matrices enhance survival of transplanted cardiomyoblasts and contribute to functional improvement of ischemic rat hearts. Circulation 2006, 114, I-167-I-173.

Orkin, R.; Gehron, P.; Mcgoodwin, E. B.; Martin, G.; Valentine, T.; Swarm, R. A murine tumor producing a matrix of basement membrane. J. Exp. Med. 1977, 145, 204-220.

Sethi, T.; Rintoul, R. C.; Moore, S. M.; MacKinnon, A. C.; Salter, D.; Choo, C.; Chilvers, E. R.; Dransfield, I.; Donnelly, S. C.; Strieter, R.; et al. Extracellular matrix proteins protect small cell

(56) References Cited

OTHER PUBLICATIONS lung cancer cells against apoptosis: a mechanism for small cell lung cancer growth and drug resistance in vivo. Nat. Med. 1999, 5, 662-668.

Grant, D.; Kibbey, M.; Kinsella, J.; Cid, M.; Kleinman, H. The role of basement membrane in angiogenesis and tumor growth. Pathol., Res. Pract. 1994, 190, 854-863.

Fushimi, H.; Hiratsuka, T.; Okamura, A.; Ono, Y.; Ogura, I.; Nishimura, I. Recombinant collagen polypeptide as a versatile bone graft biomaterial. Commun. Mater. 2020, 1, No. 1.

Kang, P. L.; Huang, H. H.; Chen, T.; Ju, K. C.; Kuo, S. M. Angiogenesis-promoting effect of LIPUS on hADSCs and HUVECs cultured on collagen/hyaluronan scaffolds. Mater. Sci. Eng., C 2019, 102, 22-33.

Blokhuis, T.; Arts, J. C. Bioactive and osteoinductive bone graft substitutes: definitions, facts and myths. Injury 2011, 42, S26-S29.

Barradas, A.; Yuan, H.; van Blitterswijk, C. A.; Habibovic, P. Osteoinductive biomaterials: current knowledge of properties, experimental models and biological mechanisms. Eur. Cells Mater. 2011, 21, 407-429.

Habibovic, P.; de Groot, K. Osteoinductive biomaterials 焗 properties and relevance in bone repair. J. Tissue Eng. Regener. Med. 2007, 1, 25-32.

Ramier, J.; Grande, D.; Bouderlique, T.; Stoilova, O.; Manolova, N.; Rashkov, I.; Langlois, V.; Albanese, P.; Renard, E. From design of bio-based biocomposite electrospun scaffolds to osteogenic differentiation of human mesenchymal stromal cells. J. Mater. Sci. Mater. Med. 2014, 25, 1563-1575.

Adler-Abramovich, L.; Gazit, E. The physical properties of supramolecular peptide assemblies: from building block association to technological applications. Chem. Soc. Rev. 2014, 43, 6881-6893.

Biesalski, M. A.; Knaebel, A.; Tu, R.; Tirrell, M. Cell adhesion on a polymerized peptide-amphiphile monolayer. Biomaterials 2006, 27, 1259-1269.

Mata, A.; Hsu, L.; Capito, R.; Aparicio, C.; Henrikson, K.; Stupp, S. I. Micropatterning of bioactive self-assembling gels. Soft Matter 2009, 5, 1228-1236.

Eren, E. D.; Tansik, G.; Tekinay, A. B.; Guler, M. O. Mineralized peptide nanofiber gels for enhanced osteogenic differentiation. ChemNanoMat 2018, 4, 837-845.

Mata, A.; Geng, Y.; Henrikson, K. J.; Aparicio, C.; Stock, S. R.; Satcher, R. L.; Stupp, S. I. Bone regeneration mediated by biomimetic mineralization of a nanofiber matrix. Biomaterials 2010, 31, 6004-6012.

Derkus, B.; Okesola, B. O.; Barrett, D. W.; D'Este, M.; Chowdhury, T. T.; Eglin, D.; Mata, A. Multicomponent hydrogels for the formation of vascularized bone-like constructs in vitro. Acta Biomater. 2020, 109, 82-94.

Ghosh, M.; Halperin-Stemfeld, M.; Grigoriants, I.; Lee, J.; Nam, K. T.; Adler-Abramovich, L. Arginine-presenting peptide hydrogels decorated with hydroxyapatite as biomimetic scaffolds for bone regeneration. Biomacromolecules 2017, 18, 3541-3550.

Tsutsumi, H.; Kawamura, M.; Mihara, H. Osteoblastic differentiation on hydrogels fabricated from Ca2+-responsive self-assembling peptides functionalized with bioactive peptides. Bioorg. Med. Chem. 2018, 26, 3126-3132.

Zhang, R.; Liu, Y.; Qi, Y.; Zhao, Y.; Nie, G.; Wang, X.; Zheng, S. Self-assembled peptide hydrogel scaffolds with VEGF and BMP-2 Enhanced in vitro angiogenesis and osteogenesis. Oral Dis. 2021, DOI: 10.1111/odi.13785, in press.

Misawa, H.; Kobayashi, N.; Soto-Gutierrez, A.; Chen, Y.; Yoshida, A.; Rivas-Carrillo, J. D.; Navarro-Alvarez, N.; Tanaka, K.; Miki, A.; Takei, J.; et al. PuraMatrix facilitates bone regeneration in bone defects of calvaria in mice. Cell Transplant. 2006, 15, 903-910.

Ikeno, M.; Hibi, H.; Kinoshita, K.; Hattori, H.; Ueda, M. Effects of self-assembling peptide hydrogel scaffold on bone regeneration with recombinant human bone morphogenetic protein-2. Int. J. Oral Maxillofac. Implants 2013, 28, e283-9.

He, B.; Ou, Y.; Chen, S.; Zhao, W.; Zhou, A.; Zhao, J.; Li, H.; Jiang, D.; Zhu, Y. Designer bFGF-incorporated d-form self-assembly peptide nanofiber scaffolds to promote bone repair. Mater. Sci. Eng., C 2017, 74, 451-458.

Tsukamoto, J.; Naruse, K.; Nagai, Y.; Kan, S.; Nakamura, N.; Hata, M.; Omi, M.; Hayashi, T.; Kawai, T.; Matsubara, T. Efficacy of a self-assembling peptide hydrogel, SPG-178-gel, for bone regeneration and three-dimensional osteogenic induction of dental pulp stem ceils. Tissue Eng., Part A 2017, 23, 1394-1402.

Sun, Y.; Li, W.; Wu, X.; Zhang, N.; Zhang, Y.; Ouyang, S.; Song, X.; Fang, X.; Seeram, R.; Xue, W.; He, L.; Wu, W. Functional Self-Assembling Peptide Nanofiber Hydrogels Designed for Nerve Degeneration. ACS Appl. Mater. Interfaces 2016, 8, 2348-2359.

Guo, J.; Su, H.; Zeng, Y.; Liang, Y.-X.; Wong, W. M.; Ellis-Behnke, R. G.; So, K.-F.; Wu, W. Reknitting the injured spinal cord by self-assembling peptide nanofiber scaffold. Nanomedicine 2007, 3, 311-321.

Liu, X.; Wang, X.; Wang, X.; Ren, H.; He, J.; Qiao, L.; Cui, F.-Z. Functionalized self-assembling peptide nanofiber hydrogels mimic stem cell niche to control human adipose stem cell behavior in vitro. Acta Biomater. 2013, 9, 6798-6805.

Rauf, S.; Susapto, H. H.; Kahin, K.; Alshehri, S.; Abdelrahman, S.; Lam, J. H.; Asad, S.; Jadhav, S.; Sundaramurthi, D.; Gao, X.; Hauser, C. A. E. Self-assembling tetrameric peptides allow in situ 3D bioprinting under physiological conditions. J. Mater. Chem. B 2021, 9, 1069-1081.

Susapto, H. H.; Alhattab, D.; Abdelrahman, S.; Khan, Z.; Alshehri, S.; Kahin, K.; Ge, R.; Moretti, M.; Emwas, A.-H.; Hauser, C. A. E. Ultrashort Peptide Bioinks Support Automated Printing of Large-Scale Constructs Assuring Long-Term Survival of Printed Tissue Constructs. Nano Lett. 2021, 21, 2719-2729.

Arthur, A.; Zannettino, A.; Gronthos, S. The therapeutic applications of multipotential mesenchymal/stromal stem cells in skeletal tissue repair. J. Cell. Physiol. 2009, 218, 237-245.

Polo-Corrales, L.; Latorre-Esteves, M.; Ramirez-Vick, J. E. Scaffold design for bone regeneration. J. Nanosci. Nanotechnol. 2014, 14, 15-56.

Holmes, T. C. Novel peptide-based biomaterial scaffolds for tissue engineering. Trends Biotechnol. 2002, 20, 16-21.

Hauser, C. A.; Deng, R.; Mishra, A.; Loo, Y.; Khoe, U.; Zhuang, F.; Cheong, D. W.; Accardo, A.; Sullivan, M. B.; Riekel, C.; Ying, J. Y.; Hauser, U. A. Natural tri- to hexapeptides self-assemble in water to amyloid beta-type fiber aggregates by unexpected alpha-helical intermediate structures. Proc. Natl. Acad. Sci. U.S.A. 2011, 108, 1361-1366.

Lei, Y.; Gojgini, S.; Lam, J.; Segura, T. The spreading, migration and proliferation of mouse mesenchymal stem cells cultured inside hyaluronic acid hydrogels. Biomaterials 2011, 32, 39-47.

International Search Report and Written Opinion received in PCT Application No. PCT/IB2021/057622 dated Dec. 16, 2021.

International Search Report and Written Opinion received in PCT Application No. PCT/IB2021/057625 dated Dec. 14, 2021.

International Search Report and Written Opinion received in PCT Application No. PCT/IB2021/057624 dated Dec. 13, 2021.

International Search Report and Written Opinion received in PCT Application No. PCT/IB2021/057623 dated Dec. 13, 2021.

International Search Report and Written Opinion received in PCT Application No. PCT/IB2021/057996 dated Dec. 20, 2021.

International Search Report and Written Opinion received in PCT Application No. PCT/IB2021/057973 dated Dec. 20, 2021.

International Search Report and Written Opinion received in PCT Application No. PCT/IB2021/059652 dated Feb. 8, 2022.

Susapto et al., "Ultrashort Peptide Bioinks Support Automated Printing of Large-Scale Constructs Assuring Long-Term Survival of Printed Tissue Constructs", Nano Letters, vol. 21, pp. 2719-2729 (2021).

Cembran et al., "Biomimetic Materials and Their Utility in Modeling the 3-Dimensional Neural Environment", iScience, vol. 23, pp. 1-16 (2020).

Cunha et al., "3D Culture of adult mouse neural stem cells within functionalized self-assembling peptide scaffolds", International Journal of Nanomedicine, vol. 6, pp. 943-955 (2011).

(56) References Cited

OTHER PUBLICATIONS

Marchini et al., "Multi-Functionalized Self-Assembling Peptides as Reproducible 3D Cell Culture Systems Enabling Differentiation and Survival of Various Human Neural Stem Cell Lines", frontiers in Neuroscience, vol. 14, Article 413, pp. 1-11 (2020).
Ranjan et al., "A microfiber scaffold-based 3D in vitro human neuronal culture model of Alzheimer's disease", The Royal Society of Chemistry, vol. 8, pp. 4861-4874 (2020).
Zhang et al., "Compatability of neural stem cells with functionalized self-assembling peptide scaffold in vitro", Biotechnology and Bioprocess Engineering, vol. 15, pp. 545-551 (2010).
Arab, "Novel Nanofibrous Peptide Scaffolds for Tissue Regeneration", PhD Thesis, Kind Abdullah University of Science and Technology, pp. 1-131 (2019).
Ikeno et al., "Effects of self-assembling peptide hydrogel scaffold on bone regeneration with recombinant human bone morphogenetic protein-2", The International Journal of Oral and Maxillofacial Implants, vol. 28, No. 5, pp. 283-289 (2013).
Liu et al., "Stiffness-mediated mesenchymal stem cell fate decision in 3D-bioprinted hydrogels", Burns and Trauma, vol. 8, pp. 1-13(2020).
Sundararajan et al., "Use of cyanobacterial gas vesicles as oxygen carriers in cell culture", Cytotechnology, vol. 52, pp. 139-149 (2006).
Upadhyay et al., "Understanding Gas Vesicles and Its Scope in Biotechnological Applications", Advances in Biotechnology and Microbiology, vol. 11, Issue 2, pp. 1-13 (2018).
International Search Report and Written Opinion received in PCT Application No. PCT/IB2018/052173 dated Sep. 9, 2018.
International Search Report and Written Opinion received in PCT Application No. PCT/IB2018/052189 dated Aug. 28, 2018.
Office Action received in U.S. Appl. No. 16/612,881 dated Dec. 30, 2020.
Office Action received in U.S. Appl. No. 16/612,881 dated May 20, 2021.
Office Action received in Korean Application No. 10-2019-7036277 dated Sep. 29, 2021.
Loo et al., "Peptide Biolink: Self-Assembling Nanofibrous Scaffolds for Three-Dimensional Organotypic Cultures", Nano Letters, vol. 15, pp. 6919-6925 (2015).
Bowie et al., "Deciphering the Message in Protein Sequences: Tolerance of Amino Acid Substitutions", Science, vol. 247, pp. 1306-1310 (1990).
Burgess et al., "Possible Dissociation of the Heparin-binding Mitogenic Activities of Heparin-binding (Acid Fibroblast) Growth Factor-1 from Its Receptor-binding Activities by Site-directed Mutagenesis of a Single Lysine Residue", The Journal of Cell Biology, vol. 111, pp. 2129-2138 (1990).
Loo et al., "Peptide Bioink: Printable Nanofibrous Scaffolds for 3D Organotypic Cultures", vol. 15, XP055486589 (2015).
Fichman et al., "Self-assembly of short peptides to form hydrogels: Design of building blocks, physical properties and technological applications", Acta Biomaterials, vol. 10, pp. 1671-1682 (2014).
Loo, Y.; Chan, Y. S.; Szczerbinska, I.; Tan, B. C.; Wan, A. C.; Ng, H. H.; Hauser, C. A. A Chemically Well-Defined, Self-Assembling 3D Substrate for Long-Term Culture of Human Pluripotent Stem Cells. ACS Appl. Bio Mater. 2019, 2, 1406-1412.
Lee, J. H.; Jung, H. W.; Kang, I.-K.; Lee, H. B. Cell behaviour on polymer surfaces with different functional groups. Biomaterials 1994, 15, 705-711.
Guo, S.; Zhu, X.; Li, M.; Shi, L.; Ong, J. L. T.; Janćzewski,D.; Neoh, K. G. Parallel Control over Surface Charge and Wettability Using Polyelectrolyte Architecture: Effect on Protein Adsorption and Cell Adhesion. ACS Appl. Mater. Interfaces 2016, 8, 30552-30563.
Hauser, C. A. E.; Zhang, S. Designer self-assembling peptide nanofiber biological materials. Chem. Soc. Rev. 2010, 39, 2780-2790.
Bowerman, C. J.; Ryan, D. M.; Nissan, D. A.; Nilsson, B. L. The Effect of Increasing Hydrophobicity on the Self-Assembly of Amphipathic β-Sheet Peptides. Mol. Biosyst. 2009, 5, 1058-1069.
Susapto, H. H.; Alhattab, D.; Abdelrahman, S.; Khan, Z.; Alshehri, S.; Kahin, K.; Ge, R.; Moretti, M.; Emwas, A. H.; Hauser, C. A. E. Ultrashort Peptide Bioinks Support Automated Printing of Large-Scale Constructs Assuring Long-Term Survival of Printed Tissue Constructs. Nano Lett. 2021, 2719.
Friedrichs, J.; Taubenberger, A.; Franz, C. M.; Muller, D. J. Cellular Remodelling of Individual Collagen Fibrils Visualized by Time-lapse AFM. J. Mol. Biol. 2007, 372, 594-607.
Nakayama, M.; Amano, M.; Katsumi, A.; Kaneko, T.; Kawabata, S.; Takefuji, M.; Kaibuchi, K. Rho-kinase and myosin II activities are required for cell type and environment specific migration. Genes Cells 2005, 10, 107-117.
Beadle, C.; Assanah, M. C.; Monzo, P.; Vallee, R.; Rosenfeld, S. S.; Canoll, P. The Role of Myosin II in Glioma Invasion of the Brain Mol. Biol. Cell 2008, 19, 3357-3368.
Friedl, P.; Wolf, K.; Lammerding, J. Nuclear mechanics during cell migration. Curr. Opin. Cell Biol. 2011, 23, 55-64.
Balzer, E. M.; Tong, Z.; Paul, C. D.; Hung, W.-C.; Stroka, K. M.; Boggs, A. E.; Martin, S. S.; Konstantopoulos, K. Physical confinement alters tumor cell adhesion and migration phenotypes. FASEB J. 2012, 26, 4045-4056.
Khatau, S. B.; Bloom, R. J.; Bajpai, S.; Razafsky, D.; Zang, S.; Giri, A.; Wu, P.-H.; Marchand, J.; Celedon, A.; Hale, C. M.; Sun, S. X.; Hodzic, D.; Wirtz, D. The distinct roles of the nucleus and nucleus-cytoskeleton connections in three-dimensional cell migration. Sci. Rep. 2012, 2, No. 488.
Wen, J. H.; Vincent, L. G.; Fuhrmann, A.; Choi, Y. S.; Hribar, K. C.; Taylor-Weiner, H.; Chen, S.; Engler, A. J. Interplay of matrix stiffness and protein tethering in stem cell differentiation. Nat. Mater. 2014, 13, 979-987.
Thievessen, I.; Thompson, P. M.; Beriemont, S.; Plevock, K. M.; Plotnikov, S. V.; Zemljic-Harpf, A.; Ross, R. S.; Davidson, M. W.; Danuser, G.; Campbell, S. L.; Waterman, C. M. Vinculin-actin interaction couples actin retrograde flow to focal adhesions, but is dispensable for focal adhesion growth. J. Cell Biol. 2013, 202, 163-177.
Humphries, J. D.; Wang, P.; Streuli, C.; Geiger, B.; Humphries, M. J.; Ballestrem, C. Vinculin controls focal adhesion formation by direct interactions with talin and actin. J. Cell. Biol. 2007, 179, 1043-1057.
Ode, A.; Schoon, J.; Kurtz, A.; Gaetjen, M.; Ode, J. E.; Geissler, S.; Duda, G. N. CD73/5'-ecto-nucleotidase acts as a regulatory factor in osteo-/chondrogenic differentiation of mechanically stimulated mesenchymal stromal cells. Eur. Cells Mater. 2013, 25, 37-47.
Aslan, H.; Zilberman, Y.; Kandel, L.; Liebergall, M.; Oskouian, R. J.; Gazit, D.; Gazit, Z. Osteogenic differentiation of noncultured immunoisolated bone marrow-derived CD105+ cells. Stem Cells 2006, 24, 1728-1737.
Huang, S.; Ingber, D. E. The structural and mechanical complexity of cell-growth control. Nat. Cell Biol. 1999, 1, No. E131.
McBeath, R.; Pirone, D. M.; Nelson, C. M.; Bhadriraju, K.; Chen, C. S. Cell shape, cytoskeletal tension, and RhoA regulate stem cell lineage commitment. Dev. Cell 2004, 6, 483-495.
Katz, B.-Z.; Zamir, E.; Bershadsky, A.; Kam, Z.; Yamada, K. M.; Geiger, B. Physical state of the extracellular matrix regulates the structure and molecular composition of cell-matrix adhesions Mol. Biol. Cell 2000, 11, 1047-1060.
Cukierman, E.; Pankov, R.; Stevens, D. R.; Yamada, K. M. Taking cell-matrix adhesions to the third dimension. Science 2001, 294, 1708-1712.
Fischbach, C.; Kong, H. J.; Hsiong, S. X.; Evangelista, M.B.; Yuen, W.; Mooney, D. J. Cancer cell angiogenic capability is regulated by 3D culture and integrin engagement. Proc. Natl. Acad. Sci. U.S.A. 2009, 106, 399-404.
Hsiong, S. X.; Boontheekul, T.; Huebsch, N.; Mooney, D. J. Cyclic arginine-glycine-aspartate peptides enhance three-dimensional stem cell osteogenic differentiation. Tissue Eng., Part A 2009, 15, 263-272.
Park, J. S.; Huang, N. F.; Kurpinski, K. T.; Patel, S.; Hsu, S.; Li, S. Mechanobiology of mesenchymal stem cells and their use in cardiovascular repair. Front. Biosci. 2007, 12, 5098-5116.

(56) References Cited

OTHER PUBLICATIONS

Tan, S.; Fang, J. Y.; Yang, Z.; Nimni, M. E.; Han, B. The synergetic effect of hydrogel stiffness and growth factor on osteogenic differentiation. Biomaterials 2014, 35, 5294-5306.
Knight, B.; Laukaitis, C.; Akhtar, N.; Hotchin, N. A.; Edlund, M.; Horwitz, A. R. Visualizing muscle cell migration in situ. Curr. Biol. 2000, 10, 576-585.
Roskelley, C.; Desprez, P.; Bissell, M. Extracellular matrix-dependent tissue-specific gene expression in mammary epithelial cells requires both physical and biochemical signal transduction. Proc. Natl. Acad. Sci. U.S.A. 1994, 91, 12378-12382.
Thievessen, I.; Fakhri, N.; Steinwachs, J.; Kraus, V.; McIsaac, R. S.; Gao, L.; Chen, B.-C.; Baird, M. A.; Davidson, M. W.; Betzig, E.; et al. Vinculin is required for cell polarization, migration, and extracellular matrix remodeling in 3D collagen. FASEB J. 2015, 29, 4555-4567.
Case, L. B.; Baird, M. A.; Shtengel, G.; Campbell, S. L.; Hess, H. F.; Davidson, M. W.; Waterman, C. M. Molecular mechanism of vinculin activation and nanoscale spatial organization in focal adhesions. Nat. Cell Biol. 2015, 17, 880-892.
Carisey, A.; Ballestrem, C. Vinculin, an adapter protein in control of cell adhesion signalling. Eur. J. Cell Biol. 2011, 90, 157-163.
Xu, W.; Baribault, H.; Adamson, E. D. Vinculin knockout results in heart and brain defects during embryonic development. Development 1998, 125, 327-337.
Kumar, G.; Tison, C. K.; Chatterjee, K.; Pine, P. S.; McDaniel, J. H.; Salit, M. L.; Young, M. F.; Simon, C. G., Jr. The determination of stem cell fate by 3D scaffold structures through the control of cell shape. Biomaterials 2011, 32, 9188-9196.
Pablo Rodriguez, J.; González, M.; Ríos, S.; Cambiazo, V. Cytoskeletal organization of human mesenchymal stem cells (MSC) changes during their osteogenic differentiation. J. Cell Biochem. 2004, 93, 721-731.
Treiser, M. D.; Yang, E. H.; Gordonov, S.; Cohen, D. M.; Androulakis, I. P.; Kohn, J.; Chen, C. S.; Moghe, P. V. Cytoskeleton-based forecasting of stem cell lineage fates. Proc. Natl. Acad. Sci. U.S.A. 2010, 107, 610-615.
Hunter, G. K.; Hauschka, P. V.; Poole, R. A.; Rosenberg, L. C.; Goldberg, H. A. Nucleation and inhibition of hydroxyapatite formation by mineralized tissue proteins. Biochem. J. 1996, 317, 59-64.
Wang, J.; Cui, X.; Zhou, Y.; Xiang, Q. Core-shell PLGA/ collagen nanofibers loaded with recombinant FN/CDHs as bone tissue engineering scaffolds. Connect. Tissue Res. 2014, 55, 292-298.
Khan, S. N.; Lane, J. M. Bone Tissue Engineering: Basic Science and Clinical Concepts. Orthopedic Tissue Engineering; CRC Press, 2004; pp. 177-194.
Oreffo, R. O.; Kusec, V.; Romberg, S.; Triffitt, J. T. Human bone marrow osteoprogenitors express estrogen receptor-alpha and bone morphogenetic proteins 2 and 4 mRNA during osteoblastic differentiation. J. Cell. Biochem. 1999, 75, 382-392.
Frank, O.; Heim, M.; Jakob, M.; Barbera, A.; Schäfer, D.; Bendik, I.; Dick, W.; Heberer, M.; Martin, I. Real-time quantitative RT-PCR analysis of human bone marrow stromal cells during osteogenic differentiation in vitro. J. Cell. Biochem. 2002, 85, 737-746.
Miron, R.; Zhang, Y. Osteoinduction: a review of old concepts with new standards. J. Dent. Res. 2012, 91, 736-744.
Riffling, S. R.; Matsumoto, H. N.; Mckee, M. D.; Nanci, A.; An, X. R.; Novick, K. E.; Kowalski, A. J.; Noda, M. Denhardt, D. T. Mice lacking osteopontin show normal development and bone structure but display altered osteoclast formation in vitro. J. Bone Miner. Res. 1998, 13, 1101-1111.
Chellaiah, M. A.; Kizer, N.; Biswas, R.; Alvarez, U.; Strauss-Schoenberger, J.; Rifas, L.; Rittling, S. R.; Denhardt, D. T.; Hruska, K. A. Osteopontin deficiency produces osteoclast dysfunction due to reduced CD44 surface expression. Mol. Biol. Cell 2003, 14, 173-189.
Bax, D. V.; Rodgers, U. R.; Bilek, M. M.; Weiss, A. S. Cell adhesion to tropoelastin is mediated via the C-terminal GRKRK motif and integrin αVβ3. J. Biol. Chern. 2009, 284, 28616-28623.

Taddese, S.; Weiss, A. S.; Jahreis, G.; Neubert, R. H.; Schmelzer, C. E. In vitro degradation of human tropoelastin by MMP-12 and the generation of matrikines from domain 24. Matrix Biol. 2009, 28, 84-91.
Getie, M.; Schmelzer, C.; Neubert, R. Characterization of peptides resulting from digestion of human skin elastin with elastase. Proteins 2005, 61, 649-657.
Phillips, J. E.; Petrie, T. A.; Creighton, F. P.; Garcia, A. J. Human mesenchymal stem cell differentiation on self-assembledmonolayers presenting different surface chemistries. Acta Biomater. 2010, 6, 12-20.
Nemir, S.; West, J. L. Synthetic materials in the study of cell response to substrate rigidity. Ann. Biomed. Eng. 2010, 38, 2-20.
Holst, J.; Watson, S.; Lord, M. S.; Eamegdool, S. S.; Bax, D. V.; Nivison-Smith, L. B.; Kondyurin, A.; Ma, L.; Oberhauser, A. F.; Weiss, A. S.; Rasko, J. E. J. Substrate elasticity provides mechanical signals for the expansion of hemopoietic stem and progenitor cells. Nat. Biotechnol. 2010, 28, 1123.
Rowlands, A. S.; George, P. A.; Cooper-White, J. J. Directing osteogenic and myogenic differentiation of MSCs: interplay of stiffness and adhesive ligand presentation. Am. J. Physiol.: Cell Physiol. 2008, 295, C1037-C1044.
Saha, K.; Keung, A. J.; Irwin, E. F.; Li, Y.; Little, L.; Schaffer, D. V.; Healy, K. E. Substrate modulus directs neural stem cell behavior. Biophys. J. 2008, 95, 4426-4438.
Li, Z.; Huang, S.; Liu, Y.; Yao, B.; Hu, T.; Shi, H.; Xie, J.; Fu, X. Scientific Reports 2018, 8, (1), 8020.
Jorgensen, W. L.; Tirado-Rives, J. Proceedings of the National Academy of Sciences of the United States of America 2005, 102, (19), 6665.
Dodda, L. S.; Cabeza de Vaca, I.; Tirado-Rives, J.; Jorgensen, W. L. Nucleic Acids Research 2017,45, (W1), W331-W336.
Abraham, M. J.; Murtola, T.; Schulz, R.; Páll, S.; Smith, J. C.; Hess, B.; Lindahl, E. SoftwareX 2015, 1-2, 19-25.
Darden, T.; York, D.; Pedersen, L. The Journal of Chemical Physics 1993, 98, (12), 10089-10092.
Berendsen, H. J. C.; Postma, J. P. M.; Gunsteren, W. F. v.; DiNola, A.; Haak, J. R. The Journal of Chemical Physics 1984, 81, (8), 3684-3690.
Bussi, G.; Donadio, D.; Parrinello, M. The Journal of Chemical Physics 2007, 126, (1), 014101.
Kim, Y. H.; Baek, N. S.; Han, Y. H.; Chung, M.-A.; Jung, S.-D. Journal of neuroscience methods 2011, 202, (1), 38-44.
Riss, T. L.; Valley, M. P.; Zimprich, C. A.; Niles, A. L.; Kupcho, K. R.; Lazar, D. F. 60. Howe, B.; Umrigar, A.; Tsien, F. JoVE (Journal of Visualized Experiments) 2014, (83), e50203.
Howe, B.; Umrigar, A.; Tsien, F. JoVE (Journal of Visualized Experiments) 2014, (83), e50203.
Worton, R. G.; Duff, C., [27] Karyotyping. In Methods in enzymology, Elsevier: 1979; vol. 58, pp. 322-344.
Perrier, A. L.; Tabar, V.; Barberi, T.; Rubio, M. E.; Bruses, J.; Topf, N.; Harrison, N. L.; Studer, L. Proceedings of the National Academy of Sciences 2004, 101, (34), 12543-12548.
Kang, J.; Lee, I. Cardiovascular Pathology 2006, 15, (4), 218-221.
Blakely, B. D.; Bye, C. R.; Fernando, C. V.; Horne, M. K.; Macheda, M. L.; Stacker, S. A.; Arenas, E.; Parish, C. L. PloS one 2011, 6, (3), e18373.
Bowie et al., "Deciphering the Message in Protein Sequences: Tolerance to Amino Acid Substitutions", Science, vol. 47, pp. 1306-1310(1990).
Burgess et al., "Possible Dissociation of the Heparin-binding Mitogenic Activities of Haparin-binding (Acidic Fibroblast) Growth Factor-1 from Its Receptor-binding Activities by Site-directed Mutagenesis of a Single Lysine Residue", The Journal of Cell Biology, vol. 111, pp. 2129-2138 (1990).
Loo et al, "Peptide Bioink: Printable Nanofibrous Scaffolds for 3D Organotyic Cultures", vol. 15, XP055486589 (2015).
Suspato et al, "Ultrashort Peptide Bioinks Support Automated Printing of Large-Scale Constructs Assuring Long-Term Survival of Printed Tissue Constructs", Nano Lett. 21, 7, pp. 2719-2729 (2021).
Office Action received in Japanese Patent Application No. 2019-561848 dated Apr. 5, 2022.

(56) References Cited

OTHER PUBLICATIONS

Office Action received in Japanese Patent Application No. 2019-561747 dated Mar. 15, 2022.
Notice of Allowance received in Korean Application No. 10-2019-7036377 dated Apr. 6, 2022.
Ali et al., "A Non-Canonical NRPS Is Involved in the Synthesis of Fungisporin and Related Hydrophobic Cyclic Tetrapeptides in Penicillium chrysogenum", PLOS ONE, vol. 9, Issue 6, pp. 1-10 (2014).
Alrashoudi et al., "Fabrication of a Lateral Flow Assay for Rapid In-Field Detection of COVID-19 Antibodies Using Additive Manufacturing Printing Technologies", International Journal of Bioprinting, vol. 7, Issue 4, pp. 76-84 (2021).
Farrera-Soler et al., "Identification of immunodominant linear epitodes from SARS-CoV-2 patient plasma", PLOS ONE, pp. 1-15(2020).
Saatci, Newly developed methods for SARS-CoV-2 detection [SARS-CoV-2 saptanmasinda yeni gelistririlen tani yontemleri], Turk J. Biochem., 45 (5), pp. 465-474 (2020).
Vasco et al., "Macrocyclization of Peptide Side Chains by the Ugi Reaction: Achieving Peptide Folding and Exocyclic N-Functionalization in One Shot", Journal of Organic Chemistry, 80, pp. 6697-6707 (2015).
Xiang et al., "A novel double antibody sandwich-lateral flow immunoassay for the rapid and simple detection of hepatitis C virus", International Journal of Molecular Medicine, 30, pp. 1041-1047 (2012).
Examination Report received in European Patent Application No. 18 718 922.0 dated May 20, 2022.
Office Action received in U.S. Appl. No. 17/401,800 dated Apr. 11, 2022.

\* cited by examiner

Peptide hydrogels cultured with myoblast cells for one week

3D Bioprinting IVZK peptide human bone marrow derived mesenchymal stem cells (hBMSCs)

Day 3   Day 7   Day 14   Day 21

Nucleus – blue
F-actin – red
Vinculin - green

PEPTIDE CAPABLE OF FORMING A GEL FOR USE IN TISSUE ENGINEERING AND BIOPRINTING

CROSS REFERENCE TO RELATED APPLICATIONS

This application is a National Stage Application of International Application Number PCT/IB2018/052173, filed Mar. 29, 2018; which claims priority to U.S. Provisional Application Ser. No. 62/504,976, filed May 11, 2017.

The Sequence Listing for this application is labeled "SeqList-06Nov19-ST25.txt", which was created on Nov. 6, 2019 and is 39 KB. The entire content is incorporated herein by reference in its entirety.

The present invention relates to peptides capable of forming a gel and to their use(s), e.g. in tissue engineering and bioprinting. The present invention furthermore relates to a gel comprising a peptide in accordance with the present invention, to a method of preparing such gel and to the use of such gel. In one embodiment, such gel is a hydrogel. The present invention furthermore relates to a wound dressing or wound healing agent comprising a gel according to the present invention and to a surgical implant or stent comprising a peptide scaffold formed by a gel according to the present invention. Moreover, the present invention also relates to a pharmaceutical and/or cosmetic composition, to a biomedical device or an electronic device comprising peptide(s) according to the present invention. Furthermore, the present invention relates to a kit comprising a first container containing a peptide according to the present invention, and a second container containing an aqueous or organic solution. Moreover, the present invention relates to a method of tissue regeneration, using a gel in accordance with the present invention. Furthermore, the present invention also relates to a method of printing using the peptide(s) and/or the gel(s) according to the present invention. Furthermore, the present invention relates to a method of treatment of a wound and/or for wound healing involving the use of a gel and/or peptide(s) according to the present invention.

BACKGROUND 3D printing technologies can be applied to build tissue-like structures, e.g. in the field of medicine and tissue engineering. Generally, these methods are referred to as 3D bioprinting. Typically, printing inks are used that are synthetic, e.g. polymers, or natural. Also materials from plants, such as alginate, can be used. In particular, with natural materials there can be significant batch-to-batch variations which has an impact on reproducibility and sustainability of the bio-printed 3D structures.

In 3D bioprinting, usually a pre-polymer viscous solution is used to print in 3D, and after printing, either an initiator or (UV or visible) light is used for the polymerization of the 3D construct. Alternatively, a polymer or other macromolecular structure may form by self-assembly. The solution(s), that is (are) used for bioprinting are also referred to as "bioinks". Several factors are important for bioinks to be suitable for 3D bioprinting. These include ease of handling, biocompatibility, biomimetic structure, biodegradability, porosity and mechanical strength. Bioinks need to be prepared with ease and form macromolecular structures at the desired point in space and time. Accordingly, there is a continued need for useful bioinks that can be used in printing and tissue engineering methodologies.

Gels are used for many biomedical applications, such as salves, ointments, wound dressings etc. In many instances, they are formed by naturally derived compounds, such as gelatin or alginates or carrageenans, and thus are subject to naturally inherent variations in quality and composition. Hence there exists a need in the art for novel materials capable of forming gels.

SUMMARY OF THE INVENTION

It was therefore an object of the present invention to provide means to prepare a suitable bioink. It was furthermore an object of the present invention to provide means that are suitable to be used in tissue engineering. It was also an object of the invention to provide materials capable of forming a gel that are easy to synthesise and that are not subject to natural variations.

In a first aspect, the present invention therefore relates to a peptide capable of forming a gel by self-assembly, said peptide having a general formula selected from:

$$Z_o\text{-}X_nBX_mW\text{-}Z'_p, \text{ and} \quad\quad \text{a)}$$

$$Z_o\text{-}WX_mBX_n\text{-}Z'_p, \quad\quad \text{b)}$$

wherein Z is an N-terminal protecting group and Z' is a C-terminal protecting group, with o and p being independently selected from 0 and 1;

wherein X is, independently at each occurrence, an aliphatic amino acid selected from isoleucine, norleucine, leucine, valine, alanine, glycine, homoallylglycine and homopropargylglycine with n and m being integers being independently selected from 0, 1 and 2, with the proviso that $m+n \leq 2$, wherein B is an aromatic amino acid selected from phenylalanine and tryptophan, or is an aliphatic counterpart of said aromatic amino acid, said aliphatic counterpart being selected from cyclohexylalanine, 4-hydroxy-cyclohexylalanine, 3,4-dihydroxycyclohexylalanine.

Wherein W is a polar amino acid selected from aspartic acid, glutamic acid, asparagine, glutamine, lysine, 5-N-ethyl-glutamine (theanine), citrulline, thio-citrulline, cysteine, homocysteine, methionine, ethionine, selenomethionine, telluromethionine, threonine, allothreonine, serine, homoserine, tyrosine, histidine, arginine, homoarginine, ornithine, lysine, N(6)-carboxymethyllysine, histidine, 2,4-diaminobutyric acid (Dab), 2,3-diaminopropionic acid (Dap), and N(6)-carboxymethyllysine, wherein said polar amino acid is preferably selected from the group consisting of aspartic acid, asparagine, glutamic acid, glutamine, serine, threonine, methionine, arginine, histidine, lysine, ornithine (Orn), 2,4-diaminobutyric acid (Dab), and 2,3-diaminopropionic acid (Dap).

In one embodiment, o and p are each 1.

In one embodiment, Z has the general formula —C(O)—R, wherein R is selected from the group consisting of H, unsubstituted or substituted alkyls, and unsubstituted or substituted aryls, wherein R is preferably selected from the group consisting of methyl, ethyl, propyl, isopropyl, butyl and isobutyl, and wherein Z' is —NR$_1$R$_2$, R$_1$ and R$_2$ being independently selected from H and C$_1$-C$_{10}$ alkyl, said —NR$_1$R$_2$ thus forming an amide group at the C-terminus of said peptide, wherein preferably Z is an acetyl group, and wherein preferably Z' is NH$_2$.

In one embodiment, said amino acids in said peptide are either L-amino acids or D-amino acids.

In one embodiment, each of the hydrophilic amino acids has a polar group which is independently selected from a hydroxyl, an ether, a carboxyl, an imido, an amido, an ester, an amino, a guanidine, a thio, a thioether, a seleno and a telluro group.

In one embodiment, said gel is a hydrogel or is an organogel.

In one embodiment, the peptide consists of a sequence selected from

IVFK (SEQ ID NO: 1)
IVOK (SEQ ID NO: 2)
IFVK (SEQ ID NO: 3)
IOVK (SEQ ID NO: 4)
FIVK (SEQ ID NO: 5)
OIVK (SEQ ID NO: 6)
FVIK (SEQ ID NO: 7)
OVIK (SEQ ID NO: 8)
IVFD (SEQ ID NO: 9)
IVOD (SEQ ID NO: 10)
IFVD (SEQ ID NO: 11)
IOVD (SEQ ID NO: 12)
FIVD (SEQ ID NO: 13)
OIVD (SEQ ID NO: 14)
FVID (SEQ ID NO: 15)
OVID (SEQ ID NO: 16)
IVFE (SEQ ID NO: 17)
IVOE (SEQ ID NO: 18)
IFVE (SEQ ID NO: 19)
IOVE (SEQ ID NO: 20)
FIVE (SEQ ID NO: 21)
OIVE (SEQ ID NO: 22)
FVIE (SEQ ID NO: 23)

-continued

OVIE (SEQ ID NO: 24)
IVFS (SEQ ID NO: 25)
IVOS (SEQ ID NO: 26)
IFVS (SEQ ID NO: 27)
IOVS (SEQ ID NO: 28)
FIVS (SEQ ID NO: 29)
OIVS (SEQ ID NO: 30)
FVIS (SEQ ID NO: 31)
OVIS (SEQ ID NO: 32)
IVFR (SEQ ID NO: 33)
IVOR (SEQ ID NO: 34)
IFVR (SEQ ID NO: 35)
IOVR (SEQ ID NO: 36)
FIVR (SEQ ID NO: 37)
OIVR (SEQ ID NO: 38)
FVIR (SEQ ID NO: 39)
OVIR (SEQ ID NO: 40)
IVF(Dab) (SEQ ID NO: 41)
IVO(Dab) (SEQ ID NO: 42)
IFV(Dab) (SEQ ID NO: 43)
IOV(Dab) (SEQ ID NO: 44)
FIV(Dab) (SEQ ID NO: 45)
OIV(Dab) (SEQ ID NO: 46)
FVI(Dab) (SEQ ID NO: 47)
OVI(Dab) (SEQ ID NO: 48)
IVF(Dap) (SEQ ID NO: 49)
IVO(Dap) (SEQ ID NO: 50)

-continued

| | |
|---|---|
| IFV(Dap) | (SEQ ID NO: 51) |
| IOV(Dap) | (SEQ ID NO: 52) |
| FIV(Dap) | (SEQ ID NO: 53) |
| OIV(Dap) | (SEQ ID NO: 54) |
| FVI(Dap) | (SEQ ID NO: 55) |
| OVI(Dap) | (SEQ ID NO: 56) |
| IVF(Orn) | (SEQ ID NO: 57) |
| IVO(Orn) | (SEQ ID NO: 58) |
| IFV(Orn) | (SEQ ID NO: 59) |
| IOV(Orn) | (SEQ ID NO: 60) |
| FIV(Orn) | (SEQ ID NO: 61) |
| OIV(Orn) | (SEQ ID NO: 62) |
| FVI(Orn) | (SEQ ID NO: 63) |
| OVI(Orn) | (SEQ ID NO: 64) |
| KFVI | (SEQ ID NO: 65) |
| KOVI | (SEQ ID NO: 66) |
| KVFI | (SEQ ID NO: 67) |
| KVOI | (SEQ ID NO: 68) |
| KVIF | (SEQ ID NO: 69) |
| KVIO | (SEQ ID NO: 70) |
| KIVF | (SEQ ID NO: 71) |
| KIVO | (SEQ ID NO: 72) |
| DFVI | (SEQ ID NO: 73) |
| DOVI | (SEQ ID NO: 74) |
| DVFI | (SEQ ID NO: 75) |
| DVOI | (SEQ ID NO: 76) |
| DVIF | (SEQ ID NO: 77) |

-continued

| | |
|---|---|
| DVIO | (SEQ ID NO: 78) |
| DIVF | (SEQ ID NO: 79) |
| DIVO | (SEQ ID NO: 80) |
| EFVI | (SEQ ID NO: 81) |
| EOVI | (SEQ ID NO: 82) |
| EVFI | (SEQ ID NO: 83) |
| EVOI | (SEQ ID NO: 84) |
| EVIF | (SEQ ID NO: 85) |
| EVIO | (SEQ ID NO: 86) |
| EIVF | (SEQ ID NO: 87) |
| EIVO | (SEQ ID NO: 88) |
| SFVI | (SEQ ID NO: 89) |
| SOVI | (SEQ ID NO: 90) |
| SVFI | (SEQ ID NO: 91) |
| SVOI | (SEQ ID NO: 92) |
| SVIF | (SEQ ID NO: 93) |
| SVIO | (SEQ ID NO: 94) |
| SIVF | (SEQ ID NO: 95) |
| SIVO | (SEQ ID NO: 96) |
| RFVI | (SEQ ID NO: 97) |
| ROVI | (SEQ ID NO: 98) |
| RVFI | (SEQ ID NO: 99) |
| RVOI | (SEQ ID NO: 100) |
| RVIF | (SEQ ID NO: 101) |
| RVIO | (SEQ ID NO: 102) |
| RIVF | (SEQ ID NO: 103) |
| RIVO | (SEQ ID NO: 104) |

-continued

| Sequence | |
|---|---|
| (Dab)FVI | (SEQ ID NO: 105) |
| (Dab)OVI | (SEQ ID NO: 106) |
| (Dab)VFI | (SEQ ID NO: 107) |
| (Dab)VOI | (SEQ ID NO: 108) |
| (Dab)VIF | (SEQ ID NO: 109) |
| (Dab)VIO | (SEQ ID NO: 110) |
| (Dab)IVF | (SEQ ID NO: 111) |
| (Dab)IVO | (SEQ ID NO: 112) |
| (Dap)FVI | (SEQ ID NO: 113) |
| (Dap)OVI | (SEQ ID NO: 114) |
| (Dap)VFI | (SEQ ID NO: 115) |
| (Dap)VOI | (SEQ ID NO: 116) |
| (Dap)VIF | (SEQ ID NO: 117) |
| (Dap)VIO | (SEQ ID NO: 118) |
| (Dap)IVF | (SEQ ID NO: 119) |
| (Dap)IVO | (SEQ ID NO: 120) |
| (Orn)FVI | (SEQ ID NO: 121) |
| (Orn)OVI | (SEQ ID NO: 122) |
| (Orn)VFI | (SEQ ID NO: 123) |
| (Orn)VOI | (SEQ ID NO: 124) |
| (Orn)VIF | (SEQ ID NO: 125) |
| (Orn)VIO | (SEQ ID NO: 126) |
| (Orn)IVF | (SEQ ID NO: 127) |
| (Orn)IVO | (SEQ ID NO: 128) |

Wherein I=isoleucine, L=leucine, V=valine, F=phenylalanine, K=lysine, D=aspartic acid, O=cyclohexylalanine, (Dab)=2,4-diaminobutyric acid, (Dap)=2,3-diaminopropionic acid, and (Orn)=ornithine; wherein each of the sequences may be protected or unprotected at the N-terminus, preferably acetylated or non-acetylated, and may be amidated or non-amidated at the C-terminus, wherein, preferably, said sequence is selected from

| Sequence | |
|---|---|
| Ac-IVFK-$NH_2$ | (SEQ ID NO: 1) |
| Ac-IVOK-$NH_2$ | (SEQ ID NO: 2) |
| Ac-IFVK-$NH_2$ | (SEQ ID NO: 3) |
| Ac-IOVK-$NH_2$ | (SEQ ID NO: 4) |
| Ac-FIVK-$NH_2$ | (SEQ ID NO: 5) |
| Ac-OIVK-$NH_2$ | (SEQ ID NO: 6) |
| Ac-FVIK-$NH_2$ | (SEQ ID NO: 7) |
| Ac-OVIK-$NH_2$ | (SEQ ID NO: 8) |
| Ac-IVFD-COOH | (SEQ ID NO: 9) |
| Ac-IVOD-COOH | (SEQ ID NO: 10) |
| Ac-IFVD-COOH | (SEQ ID NO: 11) |
| Ac-IOVD-COOH | (SEQ ID NO: 12) |
| Ac-FIVD-COOH | (SEQ ID NO: 13) |
| Ac-OIVD-COOH | (SEQ ID NO: 14) |
| Ac-FVID-COOH | (SEQ ID NO: 15) |
| Ac-OVID-COOH | (SEQ ID NO: 16) |
| Ac-IVFE-COOH | (SEQ ID NO: 17) |
| Ac-IVOE-COOH | (SEQ ID NO: 18) |
| Ac-IFVE-COOH | (SEQ ID NO: 19) |
| Ac-IOVE-COOH | (SEQ ID NO: 20) |
| Ac-FIVE-COOH | (SEQ ID NO: 21) |
| Ac-OIVE-COOH | (SEQ ID NO: 22) |
| Ac-FVIE-COOH | (SEQ ID NO: 23) |
| Ac-OVIE-COOH | (SEQ ID NO: 24) |
| Ac-IVFS--NH2 | (SEQ ID NO: 25) |

-continued

Ac-IVOS--NH2 (SEQ ID NO: 26)

Ac-IFVS--NH2 (SEQ ID NO: 27)

Ac-IOVS--NH2 (SEQ ID NO: 28)

Ac-FIVS--NH2 (SEQ ID NO: 29)

Ac-OIVS--NH2 (SEQ ID NO: 30)

Ac-FVIS--NH2 (SEQ ID NO: 31)

Ac-OVIS--NH2 (SEQ ID NO: 32)

Ac-IVFR-NH$_2$ (SEQ ID NO: 33)

Ac-IVOR-NH$_2$ (SEQ ID NO: 34)

Ac-IFVR-NH$_2$ (SEQ ID NO: 35)

Ac-IOVR-NH$_2$ (SEQ ID NO: 36)

Ac-FIVR-NH$_2$ (SEQ ID NO: 37)

Ac-OIVR-NH$_2$ (SEQ ID NO: 38)

Ac-FVIR-NH$_2$ (SEQ ID NO: 39)

Ac-OVIR-NH$_2$ (SEQ ID NO: 40)

Ac-IVF(Dab)-NH2 (SEQ ID NO: 41)

Ac-IVO(Dab)-NH2 (SEQ ID NO: 42)

Ac-IFV(Dab)-NH2 (SEQ ID NO: 43)

Ac-IOV(Dab)-NH2 (SEQ ID NO: 44)

Ac-FIV(Dab)-NH2 (SEQ ID NO: 45)

Ac-OIV(Dab)-NH2 (SEQ ID NO: 46)

Ac-FVI(Dab)-NH2 (SEQ ID NO: 47)

Ac-OVI(Dab)-NH2 (SEQ ID NO: 48)

Ac-IVF(Dap)-NH2 (SEQ ID NO: 49)

Ac-IVO(Dap)-NH2 (SEQ ID NO: 50)

Ac-IFV(Dap)-NH2 (SEQ ID NO: 51)

Ac-IOV(Dap)-NH2 (SEQ ID NO: 52)

Ac-FIV(Dap)-NH2 (SEQ ID NO: 53)

Ac-OIV(Dap)-NH2 (SEQ ID NO: 54)

Ac-FVI(Dap)-NH2 (SEQ ID NO: 55)

Ac-OVI(Dap)-NH2 (SEQ ID NO: 56)

Ac-IVF(Orn)-NH2 (SEQ ID NO: 57)

Ac-IVO(Orn)-NH2 (SEQ ID NO: 58)

Ac-IFV(Orn)-NH2 (SEQ ID NO: 59)

Ac-IOV(Orn)-NH2 (SEQ ID NO: 60)

Ac-FIV(Orn)-NH2 (SEQ ID NO: 61)

Ac-OIV(Orn)-NH2 (SEQ ID NO: 62)

Ac-FVI(Orn)-NH2 (SEQ ID NO: 63)

Ac-OVI(Orn)-NH2 (SEQ ID NO: 64)

Ac-KFVI-NH$_2$ (SEQ ID NO: 65)

Ac-KOVI-NH$_2$ (SEQ ID NO: 66)

Ac-KVFI-NH$_2$ (SEQ ID NO: 67)

Ac-KVOI-NH$_2$ (SEQ ID NO: 68)

Ac-KVIF-NH$_2$ (SEQ ID NO: 69)

Ac-KVIO-NH$_2$ (SEQ ID NO: 70)

Ac-KIVF-NH$_2$ (SEQ ID NO: 71)

Ac-KIVO-NH$_2$ (SEQ ID NO: 72)

Ac-DFVI-NH$_2$ (SEQ ID NO: 73)

Ac-DOVI-NH$_2$ (SEQ ID NO: 74)

Ac-DVFI-NH$_2$ (SEQ ID NO: 75)

Ac-DVOI-NH$_2$ (SEQ ID NO: 76)

Ac-DVIF-NH$_2$ (SEQ ID NO: 77)

Ac-DVIO-NH$_2$ (SEQ ID NO: 78)

Ac-DIVF-NH$_2$ (SEQ ID NO: 79)

-continued

Ac-DIVO-NH2 (SEQ ID NO: 80)
Ac-EFVI-NH2 (SEQ ID NO: 81)
Ac-EOVI-NH2 (SEQ ID NO: 82)
Ac-EVFI-NH2 (SEQ ID NO: 83)
Ac-EVOI-NH2 (SEQ ID NO: 84)
Ac-EVIF-NH2 (SEQ ID NO: 85)
Ac-EVIO-NH2 (SEQ ID NO: 86)
Ac-EIVF-NH2 (SEQ ID NO: 87)
Ac-EIVO-NH2 (SEQ ID NO: 88)
Ac-SFVI-NH2 (SEQ ID NO: 89)
Ac-SOVI-NH2 (SEQ ID NO: 90)
Ac-SVFI-NH2 (SEQ ID NO: 91)
Ac-SVOI-NH2 (SEQ ID NO: 92)
Ac-SVIF-NH2 (SEQ ID NO: 93)
Ac-SVIO-NH2 (SEQ ID NO: 94)
Ac-SIVF-NH2 (SEQ ID NO: 95)
Ac-SIVO-NH2 (SEQ ID NO: 96)
Ac-RFVI-NH2 (SEQ ID NO: 97)
Ac-ROVI-NH2 (SEQ ID NO: 98)
Ac-RVFI-NH2 (SEQ ID NO: 99)
Ac-RVOI-NH2 (SEQ ID NO: 100)
Ac-RVIF-NH2 (SEQ ID NO: 101)
Ac-RVIO-NH2 (SEQ ID NO: 102)
Ac-RIVF-NH2 (SEQ ID NO: 103)
Ac-RIVO-NH2 (SEQ ID NO: 104)
Ac-(Dab)FVI-NH2 (SEQ ID NO: 105)
Ac-(Dab)OVI-NH2 (SEQ ID NO: 106)
Ac-(Dab)VFI-NH2 (SEQ ID NO: 107)
Ac-(Dab)VOI-NH2 (SEQ ID NO: 108)
Ac-(Dab)VIF-NH2 (SEQ ID NO: 109)
Ac-(Dab)VIO-NH2 (SEQ ID NO: 110)
Ac-(Dab)IVF-NH2 (SEQ ID NO: 111)
Ac-(Dab)IVO-NH2 (SEQ ID NO: 112)
Ac-(Dap)FVI-NH2 (SEQ ID NO: 113)
Ac-(Dap)OVI-NH2 (SEQ ID NO: 114)
Ac-(Dap)VFI-NH2 (SEQ ID NO: 115)
Ac-(Dap)VOI-NH2 (SEQ ID NO: 116)
Ac-(Dap)VIF-NH2 (SEQ ID NO: 117)
Ac-(Dap)VIO-NH2 (SEQ ID NO: 118)
Ac-(Dap)IVF-NH2 (SEQ ID NO: 119)
Ac-(Dap)IVO-NH2 (SEQ ID NO: 120)
Ac-(Orn)FVI-NH2 (SEQ ID NO: 121)
Ac-(Orn)OVI-NH2 (SEQ ID NO: 122)
Ac-(Orn)VFI-NH2 (SEQ ID NO: 123)
Ac-(Orn)VOI-NH2 (SEQ ID NO: 124)
Ac-(Orn)VIF-NH2 (SEQ ID NO: 125)
Ac-(Orn)VIO-NH2 (SEQ ID NO: 126)
Ac-(Orn)IVF-NH2 (SEQ ID NO: 127)
Ac-(Orn)IVO-NH2 (SEQ ID NO: 128)

wherein Ac=acetyl acetylates the N-terminus, NH2=amine, thus amidates the C-terminus, and —COOH=unprotected C-terminus.

In one embodiment, said N-terminal protecting group Z is a peptidomimetic molecule, including natural and synthetic amino acid derivatives, wherein the N-terminus of said peptidomimetic molecule may be modified with a functional group selected from the group consisting of carboxylic acid, amide, alcohol, aldehyde, amine, imine, nitrile, an urea analog, phosphate, carbonate, sulfate, nitrate, maleimide, vinyl sulfone, azide, alkyne, alkene, carbohydrate, imide, peroxide, ester, aryl, ketone, sulphite, nitrite, phosphonate, and silane.

In one embodiment, said C-terminal group Z' is selected from the group of small molecules, functional groups and linkers.

In one embodiment, said C-terminal group Z' is selected from
- functional groups, such as polar or non-polar functional groups,
  - such as (but not limited to)
    - —COOH, —COOR, —COR, —CONHR or —CONRR' with R and R' being selected from the group consisting of H, unsubstituted or substituted alkyls, and unsubstituted or substituted aryls,
    - —NH$_2$, —OH, —SH, —CHO, maleimide, imidoester, carbodiimide ester, isocyanate;
- small molecules,
  - such as (but not limited to) sugars, alcohols, hydroxy acids, amino acids, vitamins, biotin;
- linkers terminating in a polar functional group,
  - such as (but not limited to) ethylenediamine, PEG, carbodiimide ester, imidoester;
- linkers coupled to small molecules or vitamins,
  - such as biotin, sugars, hydroxy acids.

In one embodiment, said C-terminal group Z' is suitable to be used for chemical conjugation or coupling of at least one compound selected from
- bioactive molecules or moieties,
  - such as growth factors, cytokines, lipids, cell receptor ligands, hormones, prodrugs, drugs, vitamins, antigens, antibodies, antibody fragments, oligonucleotides (including but not limited to DNA, messenger RNA, short hairpin RNA, small interfering RNA, microRNA, peptide nucleic acids, aptamers), saccharides;
- label(s), dye(s),
  - such as fluorescent or radioactive label(s), imaging contrast agents;
- pathogens,
  - such as viruses, bacteria and parasites;
- micro- and nanoparticles
- or combinations thereof wherein said chemical conjugation can be carried out before or after self-assembly of the peptide.

In one embodiment, the C-terminus of the peptide is functionalized, such as by chemical conjugation or coupling of at least one compound selected from
- bioactive molecules or moieties,
  - such as growth factors, cytokines, lipids, cell receptor ligands, hormones, prodrugs, drugs, vitamins, antigens, antibodies, antibody fragments, oligonucleotides (including but not limited to DNA, messenger RNA, short hairpin RNA, small interfering RNA, microRNA, peptide nucleic acids, aptamers), saccharides;
- label(s), dye(s),
  - such as fluorescent or radioactive label(s), imaging contrast agents;
- pathogens,
  - such as viruses, bacteria and parasites;
- micro- and nanoparticles
- or combinations thereof wherein said chemical conjugation can be carried out before or after self-assembly of the peptide and/or peptidomimetic.

In one embodiment, said C-terminal group Z' is a peptidomimetic molecule, including natural and synthetic amino acid derivatives, wherein the C-terminus of said peptidomimetic molecule may be modified with a functional group selected from the group consisting of carboxylic acid, amide, alcohol, aldehyde, amine, imine, nitrile, an urea analog, phosphate, carbonate, sulfate, nitrate, maleimide, vinyl sulfone, azide, alkyne, alkene, carbohydrate, imide, peroxide, ester, aryl, ketone, sulphite, nitrite, phosphonate, and silane.

In one embodiment, the peptide according to the present invention is stable in aqueous solution at physiological conditions at ambient temperature for a period of time in the range from 1 day to at least 6 months, preferably to at least 8 months, more preferably to at least 12 months.

In one embodiment, the peptide according to the present invention is stable in aqueous solution at physiological conditions, at a temperature up to 90° C., for at least 1 hour.

In a further aspect, the present invention relates to a hydrogel or organogel comprising a peptide according to the present invention, as defined above.

In one embodiment, the hydrogel is stable in aqueous solution at ambient temperature for a period of at least 1 month, preferably at least 2 to 4 months, more preferably at least 6 to 12 months.

In one embodiment, the hydrogel is characterized by a storage modulus G' to loss modulus G" ratio that is greater than 2 to 5.

In one embodiment, the hydrogel or organogel is characterized by a storage modulus G' from 500 Pa to 200,000 Pa at a frequency in the range of from 0.1 Hz to 100 Hz.

In one embodiment, the hydrogel or organogel has a higher mechanical strength than collagen or its hydrolyzed form (gelatin).

In one embodiment, the hydrogel or organogel according to the present invention comprises fibers of the peptide according to the present invention, as defined above, said fibers defining a network that is capable of entrapping at least one of a microorganism, a virus particle, a peptide, a peptoid, a protein, a nucleic acid, an oligosaccharide, a polysaccharide, a vitamin, an inorganic molecule, a synthetic polymer, a micro- or nanoparticle, a small organic molecule or a pharmaceutically active compound.

In one embodiment, the hydrogel comprises at least one of a microorganism, a virus particle, a peptide, a peptoid, a protein, a nucleic acid, an oligosaccharide, a polysaccharide, a vitamin, an inorganic molecule, a synthetic polymer, a small organic molecule, a micro- or nanoparticle, or a pharmaceutically active compound entrapped by the network of fibers.

In one embodiment, the fibers are coupled to the at least one of a microorganism, a virus particle, a peptide, a peptoid, a protein, a nucleic acid, an oligosaccharide, a polysaccharide, a vitamin, an inorganic molecule, a synthetic polymer, a small organic molecule, a micro- or nanoparticle, or a pharmaceutically active compound entrapped by the network of fibers.

In one embodiment, the hydrogel or organogel is comprised in at least one of a fuel cell, a solar cell, an electronic cell, a biosensing device, a medical device, an implant, a pharmaceutical composition and a cosmetic composition.

In one embodiment, the hydrogel or organogel according to the present invention is injectable.

In a further aspect, the present invention relates to the use of a peptide or of hydrogel or organogel according to the present invention, as defined above, in at least one of the following:
- medical tool kit,
- a fuel cell,
- a solar cell,
- an electronic cell,
- regenerative medicine and tissue regeneration, implantable scaffold
disease model
wound healing,
2D and 3D synthetic cell culture substrate,
stem cell therapy,
injectable therapies,
biosensor development,
high-throughput screening,
biofunctionalized surfaces,
printing
biofabrication, such as bio-printing, and
gene therapy.

In a further aspect, the present invention also relates to a method of preparing a hydrogel or organogel, the method comprising dissolving a peptide according to the present invention in an aqueous solution or an organic solution, respectively.

In one embodiment, the dissolved peptide in aqueous or organic solution is further exposed to temperature, wherein the temperature is in the range from 20° C. to 90° C., preferably from 20° C. to 70° C.

In one embodiment, the peptide is dissolved at a concentration from 0.01 μg/ml to 100 mg/ml, preferably at a concentration from 1 mg/ml to 50 mg/ml, more preferably at a concentration from about 1 mg/ml to about 20 mg/ml.

In a further aspect, the present invention also relates to a cell or tissue graft or device comprising a hydrogel or organogel according to the present invention.

In a further aspect, the present invention also relates to a wound dressing or wound healing agent comprising a hydrogel or organogel according to the present invention.

In a further aspect, the present invention also relates to a surgical implant, or stent, the surgical implant or stent comprising a peptide scaffold, wherein the peptide scaffold is formed by a hydrogel or organogel according to the present invention.

In a further aspect, the present invention also relates to a pharmaceutical and/or cosmetic composition and/or a biomedical device and/or electronic device and/or a solution comprising the peptide according to the present invention.

In one embodiment, the pharmaceutical and/or cosmetic composition and/or the biomedical device, and/or the electronic device and/or the solution according to the present invention further comprises a pharmaceutically active compound.

In one embodiment, the pharmaceutical and/or cosmetic composition and/or solution is provided in the form of a topical gel or cream, a spray, a powder, or a sheet, patch or membrane, or wherein the pharmaceutical and/or cosmetic composition and/or solution is provided in the form of an injectable solution.

In one embodiment, the pharmaceutical and/or cosmetic composition and/or according to the present invention further comprises a pharmaceutically acceptable carrier.

In a further aspect, the present invention also relates to a kit of parts, the kit comprising a first container with a peptide according to the present invention and a second container with an aqueous or organic solution.

In one embodiment, the aqueous or organic solution of the second container further comprises a pharmaceutically active compound,
and/or wherein the first container with a peptide further comprises a pharmaceutically active compound.

In a further aspect, the present invention also relates to an in vitro or in vivo method of tissue regeneration comprising the steps:

(a) providing a hydrogel as defined above,
(b) exposing said hydrogel or organogel to cells which are to form regenerated tissue,
(c) allowing said cells to grow on said hydrogel or organogel.

In one embodiment, the method is performed in vivo, wherein, in step a), said hydrogel is provided at a place in a body where tissue regeneration is intended,
wherein said step a) is preferably performed by injecting said hydrogel at a place in the body where tissue regeneration is intended.

In a further aspect, the present invention also relates to a method of treatment of a wound and for wound healing, said method comprising the step of applying an effective amount of a hydrogel or organogel according to the present invention or a pharmaceutical composition according to the present invention to a wound.

In a further aspect, the present invention also relates to a bioimaging device comprising a hydrogel or organogel according to the present invention for in vitro and/or in vivo use, preferably for oral application, for injection and/or for topical application.

In a further aspect, the present invention also relates to a 2D or 3D cell culture substrate comprising a hydrogel or organogel according to the present invention.

The present inventors surprisingly invented minimal sequences of linear peptides that enable the formation of supergelators in solutions, particularly aqueous solutions, which peptides thus are useful particularly for biological and biomedical applications. These are ultrashort peptides with amino acid compositions between 2-4 amino acids which were rationally designed and investigated. Such ultrashort peptides have the additional advantage that they are extremely easy and economic to synthesise.

The present inventors found that specific amphiphilic peptide sequences show true supergelating properties, forming low molecular weight gels (LMWGs) by entrapping a solvent, e.g. water or other aqueous solutions, such as physiological buffers, of over 99% by weight. Interestingly, these amphiphilic peptides have an innate propensity to self-assemble to three dimensional (3D) fibrous networks in form of hydrogels. These gels can also be termed nanogels, because the diameter of the single fibers of the gel's fiber network have nanometer diameters. These peptide compounds are self-driven by non-covalent interactions to form soft solid material. Based on the nature of the peptides involved, generally composed of natural amino acids, these soft materials can easily be used for biomedical applications, in particular for tissue engineering.

Since the nature of the self-assembling process depends solely on the sequence information, the present inventors have observed that amphiphilic peptides, comprising a mixture of aliphatic and aromatic amino acids with at least one aromatic amino acid, show stronger self-assembling propensities, when the non-polar aromatic residue is exchanged by a non-aromatic counter residue, i.e. phenylalanine is exchanged by cyclohexylalanine. Without wishing to be bound by any theory or mechanism, the present inventors explain this effect of improved gelation properties for peptides in which hydrophobic aromatic residues have been exchanged for non-aromatic residues by an improved self-assembly process. Again without wishing to be bound by any mechanism or theory, the assembly mechanism seems to occur in a stepwise process that involves different structural transition steps, starting from a random structure to a helical intermediate, followed by a beta-sheet and then a beta-turn or cross-beta end structure. In such transition, a more rigid aromatic structure provides less flexibility and thus hampers the required change of secondary structures during scaffold formation.

The inventors could show that the topography of the fibers and the assembled networks strongly resemble the extracellular matrix (ECM). Depending on the nature of the polar amino acid moiety which is part of the amphiphilic peptide structure, nanogels can be formed in situ. The in situ formation of gels allows the parenteral application of therapeutic relevant molecules such as therapeutics, cells, nanoparticles, small molecules, nucleic acids, and others. Depending on the nature of the amino acids side chain, side-specific biofunctionalization can be introduced to the peptide structure, although this must be done under premise that gelation and the formation of supramolecular structures is not enabled.

Thus, functional groups, such as glycans, i.e. by glycosylation, aldehyde or keto groups, phosphorylation, sulfuration, nanoparticle-functionalization, biotin-functionalization for affinity anchors such as streptavidin, besides others, addition of bioactive sequences such as the RGD adherence-promoting motif, cross-linking motifs, etc.

Furthermore, the peptides according to the present invention are also particularly useful for formulating aqueous or other solvent compositions, herein also sometimes referred to as "inks" or "bioinks", which can be used for printing structures, in particular three-dimensional ("3D") structures. Such printed structures make use of the gelation properties of the peptides according to the present invention and can themselves act as scaffolds for other entities, such as cells, compounds, particles, in particular nanoparticles etc.

BRIEF DESCRIPTION OF THE DRAWINGS

To further illustrate the technical features of embodiments of the present invention more clearly, the accompanying drawings provided for describing various embodiments are introduced briefly in the following. They are merely exemplary embodiments of the present invention and are not intended to limit it. Modifications on these embodiments are possible without departing from the scope of the present invention as defined in the claims.

The average fiber diameter of IVFK peptide was calculated by plotting the distribution curve using the data collected from 13 TEM images. The average diameter is 10.3 nm (left low panel).

The IVZK TEM shows three different types of average diameters (4.0 nm, 8.6 nm and 15.5 nm) (right low panel). The number of images used to calculate the average diameter were 10.

The fibers diameter with 8.6 nm were the most abundant ones as compared to other fiber diameters. The single monomer fiber has an average diameter of 4.0 nm.

Figure 2:
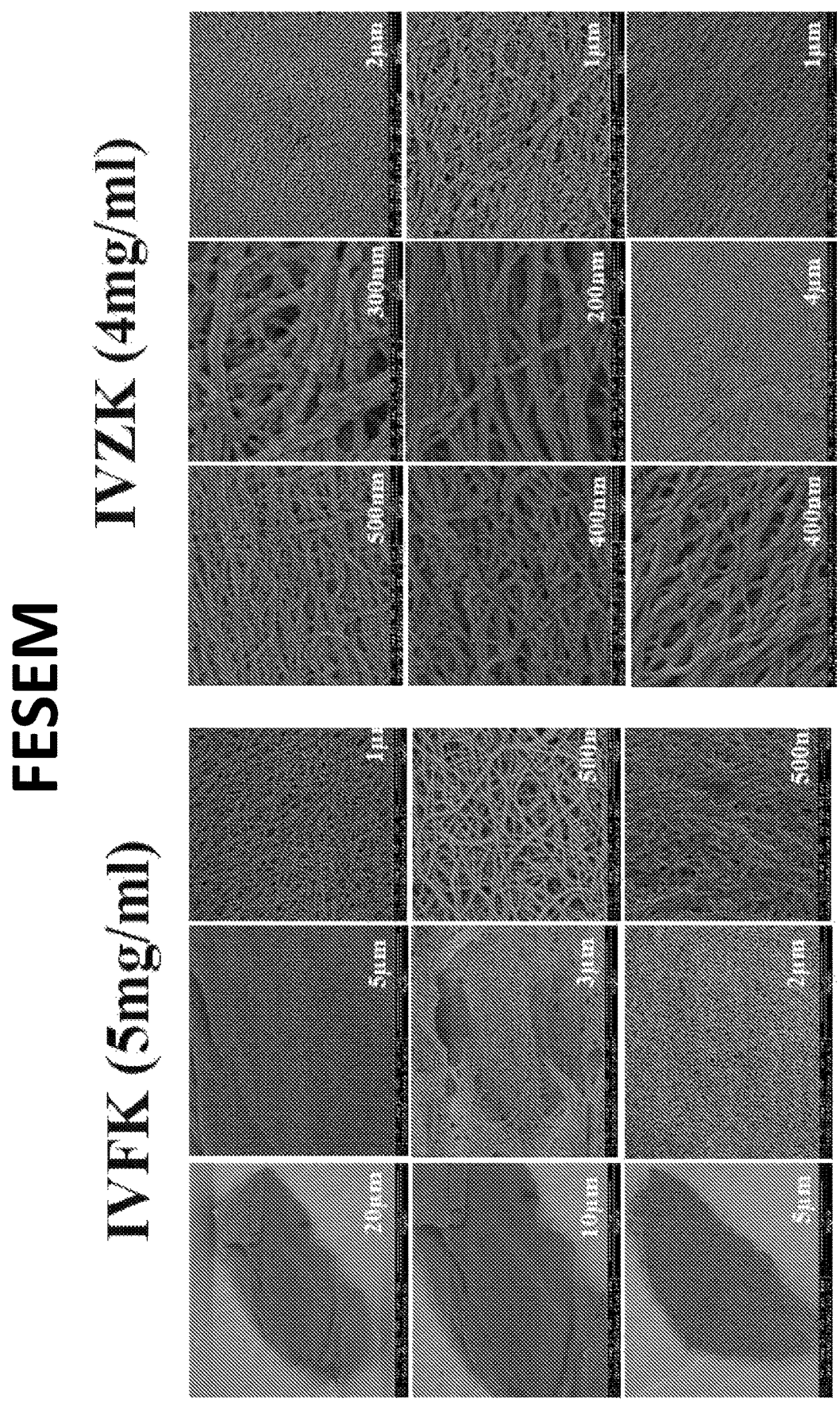

FIG. 2 shows morphological characterization of the self-assembling peptide IVFK and IVZK hydrogels by FESEM showing different magnifications.

Figure 3:
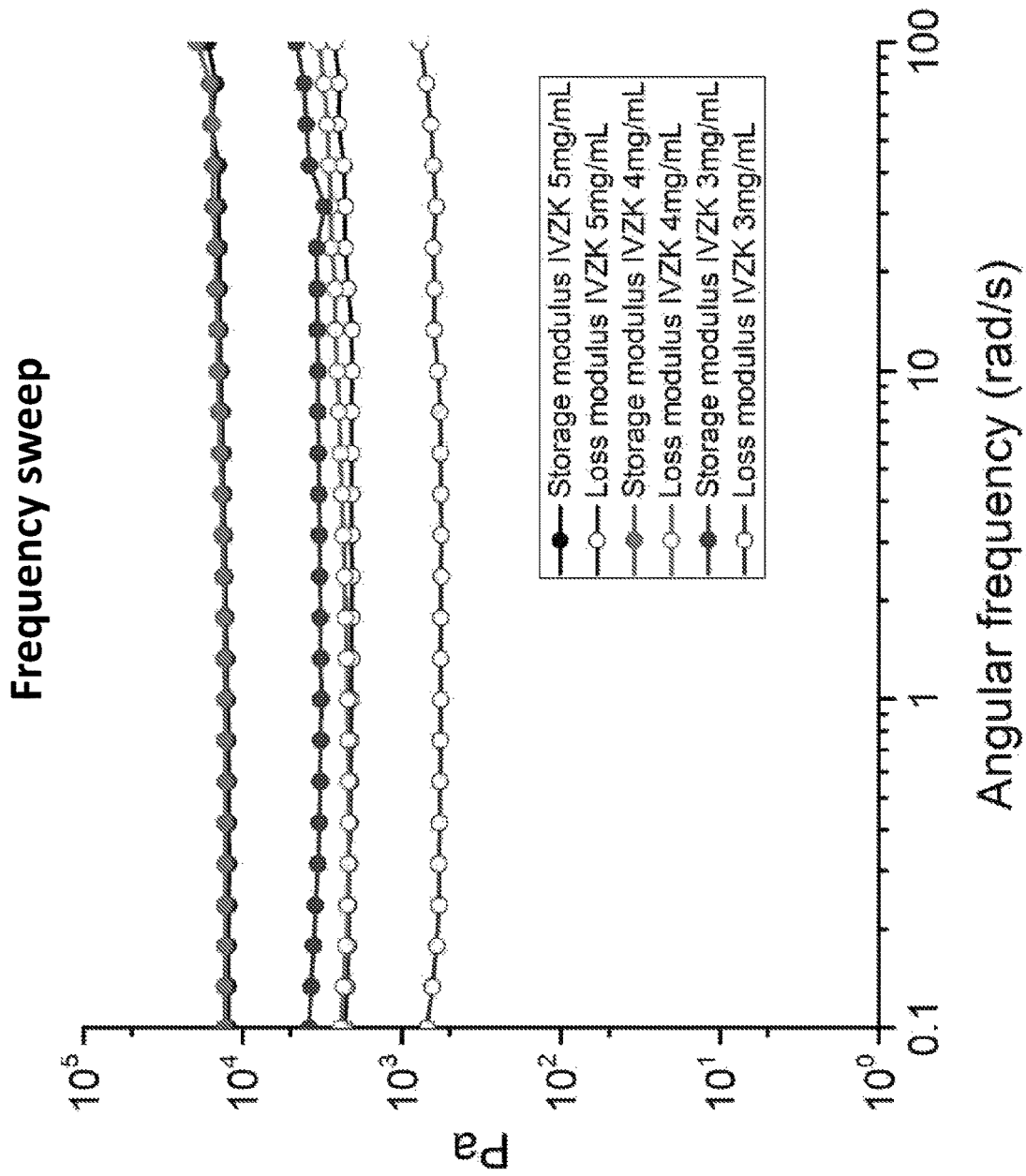

FIG. 3 shows high mechanical strength was demonstrated for the peptide hydrogels. Storage moduli (G') of different hydrogels (20 mg/mL) as a function of angular frequency under 0.1% strain, at 25° C. Frequency sweep was performed at 0.1% strain.

Figure 4:
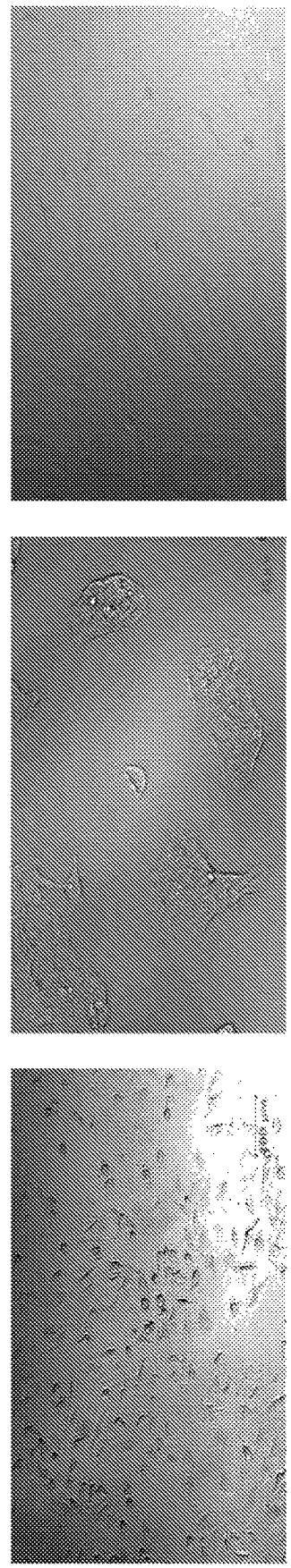

FIG. 4 shows cell morphology of HeLa cells, HEK 293Tcells, and human dermal fibroblasts used for 3D cell culturing on peptide hydrogels.

Figure 5:
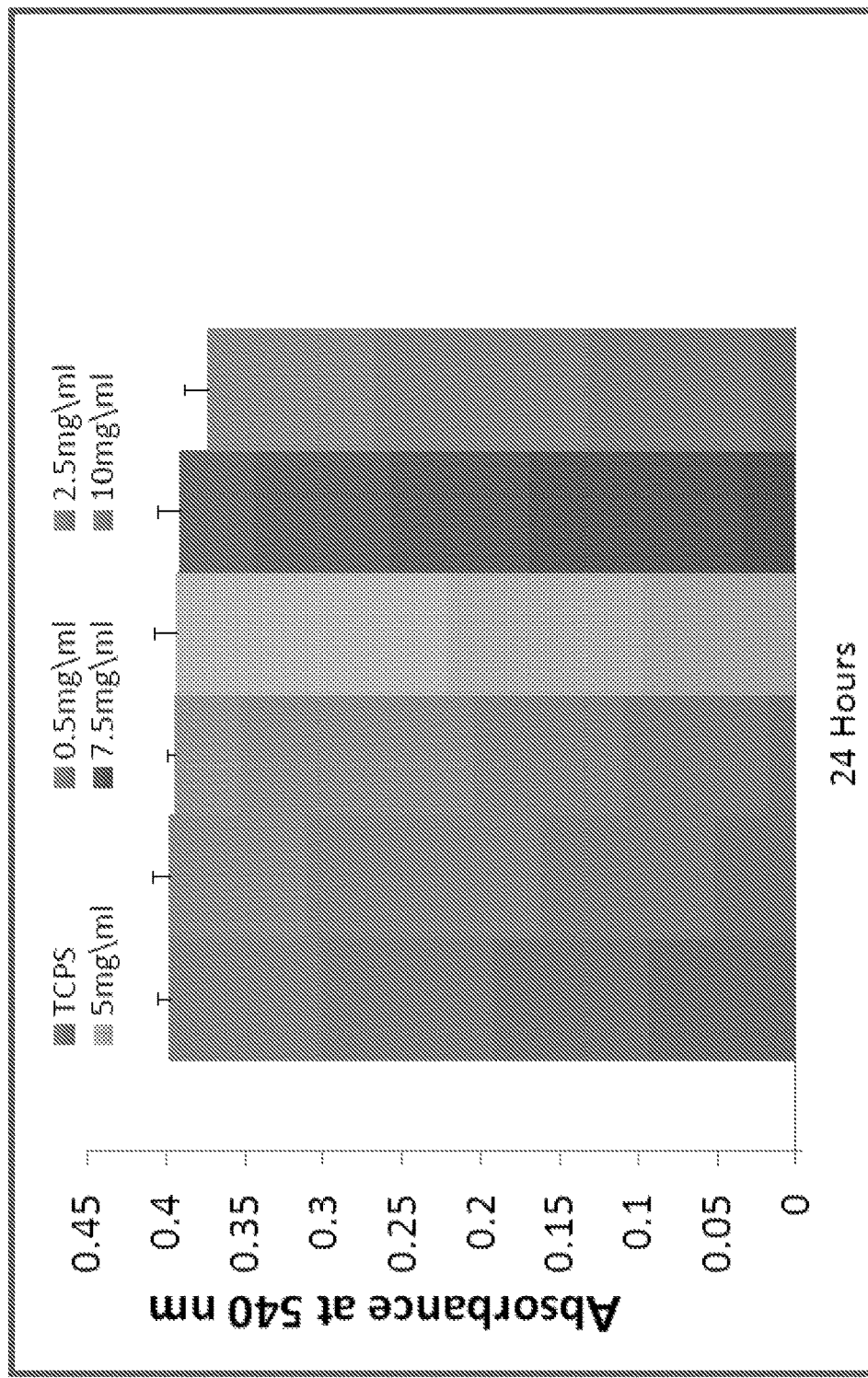

FIG. 5 shows graphical presentation of the MTT biocompatibility assay of HeLa with IVFK peptide.

Figure 6:
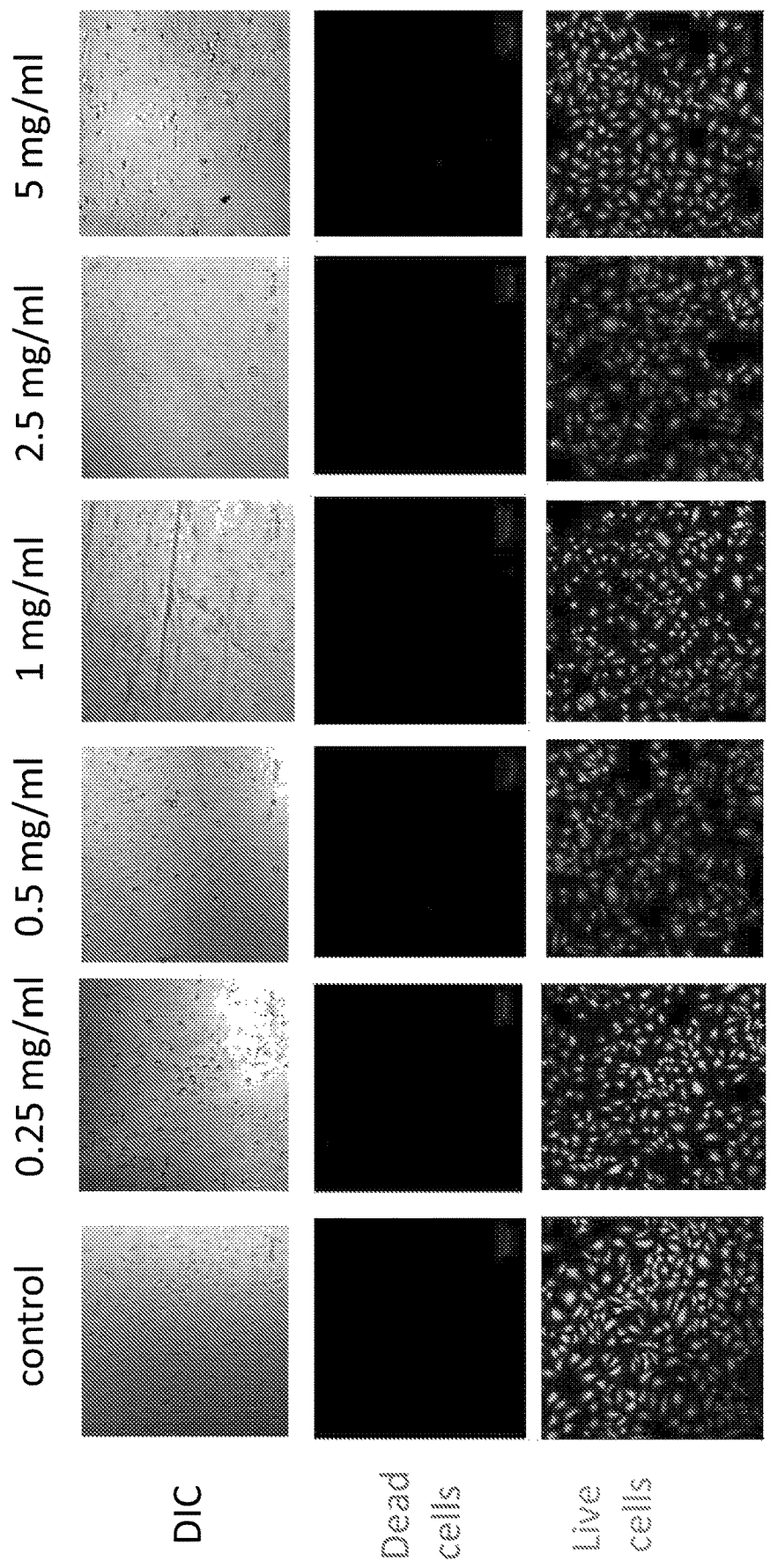

FIG. 6 shows Live/Dead staining of HeLa cells treated with IVFK peptide.

Figure 7:
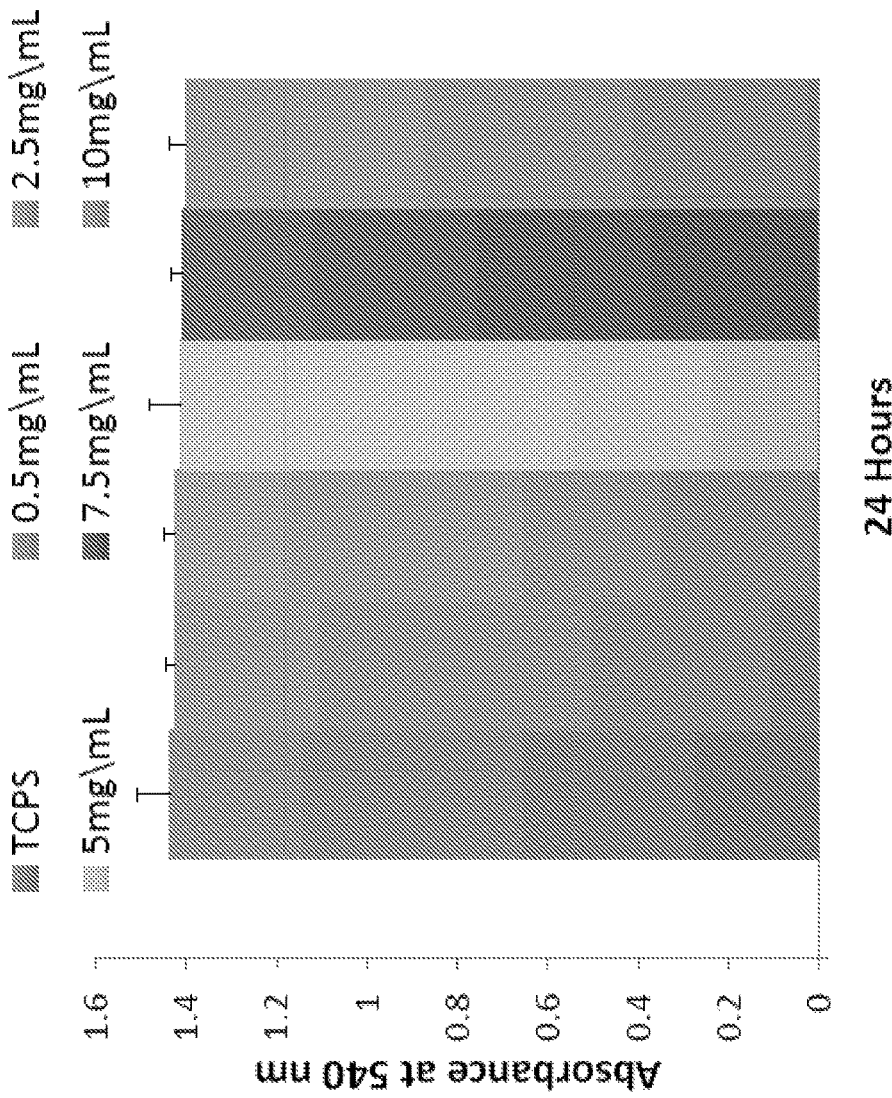

FIG. 7 shows graphical presentation of the MTT biocompatibility assay of HeLa with IVZK peptide.

Figure 8:
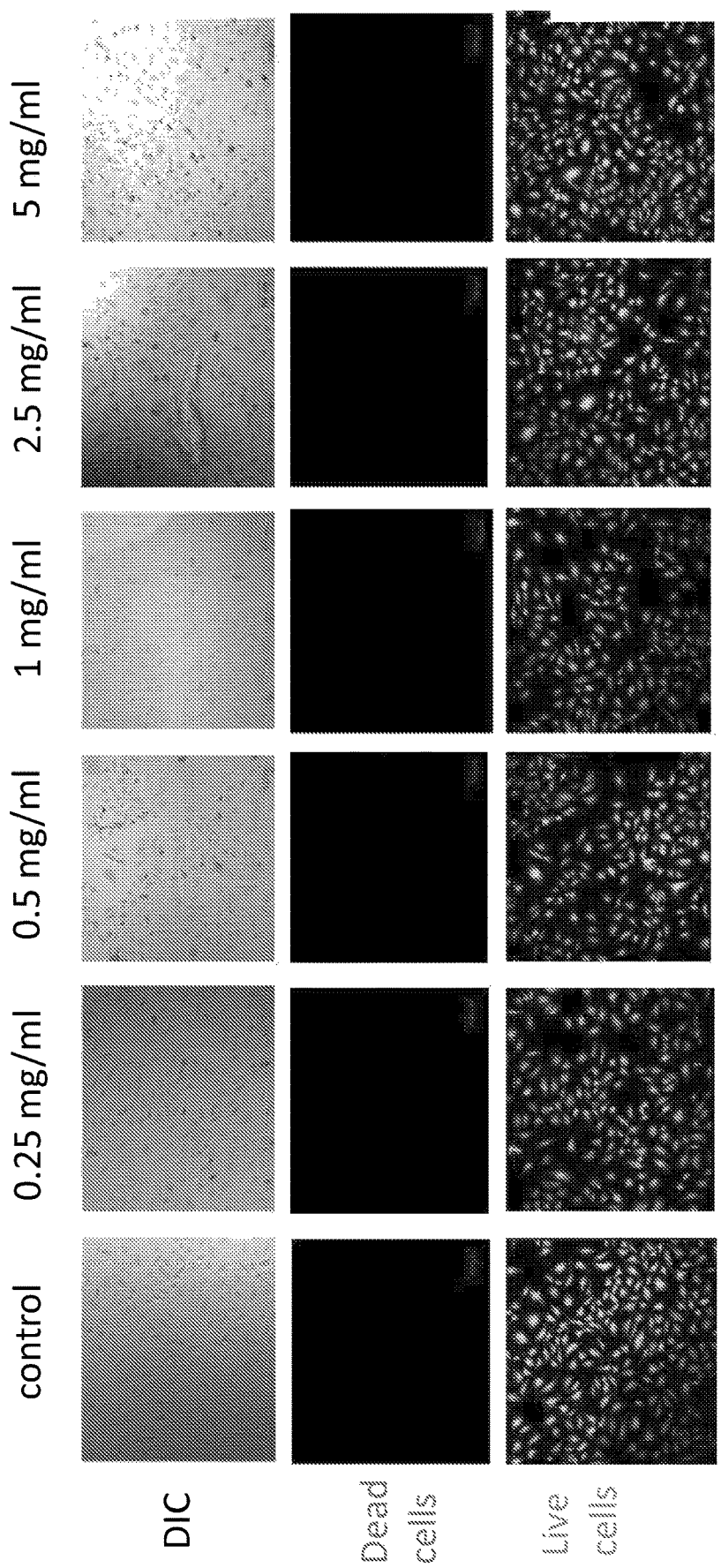

FIG. 8 shows Live/dead images of HeLa cells treated with IVZK peptide.

Figure 9:
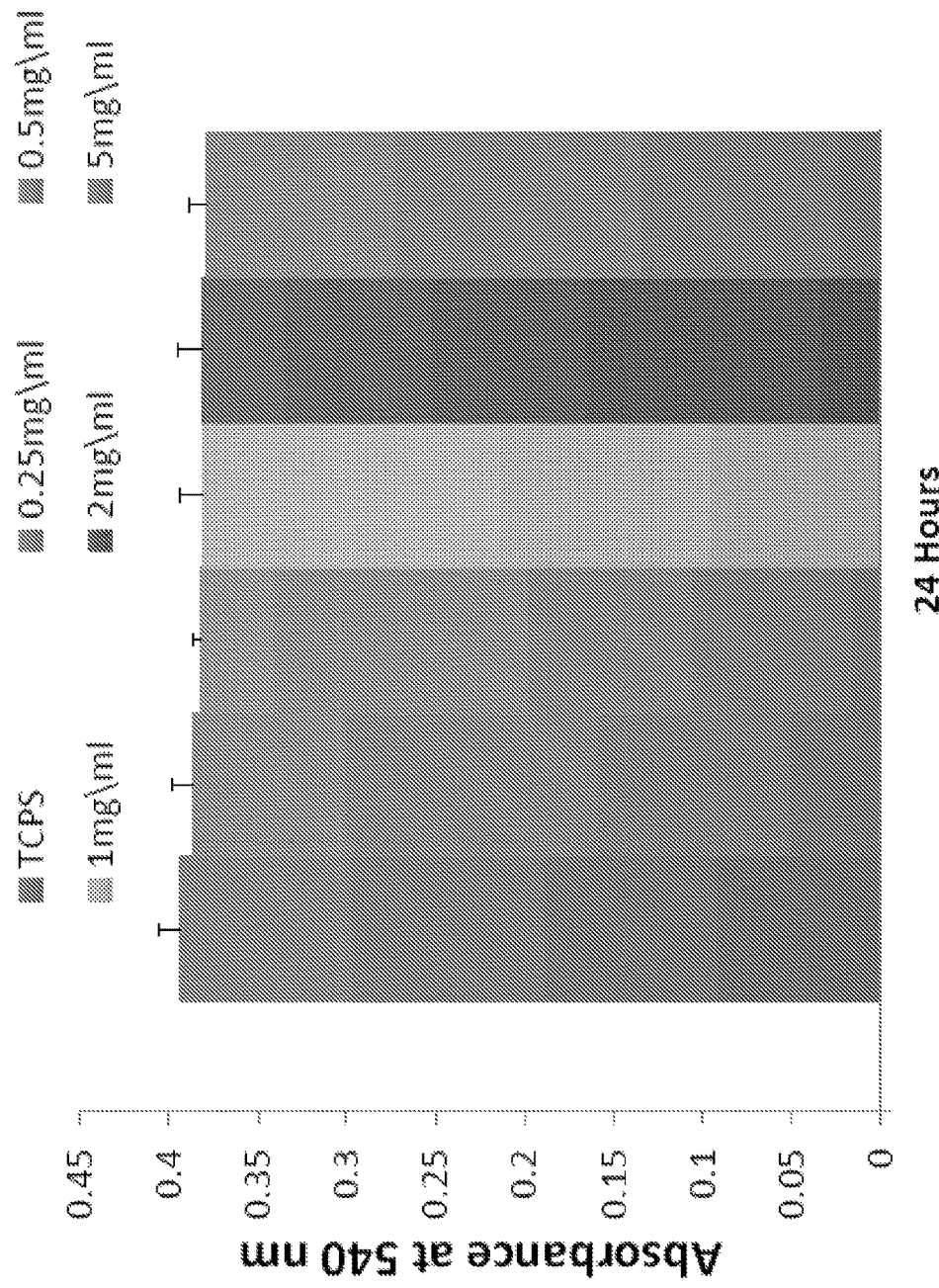

FIG. 9 shows graphical presentation of the MTT biocompatibility assay of HEK 293 T with IVFK peptide.

Figure 10:
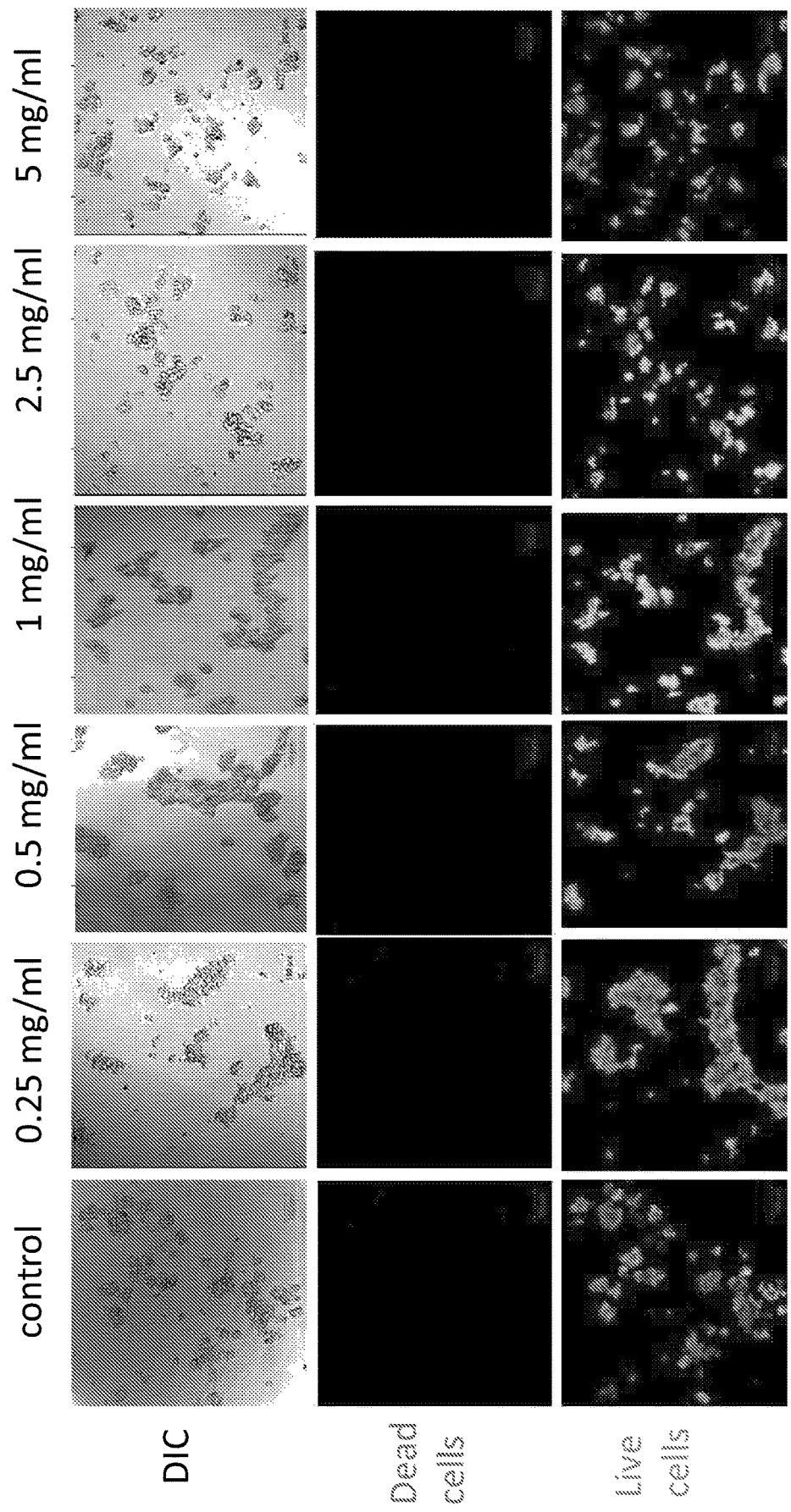
Figure 11:
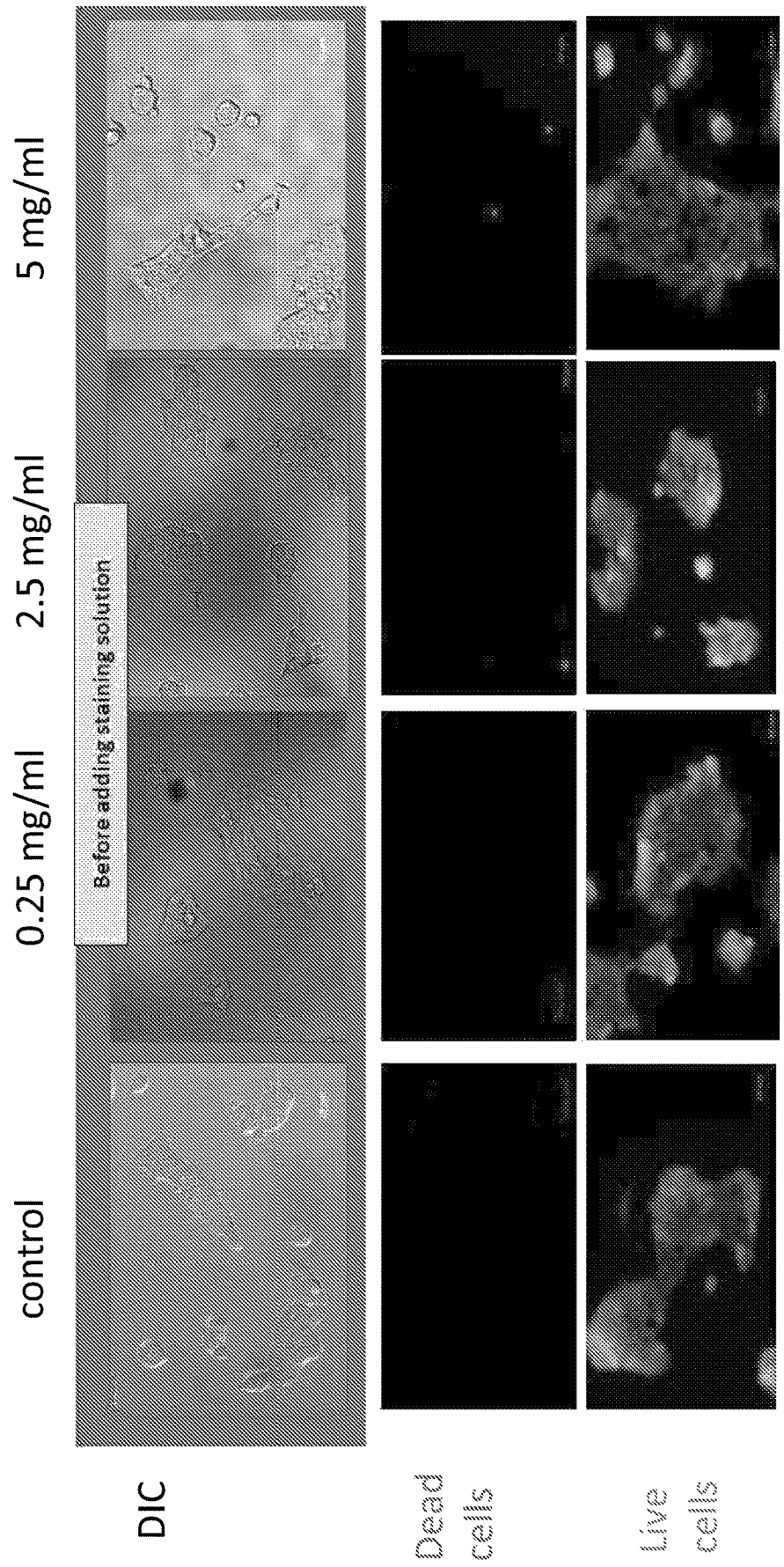

FIG. 10 shows 3D Cell Viability Assay of Bioprinted Constructs. Live/Dead Staining of HEK 293 T cells treated with IVFK peptide FIG. 11 shows 3D Cell Viability Assay of Bioprinted Constructs. Live/Dead staining of HEK 293 T cells treated with IVFK peptide.

Figure 12:
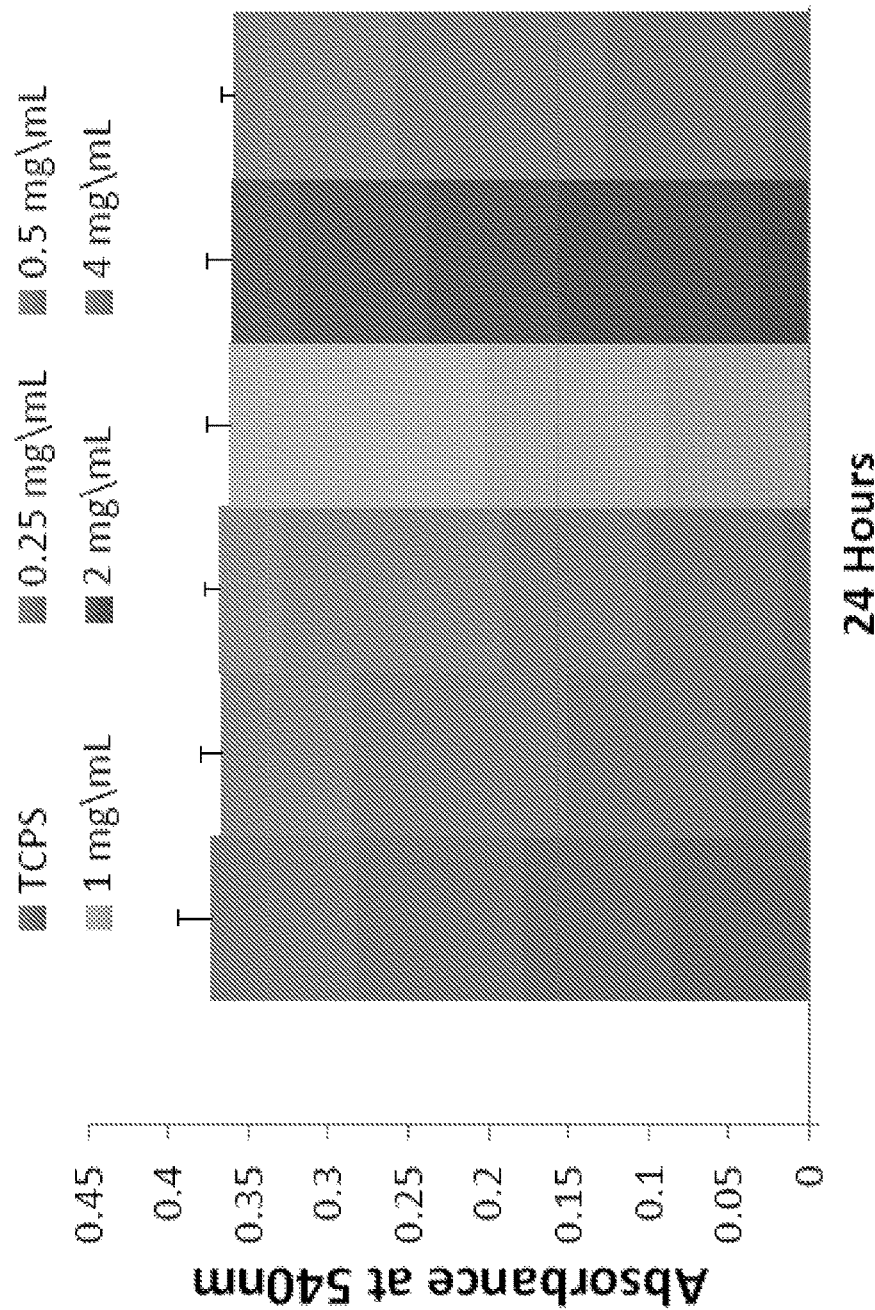

FIG. 12 shows graphical presentation of the MTT biocompatibility assay of HEK 293 T with IVZK peptide.

Figure 13:
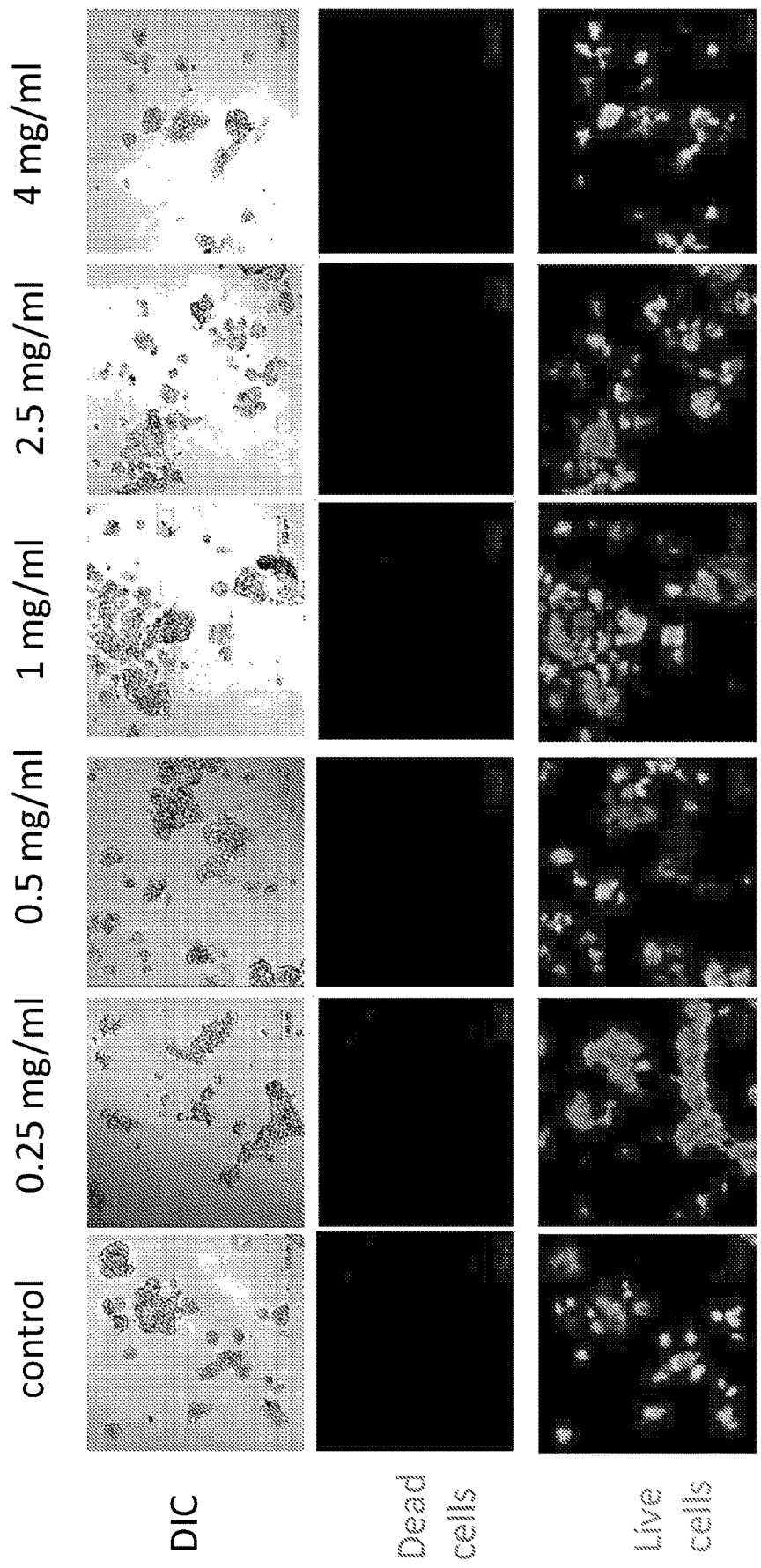

FIG. 13 shows 3D cell viability assay of bioprinted constructs. Live/Dead staining of HEK 293 T cells treated with IVZK peptide.

Figure 14:
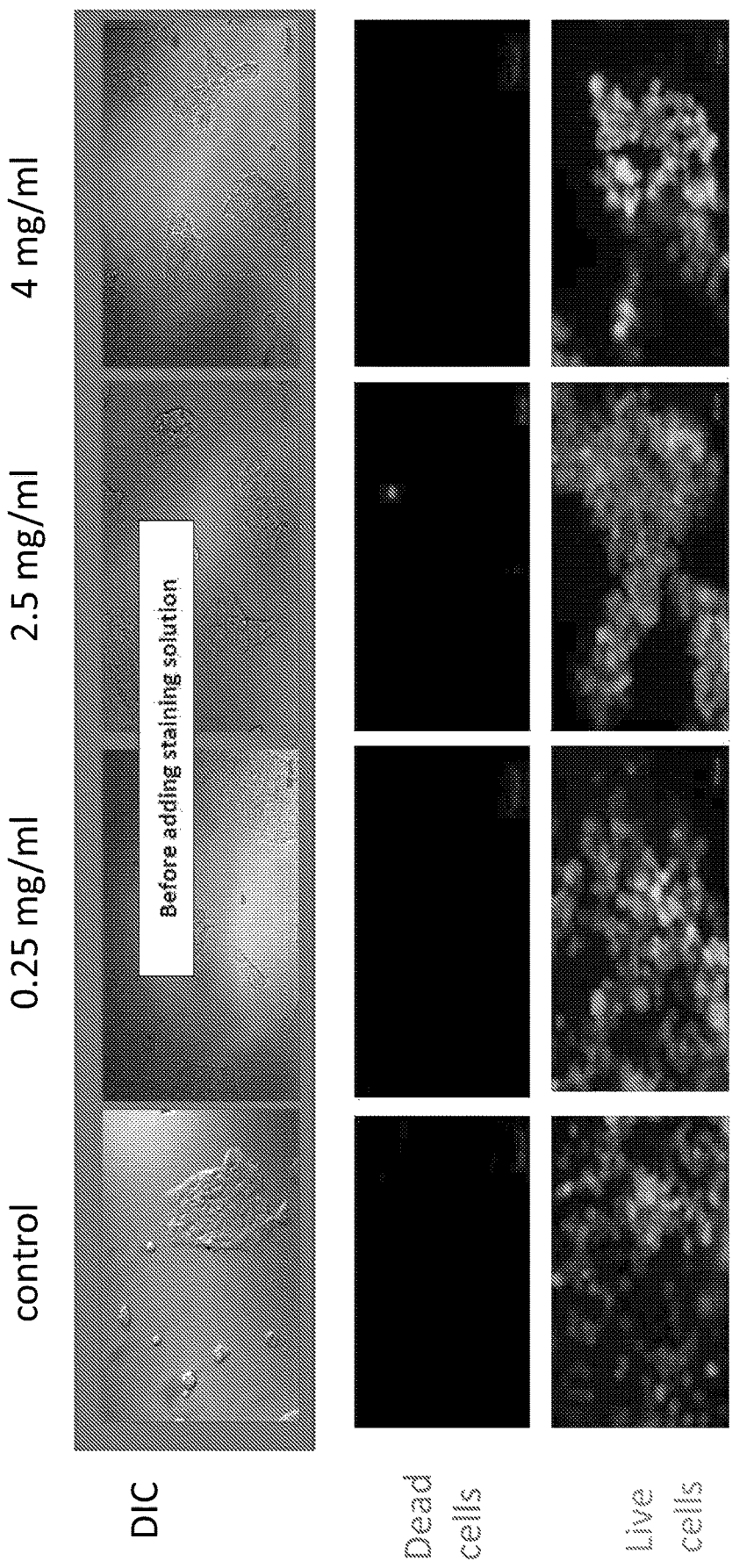

FIG. 14 shows 3D cell viability assay of bioprinted constructs. Live/Dead staining of HEK 293 T cells treated with IVZK peptide.

Figure 15:
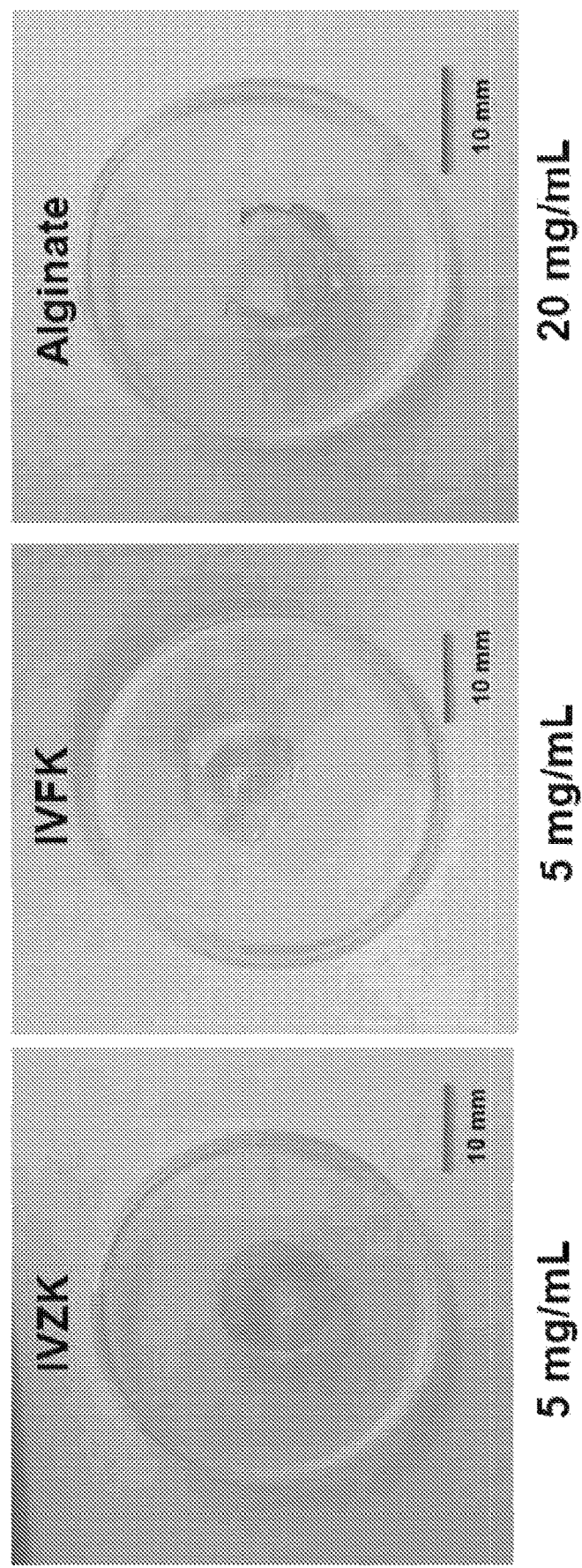

FIG. 15 shows peptide hydrogels cultured with human myoblast cells for one week.

Figure 16:
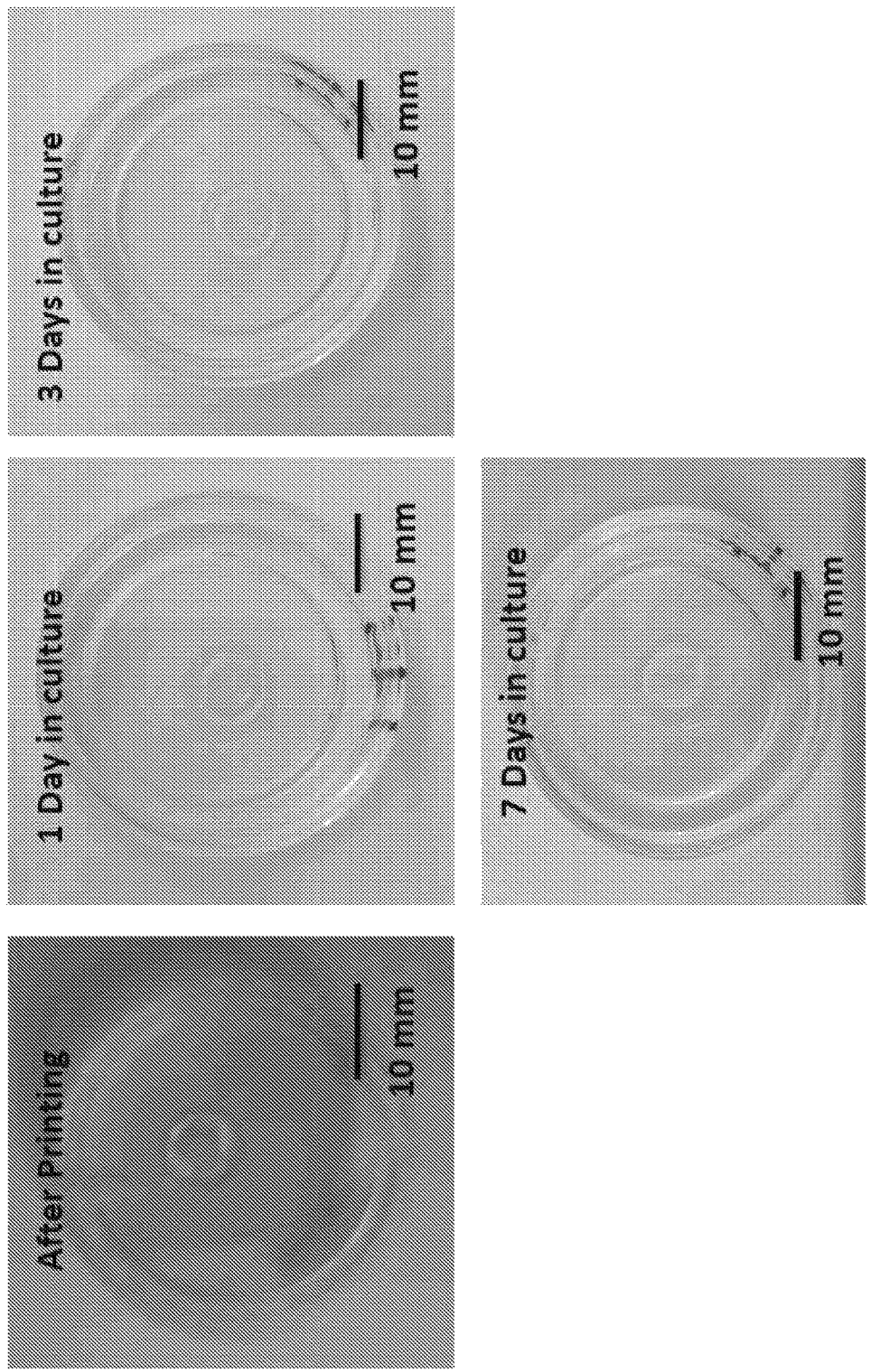

FIG. 16 shows 3D bioprinting of human dermal fibroblast cells using IVZK peptide solution as bioink (human dermal fibroblast cells—4 million/ml; peptide—10 mg/ml).

Figure 17:
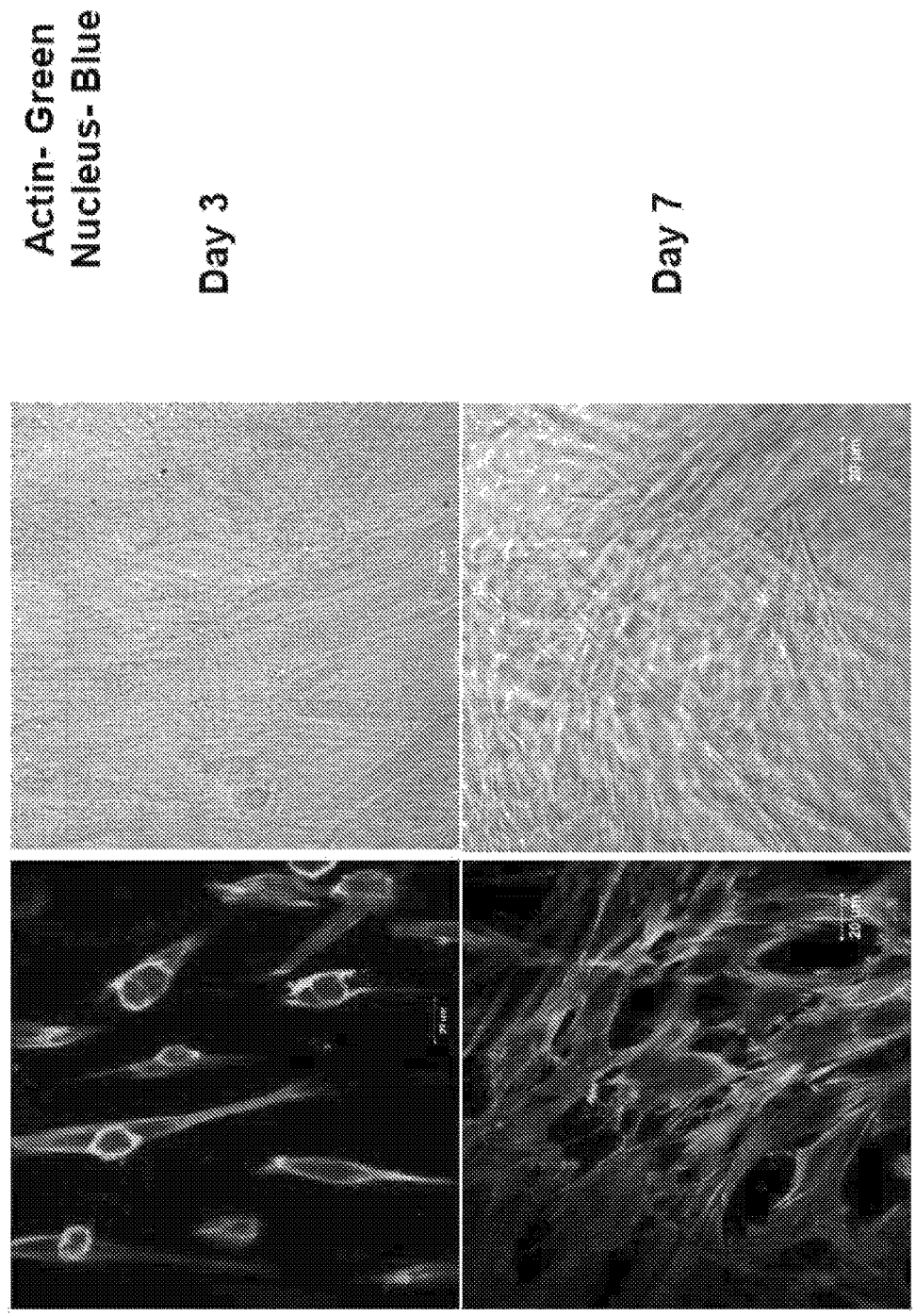

FIG. 17 shows fluorescent images of human dermal fibroblasts embedded IVZK peptide hydrogels (human dermal fibroblast cells—4 million/ml; peptide—10 mg/ml). Actin cytoskeletal staining in green using phalloidin, nucleus staining in blue using DAPI.

Figure 18:
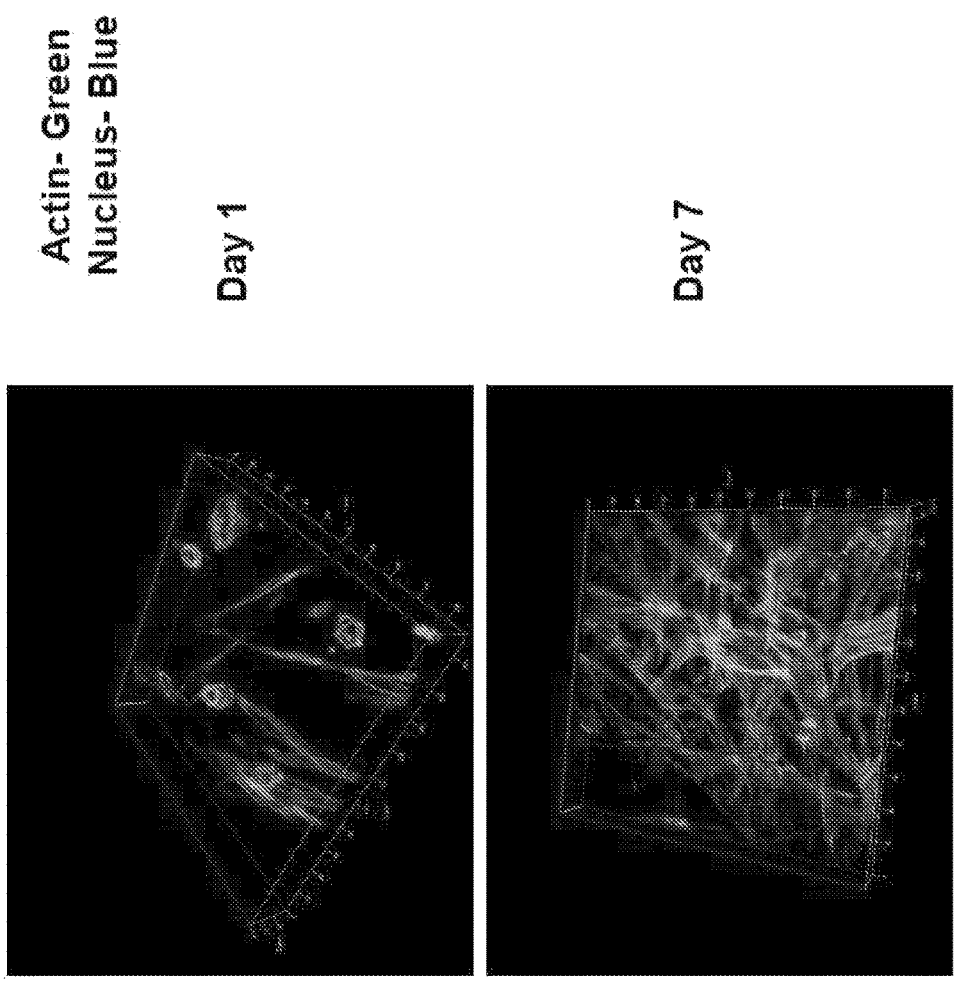

FIG. 18 shows fluorescent images of 3D human dermal fibroblasts embedded IVZK peptide hydrogels (human dermal fibroblast cells—4 million/ml; peptide—10 mg/ml). Actin cytoskeletal staining in green using phalloidin, nucleus staining in blue using DAPI.

Figure 19:
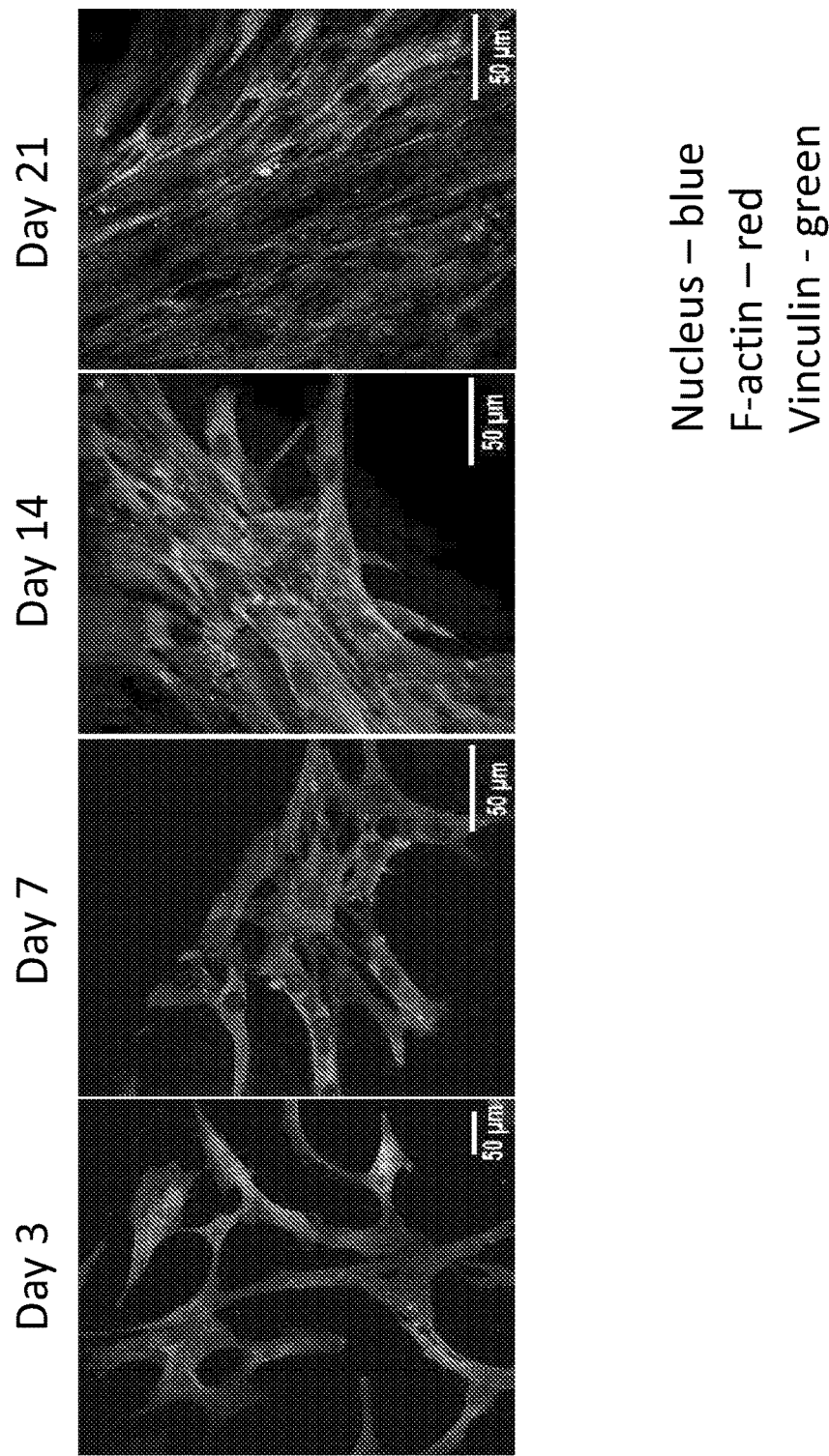

FIG. 19 shows fluorescence confocal microscopy images of 3D bioprinted human bone marrow-derived mesenchymal stem cells (BM-MSCs) cells using IVZK bioink at different days of cell culturing (nucleus is shown in blue, F-actin is shown in red and vinculin is shown in green).

Furthermore, embodiments of the invention are now further described by reference to the following examples which are given to illustrate, not to limit the present invention.

EXAMPLES

Peptide Synthesis

Peptides were manually synthesized using solid phase peptide synthesis and purified to above 95% via HPLC. Amino acid and peptide content analysis were performed. Peptide molecules were synthesized manually using standard solid peptide synthesis on MBHA Rink Amide resin. DCM was used to swell the resin inside the reaction vessel for 30 min. Then, the solvent was removed by applying vacuum to the vessel. The Fmoc-protected group on the resin was removed by treating the resin with 10 mL of 20% (v/v) piperidine/DMF solution for 20 min. DMF and DCM were subsequently used to rinse the resin after each reaction to remove the excess materials from the vessel. Then, amino acid residue solution containing of 3 equivalents of N-protected amino acid, 2.9 equivalents of TBTU and 6 equivalents of DIPEA for each 1 equivalent mol of resin was poured and agitated for at least 2 h. Kaiser Test was performed after each coupling to examine the success of peptide coupling. The Fmoc protected group of the N-terminal peptide sequence was removed by adding 10 mL of 20% (v/v) piperidine/DMF and agitating for 20 min. These sequential steps that were amino acid coupling, washing, Kaiser Test, and Fmoc cleavage were repeated until the last sequence of amino acids. Acetylation was performed by pouring a mixed solution of acetic anhydride, DIPEA, and DMF to the vessel in order to cap the peptide sequence. The peptide sequence was then cleaved from the resin by mixing with acid solution that contained of 95% TFA, 2.5% water, and 2.5% triisopropylsilane for 2 h. The resin then was rinsed only with DCM and collected into the round bottom flask. The removal of excess TFA and DCM from the collected peptide solution was carried out by using rotary evaporation. Diethyl ether was added into the flask to disperse the peptide and kept for overnight. This solution then was centrifuged to separate the solid form of peptide from diethyl ether. The collected white solid was subsequently dissolved in water and freeze-dried to get the fluffy form of peptide. Finally, the peptide was purified by using prep-HPLC before being used.

9-Fluorenylmethoxycarbonyl (Fmoc) protected amino acids, Rink Amide MBHA resin, 2-(1H-benzotriazole-1-yl)-1,1,3,3-tetramethyluronium tetrafluoroborate (TBTU) and 1-hydroxy-7-azabenzotriazole (HOAt) were purchased from GL Biochem. N,N-dimethylformamide (DMF), dichloromethane (DCM), diethyl ether, N,N-diisopropylethylamine (DIPEA), piperidine, and triisopropylsilane were purchased from Sigma-Aldrich. Acetic anhydride, dimethyl sulfoxide (DMSO), acetonitrile were purchased from Fisher Scientific. Trifluoroacetic acid (TFA) were purchased from Acros. The chemicals were used as received, without any purification.

Peptide Hydrogel Preparation

Lyophilized peptides were dissolved in milliQ water and vortexed to get a homogenous solution. Subsequently, 10× phosphate buffered saline at the final concentration of 1× was added to the peptide solution and vortexed shortly. Gelation occurred within few seconds to minutes or hours depending on the peptide sequence.

Rheology Analysis

The mechanical strength of the peptide hydrogels was measured using ARES-G2 rheometer (TA instruments) with an 8 mm parallel plate geometry at 22° C. 150 μL hydrogels were prepared inside a 9.6 mm diameter of polypropylene ring in which the top and bottom of each ring cast was covered with parafilm and kept inside a sealed tissue culture dish for overnight. After loading the hydrogel on peltier plate of the rheometer, water was dropped on the surrounded area to suppress the evaporation of the hydrogel. The gap measurement was adjusted between 1.6 and 1.9 mm. Time sweep measurement was performed prior to frequency sweep and amplitude sweep for 900 s duration with constant strain and angular frequency of 0.1% and 1 rad/s, respectively. The modulus values at the end of time sweep analysis were used as the standard equilibrium modulus for each hydrogel. Oscillatory frequency-sweep analysis were performed with 1% strain for a range of 0.1-100 rad/s. Oscillatory amplitude-sweep measurements were done with the constant angular frequency of 1 rad/s from 0.1 to 100% strain.

Transmission Electron Microscopy (TEM) Studies

Figure 1:
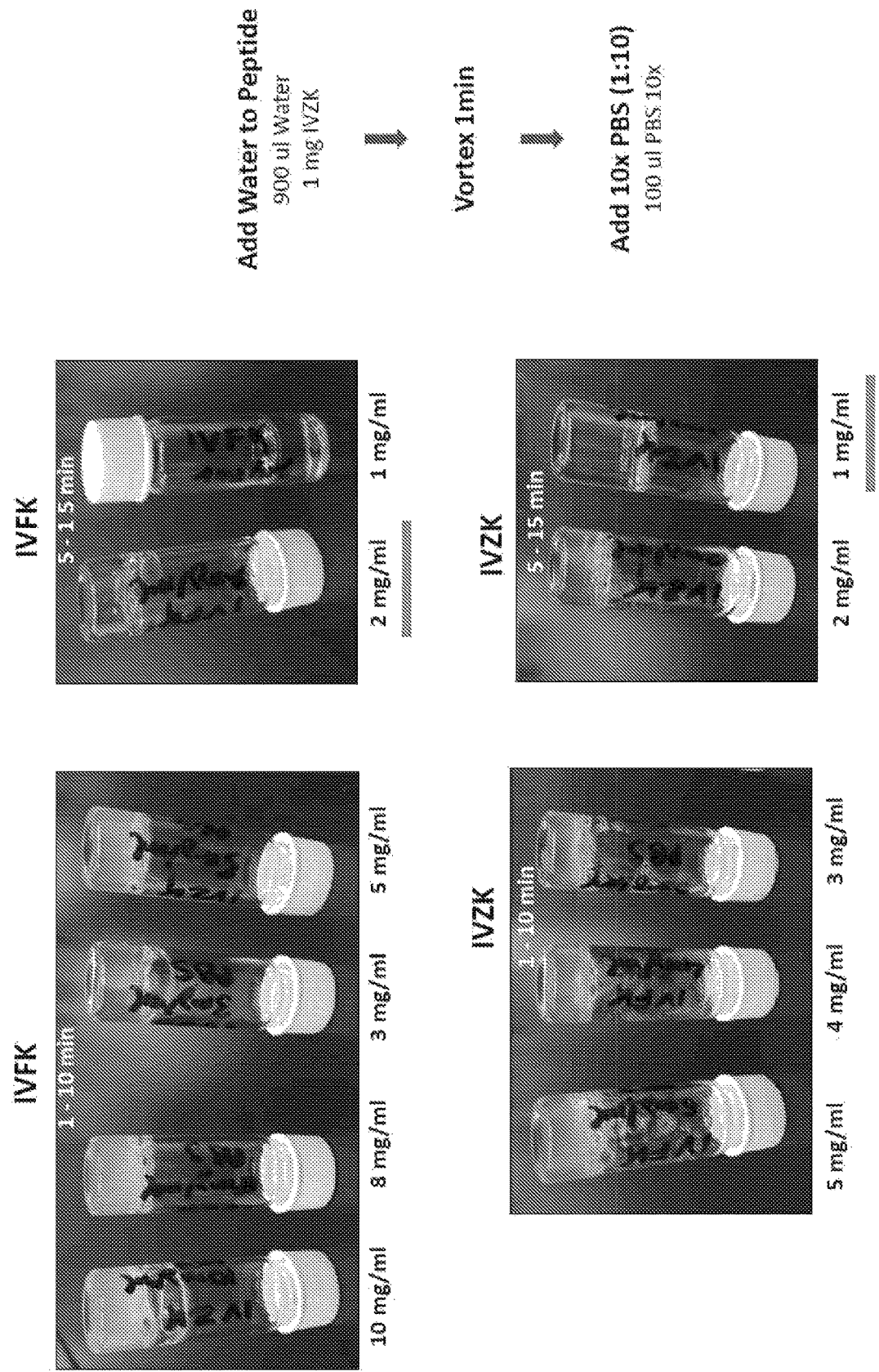
FIG. 1A shows ultrashort peptides IVZK and IVFK self-assemble into macromolecular nanofibrous hydrogels.
FIG. 1B shows the chemical structures of the ultrashort peptides IVZK and IVFK and corresponding hydrogels as well as high resolution transmission electron microscopy (TEM) images.
Figure 1:
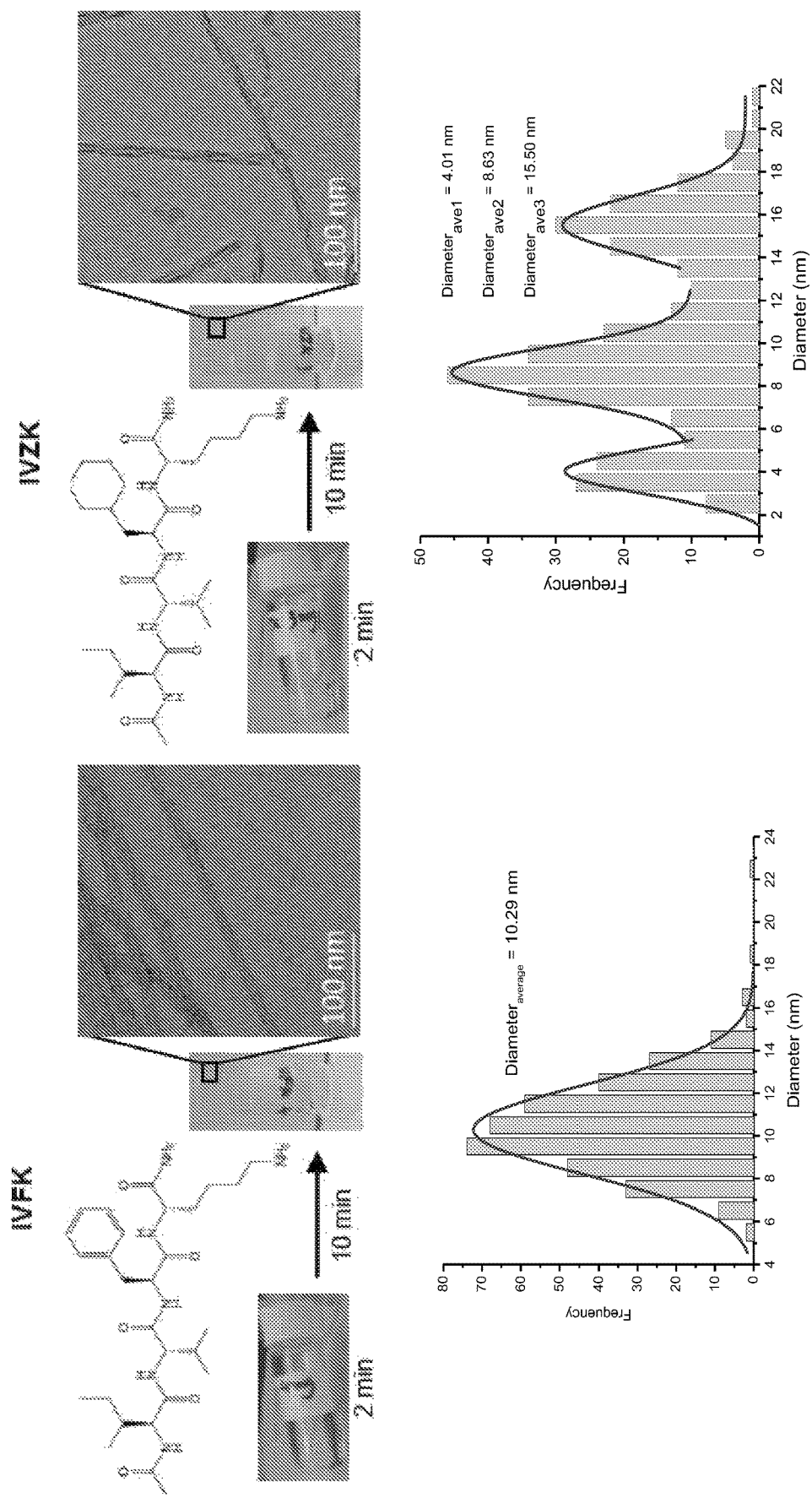

The TEM studies were carried out on two different instruments; Tecnai G2 Spirit Twin with accelerating voltage of 120 kV and FEI Titan G2 80-300 CT with 300 kV emission gun. The Cryo TEM imaging was performed in low dose mode by using FEI's Titan Krios operating at 300 kV. The TEM samples for peptide nanofiber were prepared from diluted peptide hydrogel in water. One drop of this solution was then introduced on a carbon coated copper grid that has been treated with glow discharge plasma before being used. The drop was then kept for 10 minutes before being blotted using filter paper. To get a better contrast, the grid was stained using 2% uranyl acetate for 1 minute and then was dried for at least one day before imaging. The diameter of IVFK and IVZK peptide nanofibers were measured using an image-analysis software ImageJ from 13 and 10 TEM images, respectively. A size distribution histogram for each peptide nanofiber was created in Origin to calculate the average diameter of both peptides. See e.g. FIG. 1B.

FESEM Analysis

Peptide hydrogels were shock frozen in liquid nitrogen and immediately stored at −80° C. overnight. The samples were then vacuum dried in a freeze dryer (Labconco, USA) for 2-3 days. Subsequently, the lyophilized hydrogel samples were fixed onto an aluminium sample holder using conductive carbon tape and sputtered with platinum in a sputter coater. Three rounds of coating were performed at different angles to ensure complete coating. The surface of interest was then examined with a field-emission scanning electron microscope (FEI Nova Nano630 SEM, Oregon, USA) using an accelerating voltage of 5-10 kV or was visualized using FEI Quanta 200 FEG SEM with an accelerating voltage of 2-3 kV. The freeze-dried samples were adhered to carbon conductive tape on SEM stub and sputter coated with 3 nm of Platinum.

Cell Culture

Cells were cultured in medium 106 (Thermo Fisher Scientific, USA) supplemented with 10% fetal bovine serum and 1% penicillin/streptomycin. The cells were maintained either in a T175 or T75 cell culture flask (Corning, USA) at 37° C. in a humidified incubator with 95% air and 5% CO2. The cells were subcultured by trypsination at approximately 80% confluence. The culture media was replenished every 48 hours.

MTT Assay

Biocompatibility studies were carried out in 96-well plates (Corning, USA). HDFn cells (10,000 cells/well) were seeded into a 96-well plate and incubated overnight in 200 μL complete growth medium. After incubation, media in the wells were changed. Peptides were weighed out and dissolved in milliQ water. To test the compatibility, peptides at different concentrations viz 5 mg/mL, 4 mg/mL, 2 mg/mL, 1 mg/mL and 0.5 mg/mL were added to the wells. Untreated wells were used as positive controls. The plates were incubated for 24 hours. Cell viability was determined by means of a colorimetric microculture assay (Vybrant® MTT Cell Proliferation Assay Kit, Thermo Fisher Scientific, USA) according to the manufacturer's protocol. Briefly, the plates were taken, the medium was carefully removed and fresh serum free medium containing 10% MTT reagent was added. After 2 h of incubation at 37° C., the supernatant media was removed and 200 μL of DMSO was added to each wells to dissolve the formazan crystals. Finally, the absorption of individual wells was read at 540 nm using a plate reader (PHERAstar FS, Germany).

Live/Dead Staining

Cells were seeded and treated with peptides according to the protocol described above. After 24 h of incubation, the spent media were removed and replaced with DPBS solution containing approximately 2 mM calcein AM and 4 mM ethidium homodimer-1 (LIVE/DEAD® Viability/Cytotoxicity Kit, Life Technologies™) and incubated for 40 min in dark. Before imaging, the staining solution was removed and fresh DPBS was added. Stained cells were imaged under an inverted confocal microscope (Zeiss LSM 710 Inverted Confocal Microscope, Germany).

Cells (25,000 cells/plate) were embedded in 3D culture with hydrogel in a glass based confocal dish and incubated for 24 h using untreated cells as controls. After 24 h, the medium replaced with PBS (1×) solution containing approximately 2 μM calcein and 4 μM ethidium homodimer-1 (LIVE/DEAD Viability/Cytotoxicity Kit, Molecular Probe, L3224) and incubated for 30 min. Live cells were imaged in the green channel and dead cells in the red channel using ZEISS fluorescence microscope. The obtained pictures were superimposed using ImageJ as shown in FIG. 8.

Cytoskeletal Staining

Immunostaining was performed after 24 h of culture. In brief, the cells were fixed with 3.7% paraformaldehyde solution for 30 minutes and incubated in a cold cytoskeleton buffer (3 mM MgCl2, 300 mM sucrose and 0.5% Triton X-100 in PBS solution) for 10 minutes to permeabilise the cell membranes. The permeabilised cells were incubated in blocking buffer solution (5% FBS, 0.1% Tween-20, and 0.02% sodium azide in PBS) for 30 minutes at 37° C., followed by incubation in antivinculin (1:100) for 1 hour at 37° C. and subsequently with anti-mouse IgG (whole molecule)-FITC and rhodamine-phalloidin (1:200) for 1 hour at 37° C. Further, the cells were incubated in DAPI for 1 hour at 37° C. to counterstain the nucleus. These fluorescent dye treated cells were observed and imaged using laser scanning confocal microscope (Zeiss LSM 710 Inverted Confocal Microscope, Germany).

3D Culture of Cells in Peptide Hydrogels

Cells were encapsulated in peptide hydrogels in 24 well tissue culture plates. Peptide solutions were added to the plate at 200 μL per well. Cells were resuspended in 3×PBS were added to each well at 100,000 cells/well and gently mixed. The final concentration of the peptide hydrogel was 1× after the addition of 3×PBS containing cells. Gelation occurred within 3-5 minutes and subsequently, culture medium was added to the wells. At pre-determined time points, the 3D cell viability assay, live/dead assay and cytoskeletal staining were performed.

3D cell culture was performed by making base on the bottom of plate to make sure that the cells grow in 3D construct, the base was made by pipetting peptide solution (peptide with water) into confocal plate and mixed with (PBS). After gel formation, peptide solution was added on top of this base. Cultured human dermal fibroblasts was trypsinzed, centrifuged and resuspended with PBS (2×) and mixed with peptide solution placed on top of the base. Once the gel form, DMEM was added on top as shown in FIG. 5 and incubate at 37° C. incubator and 5% CO2 for 48 hours and then different biocompatibility assays were applied on this construct.

3D Cell Proliferation Assay

The CellTiter-Glo® luminescent 3D cell viability assay is a method to determine the number of viable cells in 3D hydrogels based on quantification of the ATP present, which signals the presence of metabolically active cells. After each time point, the hydrogels cultured with cells were washed twice with DPBS. Fresh medium was added to each well and equal amount of CellTiter-Glo® luminescent reagent was also added to the gels. The contents were mixed for 2 minutes to digest the hydrogels and then incubated for 10 minutes. After incubation, the luminescence was recorded using a plate reader (PHERAstar FS, Germany).

3D Bioprinting

A 3D bioprinter was used to print constructs using peptide bioinks. To print peptide bioinks, the inventors designed a co-axial needle with three inlets. The top inlet was connected to 10×PBS solution, the right inlet was connected to cells suspended in serum free media and the left inlet was connected to peptide dissolved in milliQ water (15 mg/mL). The tubes, connectors and the co-axial nozzle were autoclaved before printing. While printing, three solutions were pumped into the nozzle with the aid of syringe pumps. The flow rate of peptide solution and cells solution were 25 μL/min while the flow rate of 10×PBS was maintained at 20 μL/min. Peptide solution mix with the cells and 10×PBS at the junction inside the co-axial nozzle just before the exit. Gelation occurs instantaneously and the peptide bioinks were printed. A simple ring structure was bioprinted in a layer-by-layer fashion with a diameter of about 8 mm and thickness about 2 mm. The constructs were printed onto 35-mm tissue culture petri dish. After bioprinting, the constructs were placed in biosafety cabinet for 3 min to further facilitate self-assembly of peptide bioinks. Then, the constructs were gently washed 2 or 3 times with culture medium. To each dish, 3 mL of culture medium was added and cultured in a humidified incubator at 37° C. and 5% CO2. At pre-determined time points, the constructs were taken out to perform 3D assay and cytoskeletal staining of cells as described above.

The peptides according to the present invention are excellent gelators, and the gels formed can be used for many different purposes and applications. The features disclosed in the foregoing description, in the claims or in the accompanying drawings may, both separately and in any combination thereof, be material for realizing the invention in diverse forms thereof.

Further modifications of the preferred embodiments are possible without leaving the scope of the invention which is solely defined by the claims.

The invention claimed is:

1. A peptide capable of forming a gel by self-assembly, wherein the said peptide is selected from the group consisting of IVFD, (SEQ ID NO: 9)
IVOD, (SEQ ID NO: 10)
IVFE, (SEQ ID NO: 17)
IVOE, (SEQ ID NO: 18)
IVFS, (SEQ ID NO: 25)
IVOS, (SEQ ID NO: 26)
IVFR, (SEQ ID NO: 33)
IVOR, (SEQ ID NO: 34)
IVF(Dab), (SEQ ID NO: 41)
IVO(Dab), (SEQ ID NO: 42)
IVF(Dap), (SEQ ID NO: 49)
IVO(Dap), (SEQ ID NO: 50)
IVF(Orn), (SEQ ID NO: 57)
IVO(Orn), (SEQ ID NO: 58)
KFVI, (SEQ ID NO: 65)
KOVI, (SEQ ID NO: 66)
DFVI, (SEQ ID NO: 73)
DOVI, (SEQ ID NO: 74)
EFVI, (SEQ ID NO: 81)
EOVI, (SEQ ID NO: 82)
SFVI, (SEQ ID NO: 89)
SOVI, (SEQ ID NO: 90)
RFVI, (SEQ ID NO: 97)
ROVI, (SEQ ID NO: 98)
(Dab)FVI, (SEQ ID NO: 105)
(Dab)OVI, (SEQ ID NO: 106)
(Dap)FVI, (SEQ ID NO: 113)
(Dap)OVI, (SEQ ID NO: 114)
(Orn)FVI, and (SEQ ID NO: 121)
(Orn)OVI, (SEQ ID NO: 122)

wherein I is isoleucine, L is leucine, V is valine, F is phenylalanine, K is lysine, D is aspartic acid, E is glutamic acid, S is serine, R is arginine, O is cyclohexylalanine, (Dab) is 2,4-diaminobutyric acid, (Dap) is 2,3-diaminopropionic acid, and (Orn) is ornithine.

2. The peptide according to claim 1, being stable in aqueous solution at physiological conditions at ambient temperature for at least 6 months and/or being stable in aqueous solution at physiological conditions, at a temperature up to 90° C., for at least 1 hour.

3. A hydrogel or organogel comprising the peptide of claim 1.

4. The hydrogel or organogel according to claim 3, wherein:
the hydrogel is stable in aqueous solution at ambient temperature for at least 1 month, the hydrogel is characterized by a storage modulus G' to loss modulus G" ratio that is greater than 2 to 5,
the hydrogel or organogel is characterized by a storage modulus G' from 500 Pa to 200,000 Pa at a frequency in the range of from 0.1 Hz to 100 Hz, and/or
the hydrogel or organogel is characterized by a storage modulus G' from 500 Pa to 200,000 Pa at a frequency in the range of from 0.1 Hz to 100 Hz.

5. The hydrogel or organogel according to claim 3, wherein the hydrogel or organogel has a higher mechanical strength than collagen or its hydrolyzed form (gelatin).

6. The hydrogel or organogel according to claim 3, wherein the hydrogel or organogel is comprised in at least one of a fuel cell, a solar cell, an electronic cell, a biosensing device, a medical device, an implant, a pharmaceutical composition and a cosmetic composition.

7. The hydrogel or organogel according to claim 3, which is injectable.

8. A method of preparing a hydrogel or organogel, the method comprising dissolving a peptide according to claim 1 in an aqueous solution or an organic solution, respectively.

9. The method of claim 8, wherein the dissolved peptide in aqueous or organic solution is further exposed to temperature, wherein the temperature is in the range from 20° C. to 90° C. and/or wherein the peptide is dissolved at a concentration from about 1 mg/ml to about 20 mg/ml.

10. A kit of parts, the kit comprising a first container with a peptide according to claim 1 and a second container with an aqueous or organic solution.

11. A peptide capable of forming a gel by self-assembly, said peptide having a sequence selected from the group consisting of:

```
                                         (SEQ ID NO: 1)
            IVFK, and (SEQ ID NO: 2)
            IVOK,
``` wherein I=isoleucine, V=valine, F=phenylalanine, K=lysine, and O=cyclohexylalanine.

* * * * *

SEQUENCE LISTING

```
<160> NUMBER OF SEQ ID NOS: 128

<210> SEQ ID NO 1
<211> LENGTH: 4
<212> TYPE: PRT
<213> ORGANISM: Artificial Sequence
<220> FEATURE:
<223> OTHER INFORMATION: Peptide capable of forming a gel by self-
      assembly
```

```
<400> SEQUENCE: 1

Ile Val Phe Lys
1

<210> SEQ ID NO 2
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa is O = cyclohexylalanine
<220> FEATURE:
<221> NAME/KEY: misc_feature
<222> LOCATION: (3)..(3)
<223> OTHER INFORMATION: Xaa can be any naturally occurring amino acid

<400> SEQUENCE: 2

Ile Val Xaa Lys
1

<210> SEQ ID NO 3
<211> LENGTH: 4
<212> TYPE: PRT
<213> ORGANISM: Artificial Sequence
<220> FEATURE:
<223> OTHER INFORMATION: Peptide capable of forming a gel by self-
      assembly

<400> SEQUENCE: 3

Ile Phe Val Lys
1

<210> SEQ ID NO 4
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa is O = cyclohexylalanine
<220> FEATURE:
<221> NAME/KEY: misc_feature
<222> LOCATION: (2)..(2)
<223> OTHER INFORMATION: Xaa can be any naturally occurring amino acid

<400> SEQUENCE: 4

Ile Xaa Val Lys
1

<210> SEQ ID NO 5
<211> LENGTH: 4
<212> TYPE: PRT
<213> ORGANISM: Artificial Sequence
<220> FEATURE:
<223> OTHER INFORMATION: Peptide capable of forming a gel by self-
      assembly

<400> SEQUENCE: 5

Phe Ile Val Lys
1

<210> SEQ ID NO 6
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa is O = cyclohexylalanine
<220> FEATURE:
<221> NAME/KEY: misc_feature
```

```
<222> LOCATION: (1)..(1)
<223> OTHER INFORMATION: Xaa can be any naturally occurring amino acid

<400> SEQUENCE: 6

Xaa Ile Val Lys
1

<210> SEQ ID NO 7
<211> LENGTH: 4
<212> TYPE: PRT
<213> ORGANISM: Artificial Sequence
<220> FEATURE:
<223> OTHER INFORMATION: Peptide capable of forming a gel by self-
      assembly

<400> SEQUENCE: 7

Phe Val Ile Lys
1

<210> SEQ ID NO 8
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa is O = cyclohexylalanine
<220> FEATURE:
<221> NAME/KEY: misc_feature
<222> LOCATION: (1)..(1)
<223> OTHER INFORMATION: Xaa can be any naturally occurring amino acid

<400> SEQUENCE: 8

Xaa Val Ile Lys
1

<210> SEQ ID NO 9
<211> LENGTH: 4
<212> TYPE: PRT
<213> ORGANISM: Artificial Sequence
<220> FEATURE:
<223> OTHER INFORMATION: Peptide capable of forming a gel by self-
      assembly

<400> SEQUENCE: 9

Ile Val Phe Asp
1

<210> SEQ ID NO 10
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa is O = cyclohexylalanine
<220> FEATURE:
<221> NAME/KEY: misc_feature
<222> LOCATION: (3)..(3)
<223> OTHER INFORMATION: Xaa can be any naturally occurring amino acid

<400> SEQUENCE: 10

Ile Val Xaa Asp
1

<210> SEQ ID NO 11
<211> LENGTH: 4
<212> TYPE: PRT
<213> ORGANISM: Artificial Sequence
<220> FEATURE:
<223> OTHER INFORMATION: Peptide capable of forming a gel by self-
```

```
            assembly

<400> SEQUENCE: 11

Ile Phe Val Asp
1

<210> SEQ ID NO 12
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa is O = cyclohexylalanine
<220> FEATURE:
<221> NAME/KEY: misc_feature
<222> LOCATION: (2)..(2)
<223> OTHER INFORMATION: Xaa can be any naturally occurring amino acid

<400> SEQUENCE: 12

Ile Xaa Val Asp
1

<210> SEQ ID NO 13
<211> LENGTH: 4
<212> TYPE: PRT
<213> ORGANISM: Artificial Sequence
<220> FEATURE:
<223> OTHER INFORMATION: Peptide capable of forming a gel by self-
      assembly

<400> SEQUENCE: 13

Phe Ile Val Asp
1

<210> SEQ ID NO 14
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa is O = cyclohexylalanine
<220> FEATURE:
<221> NAME/KEY: misc_feature
<222> LOCATION: (1)..(1)
<223> OTHER INFORMATION: Xaa can be any naturally occurring amino acid

<400> SEQUENCE: 14

Xaa Ile Val Asp
1

<210> SEQ ID NO 15
<211> LENGTH: 4
<212> TYPE: PRT
<213> ORGANISM: Artificial Sequence
<220> FEATURE:
<223> OTHER INFORMATION: Peptide capable of forming a gel by self-
      assembly

<400> SEQUENCE: 15

Phe Val Ile Asp
1

<210> SEQ ID NO 16
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa is O = cyclohexylalanine
```

```
<220> FEATURE:
<221> NAME/KEY: misc_feature
<222> LOCATION: (1)..(1)
<223> OTHER INFORMATION: Xaa can be any naturally occurring amino acid

<400> SEQUENCE: 16

Xaa Val Ile Asp
1

<210> SEQ ID NO 17
<211> LENGTH: 4
<212> TYPE: PRT
<213> ORGANISM: Artificial Sequence
<220> FEATURE:
<223> OTHER INFORMATION: Peptide capable of forming a gel by self-
      assembly

<400> SEQUENCE: 17

Ile Val Phe Glu
1

<210> SEQ ID NO 18
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa is O = cyclohexylalanine
<220> FEATURE:
<221> NAME/KEY: misc_feature
<222> LOCATION: (3)..(3)
<223> OTHER INFORMATION: Xaa can be any naturally occurring amino acid

<400> SEQUENCE: 18

Ile Val Xaa Glu
1

<210> SEQ ID NO 19
<211> LENGTH: 4
<212> TYPE: PRT
<213> ORGANISM: Artificial Sequence
<220> FEATURE:
<223> OTHER INFORMATION: Peptide capable of forming a gel by self-
      assembly

<400> SEQUENCE: 19

Ile Phe Val Glu
1

<210> SEQ ID NO 20
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa is O = cyclohexylalanine
<220> FEATURE:
<221> NAME/KEY: misc_feature
<222> LOCATION: (2)..(2)
<223> OTHER INFORMATION: Xaa can be any naturally occurring amino acid

<400> SEQUENCE: 20

Ile Xaa Val Glu
1

<210> SEQ ID NO 21
<211> LENGTH: 4
<212> TYPE: PRT
<213> ORGANISM: Artificial Sequence
```

```
<220> FEATURE:
<223> OTHER INFORMATION: Peptide capable of forming a gel by self-
      assembly

<400> SEQUENCE: 21

Phe Ile Val Glu
1

<210> SEQ ID NO 22
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa is O = cyclohexylalanine
<220> FEATURE:
<221> NAME/KEY: misc_feature
<222> LOCATION: (1)..(1)
<223> OTHER INFORMATION: Xaa can be any naturally occurring amino acid

<400> SEQUENCE: 22

Xaa Ile Val Glu
1

<210> SEQ ID NO 23
<211> LENGTH: 4
<212> TYPE: PRT
<213> ORGANISM: Artificial Sequence
<220> FEATURE:
<223> OTHER INFORMATION: Peptide capable of forming a gel by self-
      assembly

<400> SEQUENCE: 23

Phe Val Ile Glu
1

<210> SEQ ID NO 24
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa is O = cyclohexylalanine
<220> FEATURE:
<221> NAME/KEY: misc_feature
<222> LOCATION: (1)..(1)
<223> OTHER INFORMATION: Xaa can be any naturally occurring amino acid

<400> SEQUENCE: 24

Xaa Val Ile Glu
1

<210> SEQ ID NO 25
<211> LENGTH: 4
<212> TYPE: PRT
<213> ORGANISM: Artificial Sequence
<220> FEATURE:
<223> OTHER INFORMATION: Peptide capable of forming a gel by self-
      assembly

<400> SEQUENCE: 25

Ile Val Phe Ser
1

<210> SEQ ID NO 26
<211> LENGTH: 4
<212> TYPE: PRT
<213> ORGANISM: Artificial Sequence
<220> FEATURE:
```

<223> OTHER INFORMATION: Peptide capable of forming a gel by self-
      assembly, X or Xaa is O = cyclohexylalanine
<220> FEATURE:
<221> NAME/KEY: misc_feature
<222> LOCATION: (3)..(3)
<223> OTHER INFORMATION: Xaa can be any naturally occurring amino acid

<400> SEQUENCE: 26

Ile Val Xaa Ser
1

<210> SEQ ID NO 27
<211> LENGTH: 4
<212> TYPE: PRT
<213> ORGANISM: Artificial Sequence
<220> FEATURE:
<223> OTHER INFORMATION: Peptide capable of forming a gel by self-
      assembly

<400> SEQUENCE: 27

Ile Phe Val Ser
1

<210> SEQ ID NO 28
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa is O = cyclohexylalanine
<220> FEATURE:
<221> NAME/KEY: misc_feature
<222> LOCATION: (2)..(2)
<223> OTHER INFORMATION: Xaa can be any naturally occurring amino acid

<400> SEQUENCE: 28

Ile Xaa Val Ser
1

<210> SEQ ID NO 29
<211> LENGTH: 4
<212> TYPE: PRT
<213> ORGANISM: Artificial Sequence
<220> FEATURE:
<223> OTHER INFORMATION: Peptide capable of forming a gel by self-
      assembly

<400> SEQUENCE: 29

Phe Ile Val Ser
1

<210> SEQ ID NO 30
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa is O = cyclohexylalanine
<220> FEATURE:
<221> NAME/KEY: misc_feature
<222> LOCATION: (1)..(1)
<223> OTHER INFORMATION: Xaa can be any naturally occurring amino acid

<400> SEQUENCE: 30

Xaa Ile Val Ser
1

<210> SEQ ID NO 31
<211> LENGTH: 4

```
<212> TYPE: PRT
<213> ORGANISM: Artificial Sequence
<220> FEATURE:
<223> OTHER INFORMATION: Peptide capable of forming a gel by self-
      assembly

<400> SEQUENCE: 31

Phe Val Ile Ser
1

<210> SEQ ID NO 32
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa is O = cyclohexylalanine
<220> FEATURE:
<221> NAME/KEY: misc_feature
<222> LOCATION: (1)..(1)
<223> OTHER INFORMATION: Xaa can be any naturally occurring amino acid

<400> SEQUENCE: 32

Xaa Val Ile Ser
1

<210> SEQ ID NO 33
<211> LENGTH: 4
<212> TYPE: PRT
<213> ORGANISM: Artificial Sequence
<220> FEATURE:
<223> OTHER INFORMATION: Peptide capable of forming a gel by self-
      assembly

<400> SEQUENCE: 33

Ile Val Phe Arg
1

<210> SEQ ID NO 34
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa is O = cyclohexylalanine
<220> FEATURE:
<221> NAME/KEY: misc_feature
<222> LOCATION: (3)..(3)
<223> OTHER INFORMATION: Xaa can be any naturally occurring amino acid

<400> SEQUENCE: 34

Ile Val Xaa Arg
1

<210> SEQ ID NO 35
<211> LENGTH: 4
<212> TYPE: PRT
<213> ORGANISM: Artificial Sequence
<220> FEATURE:
<223> OTHER INFORMATION: Peptide capable of forming a gel by self-
      assembly

<400> SEQUENCE: 35

Ile Phe Val Arg
1

<210> SEQ ID NO 36
<211> LENGTH: 4
<212> TYPE: PRT
```

```
<213> ORGANISM: Artificial Sequence
<220> FEATURE:
<223> OTHER INFORMATION: Peptide capable of forming a gel by self-
      assembly, X or Xaa is O = cyclohexylalanine
<220> FEATURE:
<221> NAME/KEY: misc_feature
<222> LOCATION: (2)..(2)
<223> OTHER INFORMATION: Xaa can be any naturally occurring amino acid

<400> SEQUENCE: 36

Ile Xaa Val Arg
1

<210> SEQ ID NO 37
<211> LENGTH: 4
<212> TYPE: PRT
<213> ORGANISM: Artificial Sequence
<220> FEATURE:
<223> OTHER INFORMATION: Peptide capable of forming a gel by self-
      assembly

<400> SEQUENCE: 37

Phe Ile Val Arg
1

<210> SEQ ID NO 38
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa is O = cyclohexylalanine
<220> FEATURE:
<221> NAME/KEY: misc_feature
<222> LOCATION: (1)..(1)
<223> OTHER INFORMATION: Xaa can be any naturally occurring amino acid

<400> SEQUENCE: 38

Xaa Ile Val Arg
1

<210> SEQ ID NO 39
<211> LENGTH: 4
<212> TYPE: PRT
<213> ORGANISM: Artificial Sequence
<220> FEATURE:
<223> OTHER INFORMATION: Peptide capable of forming a gel by self-
      assembly

<400> SEQUENCE: 39

Phe Val Ile Arg
1

<210> SEQ ID NO 40
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa is O = cyclohexylalanine
<220> FEATURE:
<221> NAME/KEY: misc_feature
<222> LOCATION: (1)..(1)
<223> OTHER INFORMATION: Xaa can be any naturally occurring amino acid

<400> SEQUENCE: 40

Xaa Val Ile Arg
1
```

```
<210> SEQ ID NO 41
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein C-terminal X or Xaa = Dbu
<220> FEATURE:
<221> NAME/KEY: misc_feature
<222> LOCATION: (4)..(4)
<223> OTHER INFORMATION: Xaa can be any naturally occurring amino acid

<400> SEQUENCE: 41

Ile Val Phe Xaa
1

<210> SEQ ID NO 42
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein C-terminal X or Xaa = Dbu and the other X or
      Xaa = cyclohexylalanine
<220> FEATURE:
<221> NAME/KEY: misc_feature
<222> LOCATION: (3)..(4)
<223> OTHER INFORMATION: Xaa can be any naturally occurring amino acid

<400> SEQUENCE: 42

Ile Val Xaa Xaa
1

<210> SEQ ID NO 43
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein C-terminal X or Xaa = Dbu
<220> FEATURE:
<221> NAME/KEY: misc_feature
<222> LOCATION: (4)..(4)
<223> OTHER INFORMATION: Xaa can be any naturally occurring amino acid

<400> SEQUENCE: 43

Ile Phe Val Xaa
1

<210> SEQ ID NO 44
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein C-terminal X or Xaa = Dbu and the other X or
      Xaa = cyclohexylalanine
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 44

Ile Xaa Val Xaa
1

<210> SEQ ID NO 45
```

-continued

```
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein C-terminal X or Xaa = Dbu
<220> FEATURE:
<221> NAME/KEY: misc_feature
<222> LOCATION: (4)..(4)
<223> OTHER INFORMATION: Xaa can be any naturally occurring amino acid

<400> SEQUENCE: 45

Phe Ile Val Xaa
1

<210> SEQ ID NO 46
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein C-terminal X or Xaa = Dbu and the other X or
      Xaa = cyclohexylalanine
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 46

Xaa Ile Val Xaa
1

<210> SEQ ID NO 47
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein C-terminal  X or Xaa = Dbu
<220> FEATURE:
<221> NAME/KEY: misc_feature
<222> LOCATION: (4)..(4)
<223> OTHER INFORMATION: Xaa can be any naturally occurring amino acid

<400> SEQUENCE: 47

Phe Val Ile Xaa
1

<210> SEQ ID NO 48
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein C-terminal X or Xaa = Dbu and the other X or
      Xaa = cyclohexylalanine
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 48

Xaa Val Ile Xaa
1
```

```
<210> SEQ ID NO 49
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein C-terminal X or Xaa = Dpr
<220> FEATURE:
<221> NAME/KEY: misc_feature
<222> LOCATION: (4)..(4)
<223> OTHER INFORMATION: Xaa can be any naturally occurring amino acid

<400> SEQUENCE: 49

Ile Val Phe Xaa
1

<210> SEQ ID NO 50
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein C-terminal X or Xaa = Dpr and the other X or
      Xaa = cyclohexylalanine
<220> FEATURE:
<221> NAME/KEY: misc_feature
<222> LOCATION: (3)..(4)
<223> OTHER INFORMATION: Xaa can be any naturally occurring amino acid

<400> SEQUENCE: 50

Ile Val Xaa Xaa
1

<210> SEQ ID NO 51
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein C-terminal X or Xaa = Dpr
<220> FEATURE:
<221> NAME/KEY: misc_feature
<222> LOCATION: (4)..(4)
<223> OTHER INFORMATION: Xaa can be any naturally occurring amino acid

<400> SEQUENCE: 51

Ile Phe Val Xaa
1

<210> SEQ ID NO 52
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein C-terminal X or Xaa = Dpr and the other X or
      Xaa = cyclohexylalanine
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 52

Ile Xaa Val Xaa
1
```

```
<210> SEQ ID NO 53
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein C-terminal X or Xaa = Dpr
<220> FEATURE:
<221> NAME/KEY: misc_feature
<222> LOCATION: (4)..(4)
<223> OTHER INFORMATION: Xaa can be any naturally occurring amino acid

<400> SEQUENCE: 53

Phe Ile Val Xaa
1

<210> SEQ ID NO 54
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein C-terminal X or Xaa = Dpr and the other X or
      Xaa = cyclohexylalanine
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 54

Xaa Ile Val Xaa
1

<210> SEQ ID NO 55
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein C-terminal X or Xaa = Dpr
<220> FEATURE:
<221> NAME/KEY: misc_feature
<222> LOCATION: (4)..(4)
<223> OTHER INFORMATION: Xaa can be any naturally occurring amino acid

<400> SEQUENCE: 55

Phe Val Ile Xaa
1

<210> SEQ ID NO 56
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein C-terminal X or Xaa = Dpr and the other X or
      Xaa = cyclohexylalanine
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 56
```

```
Xaa Val Ile Xaa
1

<210> SEQ ID NO 57
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein C-terminal X or Xaa = Orn
<220> FEATURE:
<221> NAME/KEY: misc_feature
<222> LOCATION: (4)..(4)
<223> OTHER INFORMATION: Xaa can be any naturally occurring amino acid

<400> SEQUENCE: 57

Ile Val Phe Xaa
1

<210> SEQ ID NO 58
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein C-terminal X or Xaa = Orn and the other X or
      Xaa = cyclohexylalanine
<220> FEATURE:
<221> NAME/KEY: misc_feature
<222> LOCATION: (3)..(4)
<223> OTHER INFORMATION: Xaa can be any naturally occurring amino acid

<400> SEQUENCE: 58

Ile Val Xaa Xaa
1

<210> SEQ ID NO 59
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein C-terminal X or Xaa = Orn
<220> FEATURE:
<221> NAME/KEY: misc_feature
<222> LOCATION: (4)..(4)
<223> OTHER INFORMATION: Xaa can be any naturally occurring amino acid

<400> SEQUENCE: 59

Ile Phe Val Xaa
1

<210> SEQ ID NO 60
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein C-terminal X or Xaa = Orn and the other X or
      Xaa = cyclohexylalanine
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 60

Ile Xaa Val Xaa
```

<210> SEQ ID NO 61
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein C-terminal X or Xaa = Orn
<220> FEATURE:
<221> NAME/KEY: misc_feature
<222> LOCATION: (4)..(4)
<223> OTHER INFORMATION: Xaa can be any naturally occurring amino acid

<400> SEQUENCE: 61

Phe Ile Val Xaa
1

<210> SEQ ID NO 62
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein C-terminal X or Xaa = Orn and the other X or
      Xaa = cyclohexylalanine
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 62

Xaa Ile Val Xaa
1

<210> SEQ ID NO 63
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein C-terminal X or Xaa = Orn
<220> FEATURE:
<221> NAME/KEY: misc_feature
<222> LOCATION: (4)..(4)
<223> OTHER INFORMATION: Xaa can be any naturally occurring amino acid

<400> SEQUENCE: 63

Phe Val Ile Xaa
1

<210> SEQ ID NO 64
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein C-terminal X or Xaa = Orn and the other X or
      Xaa = cyclohexylalanine
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid -continued

```
<400> SEQUENCE: 64

Xaa Val Ile Xaa
1

<210> SEQ ID NO 65
<211> LENGTH: 4
<212> TYPE: PRT
<213> ORGANISM: Artificial Sequence
<220> FEATURE:
<223> OTHER INFORMATION: Peptide capable of forming a gel by self-
      assembly

<400> SEQUENCE: 65

Lys Phe Val Ile
1

<210> SEQ ID NO 66
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa = cyclohexylalanine
<220> FEATURE:
<221> NAME/KEY: misc_feature
<222> LOCATION: (2)..(2)
<223> OTHER INFORMATION: Xaa can be any naturally occurring amino acid

<400> SEQUENCE: 66

Lys Xaa Val Ile
1

<210> SEQ ID NO 67
<211> LENGTH: 4
<212> TYPE: PRT
<213> ORGANISM: Artificial Sequence
<220> FEATURE:
<223> OTHER INFORMATION: Peptide capable of forming a gel by self-
      assembly

<400> SEQUENCE: 67

Lys Val Phe Ile
1

<210> SEQ ID NO 68
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa = cyclohexylalanine
<220> FEATURE:
<221> NAME/KEY: misc_feature
<222> LOCATION: (3)..(3)
<223> OTHER INFORMATION: Xaa can be any naturally occurring amino acid

<400> SEQUENCE: 68

Lys Val Xaa Ile
1

<210> SEQ ID NO 69
<211> LENGTH: 4
<212> TYPE: PRT
<213> ORGANISM: Artificial Sequence
<220> FEATURE:
<223> OTHER INFORMATION: Peptide capable of forming a gel by self-
      assembly

<400> SEQUENCE: 69
```

Lys Val Ile Phe
1

<210> SEQ ID NO 70
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa = cyclohexylalanine
<220> FEATURE:
<221> NAME/KEY: misc_feature
<222> LOCATION: (4)..(4)
<223> OTHER INFORMATION: Xaa can be any naturally occurring amino acid

<400> SEQUENCE: 70

Lys Val Ile Xaa
1

<210> SEQ ID NO 71
<211> LENGTH: 4
<212> TYPE: PRT
<213> ORGANISM: Artificial Sequence
<220> FEATURE:
<223> OTHER INFORMATION: Peptide capable of forming a gel by self-
      assembly

<400> SEQUENCE: 71

Lys Ile Val Phe
1

<210> SEQ ID NO 72
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa = cyclohexylalanine
<220> FEATURE:
<221> NAME/KEY: misc_feature
<222> LOCATION: (4)..(4)
<223> OTHER INFORMATION: Xaa can be any naturally occurring amino acid

<400> SEQUENCE: 72

Lys Ile Val Xaa
1

<210> SEQ ID NO 73
<211> LENGTH: 4
<212> TYPE: PRT
<213> ORGANISM: Artificial Sequence
<220> FEATURE:
<223> OTHER INFORMATION: Peptide capable of forming a gel by self-
      assembly

<400> SEQUENCE: 73

Asp Phe Val Ile
1

<210> SEQ ID NO 74
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa = cyclohexylalanine
<220> FEATURE:
<221> NAME/KEY: misc_feature
<222> LOCATION: (2)..(2)

```
<223> OTHER INFORMATION: Xaa can be any naturally occurring amino acid

<400> SEQUENCE: 74

Asp Xaa Val Ile
1

<210> SEQ ID NO 75
<211> LENGTH: 4
<212> TYPE: PRT
<213> ORGANISM: Artificial Sequence
<220> FEATURE:
<223> OTHER INFORMATION: Peptide capable of forming a gel by self-
      assembly

<400> SEQUENCE: 75

Asp Val Phe Ile
1

<210> SEQ ID NO 76
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa = cyclohexylalanine
<220> FEATURE:
<221> NAME/KEY: misc_feature
<222> LOCATION: (3)..(3)
<223> OTHER INFORMATION: Xaa can be any naturally occurring amino acid

<400> SEQUENCE: 76

Asp Val Xaa Ile
1

<210> SEQ ID NO 77
<211> LENGTH: 4
<212> TYPE: PRT
<213> ORGANISM: Artificial Sequence
<220> FEATURE:
<223> OTHER INFORMATION: Peptide capable of forming a gel by self-
      assembly

<400> SEQUENCE: 77

Asp Val Ile Phe
1

<210> SEQ ID NO 78
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa = cyclohexylalanine
<220> FEATURE:
<221> NAME/KEY: misc_feature
<222> LOCATION: (4)..(4)
<223> OTHER INFORMATION: Xaa can be any naturally occurring amino acid

<400> SEQUENCE: 78

Asp Val Ile Xaa
1

<210> SEQ ID NO 79
<211> LENGTH: 4
<212> TYPE: PRT
<213> ORGANISM: Artificial Sequence
<220> FEATURE:
<223> OTHER INFORMATION: Peptide capable of forming a gel by self-
      assembly
```

<400> SEQUENCE: 79

Asp Ile Val Phe
1

<210> SEQ ID NO 80
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa = cyclohexylalanine
<220> FEATURE:
<221> NAME/KEY: misc_feature
<222> LOCATION: (4)..(4)
<223> OTHER INFORMATION: Xaa can be any naturally occurring amino acid

<400> SEQUENCE: 80

Asp Ile Val Xaa
1

<210> SEQ ID NO 81
<211> LENGTH: 4
<212> TYPE: PRT
<213> ORGANISM: Artificial Sequence
<220> FEATURE:
<223> OTHER INFORMATION: Peptide capable of forming a gel by self-
      assembly

<400> SEQUENCE: 81

Glu Phe Val Ile
1

<210> SEQ ID NO 82
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa = cyclohexylalanine
<220> FEATURE:
<221> NAME/KEY: misc_feature
<222> LOCATION: (2)..(2)
<223> OTHER INFORMATION: Xaa can be any naturally occurring amino acid

<400> SEQUENCE: 82

Glu Xaa Val Ile
1

<210> SEQ ID NO 83
<211> LENGTH: 4
<212> TYPE: PRT
<213> ORGANISM: Artificial Sequence
<220> FEATURE:
<223> OTHER INFORMATION: Peptide capable of forming a gel by self-
      assembly

<400> SEQUENCE: 83

Glu Val Phe Ile
1

<210> SEQ ID NO 84
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa = cyclohexylalanine
<220> FEATURE:

```
<221> NAME/KEY: misc_feature
<222> LOCATION: (3)..(3)
<223> OTHER INFORMATION: Xaa can be any naturally occurring amino acid

<400> SEQUENCE: 84

Glu Val Xaa Ile
1

<210> SEQ ID NO 85
<211> LENGTH: 4
<212> TYPE: PRT
<213> ORGANISM: Artificial Sequence
<220> FEATURE:
<223> OTHER INFORMATION: Peptide capable of forming a gel by self-
      assembly

<400> SEQUENCE: 85

Glu Val Ile Phe
1

<210> SEQ ID NO 86
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa = cyclohexylalanine
<220> FEATURE:
<221> NAME/KEY: misc_feature
<222> LOCATION: (4)..(4)
<223> OTHER INFORMATION: Xaa can be any naturally occurring amino acid

<400> SEQUENCE: 86

Glu Val Ile Xaa
1

<210> SEQ ID NO 87
<211> LENGTH: 4
<212> TYPE: PRT
<213> ORGANISM: Artificial Sequence
<220> FEATURE:
<223> OTHER INFORMATION: Peptide capable of forming a gel by self-
      assembly

<400> SEQUENCE: 87

Glu Ile Val Phe
1

<210> SEQ ID NO 88
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa = cyclohexylalanine
<220> FEATURE:
<221> NAME/KEY: misc_feature
<222> LOCATION: (4)..(4)
<223> OTHER INFORMATION: Xaa can be any naturally occurring amino acid

<400> SEQUENCE: 88

Glu Ile Val Xaa
1

<210> SEQ ID NO 89
<211> LENGTH: 4
<212> TYPE: PRT
<213> ORGANISM: Artificial Sequence
<220> FEATURE:
```

```
<223> OTHER INFORMATION: Peptide capable of forming a gel by self-
      assembly

<400> SEQUENCE: 89

Ser Phe Val Ile
1

<210> SEQ ID NO 90
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa = cyclohexylalanine
<220> FEATURE:
<221> NAME/KEY: misc_feature
<222> LOCATION: (2)..(2)
<223> OTHER INFORMATION: Xaa can be any naturally occurring amino acid

<400> SEQUENCE: 90

Ser Xaa Val Ile
1

<210> SEQ ID NO 91
<211> LENGTH: 4
<212> TYPE: PRT
<213> ORGANISM: Artificial Sequence
<220> FEATURE:
<223> OTHER INFORMATION: Peptide capable of forming a gel by self-
      assembly

<400> SEQUENCE: 91

Ser Val Phe Ile
1

<210> SEQ ID NO 92
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa = cyclohexylalanine
<220> FEATURE:
<221> NAME/KEY: misc_feature
<222> LOCATION: (3)..(3)
<223> OTHER INFORMATION: Xaa can be any naturally occurring amino acid

<400> SEQUENCE: 92

Ser Val Xaa Ile
1

<210> SEQ ID NO 93
<211> LENGTH: 4
<212> TYPE: PRT
<213> ORGANISM: Artificial Sequence
<220> FEATURE:
<223> OTHER INFORMATION: Peptide capable of forming a gel by self-
      assembly

<400> SEQUENCE: 93

Ser Val Ile Phe
1

<210> SEQ ID NO 94
<211> LENGTH: 4
<212> TYPE: PRT
<213> ORGANISM: Artificial Sequence
<220> FEATURE:
<223> OTHER INFORMATION: Peptide capable of forming a gel by self-
```

```
      assembly, X or Xaa = cyclohexylalanine
<220> FEATURE:
<221> NAME/KEY: misc_feature
<222> LOCATION: (4)..(4)
<223> OTHER INFORMATION: Xaa can be any naturally occurring amino acid

<400> SEQUENCE: 94

Ser Val Ile Xaa
1

<210> SEQ ID NO 95
<211> LENGTH: 4
<212> TYPE: PRT
<213> ORGANISM: Artificial Sequence
<220> FEATURE:
<223> OTHER INFORMATION: Peptide capable of forming a gel by self-
      assembly

<400> SEQUENCE: 95

Ser Ile Val Phe
1

<210> SEQ ID NO 96
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa = cyclohexylalanine
<220> FEATURE:
<221> NAME/KEY: misc_feature
<222> LOCATION: (4)..(4)
<223> OTHER INFORMATION: Xaa can be any naturally occurring amino acid

<400> SEQUENCE: 96

Ser Ile Val Xaa
1

<210> SEQ ID NO 97
<211> LENGTH: 4
<212> TYPE: PRT
<213> ORGANISM: Artificial Sequence
<220> FEATURE:
<223> OTHER INFORMATION: Peptide capable of forming a gel by self-
      assembly

<400> SEQUENCE: 97

Arg Phe Val Ile
1

<210> SEQ ID NO 98
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa = cyclohexylalanine
<220> FEATURE:
<221> NAME/KEY: misc_feature
<222> LOCATION: (2)..(2)
<223> OTHER INFORMATION: Xaa can be any naturally occurring amino acid

<400> SEQUENCE: 98

Arg Xaa Val Ile
1

<210> SEQ ID NO 99
<211> LENGTH: 4
<212> TYPE: PRT
```

<213> ORGANISM: Artificial Sequence
<220> FEATURE:
<223> OTHER INFORMATION: Peptide capable of forming a gel by self-
      assembly

<400> SEQUENCE: 99

Arg Val Phe Ile
1

<210> SEQ ID NO 100
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa = cyclohexylalanine
<220> FEATURE:
<221> NAME/KEY: misc_feature
<222> LOCATION: (3)..(3)
<223> OTHER INFORMATION: Xaa can be any naturally occurring amino acid

<400> SEQUENCE: 100

Arg Val Xaa Ile
1

<210> SEQ ID NO 101
<211> LENGTH: 4
<212> TYPE: PRT
<213> ORGANISM: Artificial Sequence
<220> FEATURE:
<223> OTHER INFORMATION: Peptide capable of forming a gel by self-
      assembly

<400> SEQUENCE: 101

Arg Val Ile Phe
1

<210> SEQ ID NO 102
<211> LENGTH: 4
<212> TYPE: PRT
<213> ORGANISM: Artificial Sequence
<220> FEATURE:
<223> OTHER INFORMATION: Peptide capable of forming a gel by self-
      assembly, X or Xaa = cyclohexylalanine
<220> FEATURE:
<221> NAME/KEY: misc_feature
<222> LOCATION: (4)..(4)
<223> OTHER INFORMATION: Xaa can be any naturally occurring amino acid

<400> SEQUENCE: 102

Arg Val Ile Xaa
1

<210> SEQ ID NO 103
<211> LENGTH: 4
<212> TYPE: PRT
<213> ORGANISM: Artificial Sequence
<220> FEATURE:
<223> OTHER INFORMATION: Peptide capable of forming a gel by self-
      assembly

<400> SEQUENCE: 103

Arg Ile Val Phe
1

<210> SEQ ID NO 104
<211> LENGTH: 4
<212> TYPE: PRT
<213> ORGANISM: Artificial Sequence

```
<220> FEATURE:
<223> OTHER INFORMATION: Peptide capable of forming a gel by self-
      assembly, X or Xaa = cyclohexylalanine
<220> FEATURE:
<221> NAME/KEY: misc_feature
<222> LOCATION: (4)..(4)
<223> OTHER INFORMATION: Xaa can be any naturally occurring amino acid

<400> SEQUENCE: 104

Arg Ile Val Xaa
1

<210> SEQ ID NO 105
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein N-terminal  X or Xaa = Dbu
<220> FEATURE:
<221> NAME/KEY: misc_feature
<222> LOCATION: (1)..(1)
<223> OTHER INFORMATION: Xaa can be any naturally occurring amino acid

<400> SEQUENCE: 105

Xaa Phe Val Ile
1

<210> SEQ ID NO 106
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein N-terminal  X or Xaa = Dbu and the other X or
      Xaa = cyclohexylalanine
<220> FEATURE:
<221> NAME/KEY: misc_feature
<222> LOCATION: (1)..(2)
<223> OTHER INFORMATION: Xaa can be any naturally occurring amino acid

<400> SEQUENCE: 106

Xaa Xaa Val Ile
1

<210> SEQ ID NO 107
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein N-terminal  X or Xaa = Dbu
<220> FEATURE:
<221> NAME/KEY: misc_feature
<222> LOCATION: (1)..(1)
<223> OTHER INFORMATION: Xaa can be any naturally occurring amino acid

<400> SEQUENCE: 107

Xaa Val Phe Ile
1

<210> SEQ ID NO 108
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein N-terminal  X or Xaa = Dbu and the other X or
      Xaa = cyclohexylalanine
<220> FEATURE:
<221> NAME/KEY: misc_feature
```

```
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid

<400> SEQUENCE: 108

Xaa Val Xaa Ile
1

<210> SEQ ID NO 109
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein N-terminal  X or Xaa = Dbu
<220> FEATURE:
<221> NAME/KEY: misc_feature
<222> LOCATION: (1)..(1)
<223> OTHER INFORMATION: Xaa can be any naturally occurring amino acid

<400> SEQUENCE: 109

Xaa Val Ile Phe
1

<210> SEQ ID NO 110
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein N-terminal  X or Xaa = Dbu and the other X or
      Xaa = cyclohexylalanine
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 110

Xaa Val Ile Xaa
1

<210> SEQ ID NO 111
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein N-terminal  X or Xaa = Dbu
<220> FEATURE:
<221> NAME/KEY: misc_feature
<222> LOCATION: (1)..(1)
<223> OTHER INFORMATION: Xaa can be any naturally occurring amino acid

<400> SEQUENCE: 111

Xaa Ile Val Phe
1

<210> SEQ ID NO 112
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein N-terminal  X or Xaa = Dbu and the other X or
```

```
                 Xaa = cyclohexylalanine
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 112

Xaa Ile Val Xaa
1

<210> SEQ ID NO 113
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein N-terminal  X or Xaa = Dpr
<220> FEATURE:
<221> NAME/KEY: misc_feature
<222> LOCATION: (1)..(1)
<223> OTHER INFORMATION: Xaa can be any naturally occurring amino acid

<400> SEQUENCE: 113

Xaa Phe Val Ile
1

<210> SEQ ID NO 114
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein N-terminal  X or Xaa = Dpr and the other X or
      Xaa = cyclohexylalanine
<220> FEATURE:
<221> NAME/KEY: misc_feature
<222> LOCATION: (1)..(2)
<223> OTHER INFORMATION: Xaa can be any naturally occurring amino acid

<400> SEQUENCE: 114

Xaa Xaa Val Ile
1

<210> SEQ ID NO 115
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein N-terminal  X or Xaa = Dpr
<220> FEATURE:
<221> NAME/KEY: misc_feature
<222> LOCATION: (1)..(1)
<223> OTHER INFORMATION: Xaa can be any naturally occurring amino acid

<400> SEQUENCE: 115

Xaa Val Phe Ile
1

<210> SEQ ID NO 116
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein N-terminal  X or Xaa = Dpr and the other X or
      Xaa = cyclohexylalanine
```

```
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid

<400> SEQUENCE: 116

Xaa Val Xaa Ile
1

<210> SEQ ID NO 117
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein N-terminal  X or Xaa = Dpr
<220> FEATURE:
<221> NAME/KEY: misc_feature
<222> LOCATION: (1)..(1)
<223> OTHER INFORMATION: Xaa can be any naturally occurring amino acid

<400> SEQUENCE: 117

Xaa Val Ile Phe
1

<210> SEQ ID NO 118
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein N-terminal  X or Xaa = Dpr and the other X or
      Xaa = cyclohexylalanine
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 118

Xaa Val Ile Xaa
1

<210> SEQ ID NO 119
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein N-terminal  X or Xaa = Dpr
<220> FEATURE:
<221> NAME/KEY: misc_feature
<222> LOCATION: (1)..(1)
<223> OTHER INFORMATION: Xaa can be any naturally occurring amino acid

<400> SEQUENCE: 119

Xaa Ile Val Phe
1

<210> SEQ ID NO 120
<211> LENGTH: 4
<212> TYPE: PRT
<213> ORGANISM: Artificial Sequence
<220> FEATURE:
```

```
<223> OTHER INFORMATION: Peptide capable of forming a gel by self-
      assembly, wherein N-terminal  X or Xaa = Dpr and the other X or
      Xaa = cyclohexylalanine
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 120

Xaa Ile Val Xaa
1

<210> SEQ ID NO 121
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein N-terminal  X or Xaa = Orn
<220> FEATURE:
<221> NAME/KEY: misc_feature
<222> LOCATION: (1)..(1)
<223> OTHER INFORMATION: Xaa can be any naturally occurring amino acid

<400> SEQUENCE: 121

Xaa Phe Val Ile
1

<210> SEQ ID NO 122
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein N-terminal  X or Xaa = Orn and the other X or
      Xaa = cyclohexylalanine
<220> FEATURE:
<221> NAME/KEY: misc_feature
<222> LOCATION: (1)..(2)
<223> OTHER INFORMATION: Xaa can be any naturally occurring amino acid

<400> SEQUENCE: 122

Xaa Xaa Val Ile
1

<210> SEQ ID NO 123
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein N-terminal  X or Xaa = Orn
<220> FEATURE:
<221> NAME/KEY: misc_feature
<222> LOCATION: (1)..(1)
<223> OTHER INFORMATION: Xaa can be any naturally occurring amino acid

<400> SEQUENCE: 123

Xaa Val Phe Ile
1

<210> SEQ ID NO 124
<211> LENGTH: 4
<212> TYPE: PRT
<213> ORGANISM: Artificial Sequence
<220> FEATURE:
<223> OTHER INFORMATION: Peptide capable of forming a gel by self-
```

```
       assembly, wherein N-terminal  X or Xaa = Orn and the other X or
       Xaa = cyclohexylalanine
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid

<400> SEQUENCE: 124

Xaa Val Xaa Ile
1

<210> SEQ ID NO 125
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein N-terminal  X or Xaa = Orn
<220> FEATURE:
<221> NAME/KEY: misc_feature
<222> LOCATION: (1)..(1)
<223> OTHER INFORMATION: Xaa can be any naturally occurring amino acid

<400> SEQUENCE: 125

Xaa Val Ile Phe
1

<210> SEQ ID NO 126
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein N-terminal  X or Xaa = Orn and the other X or
      Xaa = cyclohexylalanine
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 126

Xaa Val Ile Xaa
1

<210> SEQ ID NO 127
<211> LENGTH: 4
<212> TYPE: PRT
<213> ORGANISM: Artificial Sequence
<220> FEATURE:
<223> OTHER INFORMATION: Peptide capable of forming a gel by self-
      assembly, wherein N-terminal  X or Xaa = Orn
<220> FEATURE:
<221> NAME/KEY: misc_feature
<222> LOCATION: (1)..(1)
<223> OTHER INFORMATION: Xaa can be any naturally occurring amino acid

<400> SEQUENCE: 127

Xaa Ile Val Phe
1

<210> SEQ ID NO 128
<211> LENGTH: 4
<212> TYPE: PRT
```

```
<213> ORGANISM: Artificial Sequence
<220> FEATURE:
<223> OTHER INFORMATION: Peptide capable of forming a gel by self-
      assembly, wherein N-terminal  X or Xaa = Orn and the other X or
      Xaa = cyclohexylalanine
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 128

Xaa Ile Val Xaa
1
```